United States Patent
Thatcher et al.

(10) Patent No.: US 10,647,709 B2
(45) Date of Patent: *May 12, 2020

(54) CYSTEINE PROTEASE INHIBITORS AND USES THEREOF

(71) Applicants: The Trustees of Columbia University in the City of New York, New York, NY (US); The Board of Trustees of the University of Illinois, Urbana, IL (US)

(72) Inventors: Gregory R. J. Thatcher, Chicago, IL (US); Isaac Thomas Schiefer, Chicago, IL (US); Ottavio Arancio, New York, NY (US); Mauro Fa, New York, NY (US)

(73) Assignees: THE TRUSTEES OF COLUMBIA UNIVERSITY IN THE CITY OF NEW YORK, New York, NY (US); THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/192,113

(22) Filed: Jun. 24, 2016

(65) Prior Publication Data
US 2017/0008884 A1    Jan. 12, 2017

Related U.S. Application Data

(63) Continuation of application No. 14/376,361, filed as application No. PCT/US2013/024364 on Feb. 1, 2013, now Pat. No. 9,403,843.

(60) Provisional application No. 61/593,664, filed on Feb. 1, 2012.

(51) Int. Cl.
| | |
|---|---|
| *C07D 403/12* | (2006.01) |
| *C07D 409/12* | (2006.01) |
| *C07D 417/12* | (2006.01) |
| *C07D 417/14* | (2006.01) |
| *C07D 495/04* | (2006.01) |
| *C07D 303/48* | (2006.01) |
| *C07D 405/12* | (2006.01) |

(52) U.S. Cl.
CPC ......... *C07D 417/12* (2013.01); *C07D 303/48* (2013.01); *C07D 403/12* (2013.01); *C07D 405/12* (2013.01); *C07D 409/12* (2013.01); *C07D 417/14* (2013.01); *C07D 495/04* (2013.01)

(58) Field of Classification Search
CPC .. C07D 403/12; C07D 409/12; C07D 417/12; C07D 417/14; C07D 495/04; C07D 303/48; C07D 405/12
See application file for complete search history.

(56) References Cited

U.S. PATENT DOCUMENTS

| | | | |
|---|---|---|---|
| 5,679,708 A | 10/1997 | Tsubotani et al. | |
| 6,110,967 A | 8/2000 | Asao et al. | |
| 9,403,843 B2 * | 8/2016 | Thatcher | C07D 403/12 |
| 2008/0176841 A1 | 7/2008 | Bogyo et al. | |
| 2011/0105603 A1 | 5/2011 | Ternansky et al. | |

FOREIGN PATENT DOCUMENTS

| | | |
|---|---|---|
| JP | S55-047668 A | 4/1980 |
| JP | S55-115878 A | 9/1980 |
| JP | H08-104683 A | 4/1996 |
| JP | H08-119983 A | 5/1996 |
| JP | 2010500962 A | 1/2010 |
| JP | S5223021 A | 3/2013 |
| WO | WO-2010/074783 | 7/2010 |
| WO | WO-2011/072243 | 6/2011 |
| WO | WO-2012/088420 | 6/2012 |

OTHER PUBLICATIONS

ParkinsonsDisease, 2017, http://www.webmd.com/parkinsons-disease/guide/drug-treatments#1.*
MS, 2017, http://www.webmd.com/multiple-sclerosis/guide/what-is-multiple-sclerosis#2-4.*
HuntingtonsDisease, 2017, http://www.mayoclinic.org/diseases-conditions/huntingtons-disease/diagnosis-treatment/treatment/txc-20321469.*
Trinchese et. al., Journal of Clinical Investigation, vol. 118, No. 8, Aug. 2008, 2796-2807.*
Schiefer et al., Journal of Medicinal Chemistry, 2013, 56, 6054-6058, online publication date Jul. 8, 2013.*
Schiefer et al., Journal of Medicinal Chemistry, 2013, 56 (15), 6054-6068.*
Barrett et al., "L-trans-Epoxysuccinyl-leucylamido(4-guanidino)butane (E-64) and its analogues as inhibitors of cysteine proteinases including cathepsins B, H and L," Biochem. J., 201, pp. 189-198 (1982).
Berge et al., "Pharmaceutical Salts," J. Pharm. Sci., 66(1), pp. 1-19 (1977).
Cuerrier et al., "Calpain Inhibition by α-Ketoamide and Cyclic Hemiacetal Inhibitors Revealed by X-ray Crystallography," Biochemistry, 45, pp. 7446-7452 (2006).
Cuerrier et al., "Determination of peptide substrate specificity for mu-calpain by a peptide library-based approach: the importance of primed side interactions," Journal of Biological Chemistry, 280, pp. 40632-40641 (2005).
Cuerrier et al., "Development of calpain-specific inactivators by screening of positional scanning epoxide libraries," J. Biol. Chem., 282, pp. 9600-9611 (2007).

(Continued)

*Primary Examiner* — Sun Jae Yoo
(74) *Attorney, Agent, or Firm* — Wilmer Cutler Pickering Hale and Dorr LLP

(57) ABSTRACT

The invention provides for novel cysteine protease inhibitors and compositions comprising novel cysteine protease derivatives. The invention further provides for methods for treatment of neurodegenerative diseases comprising administration novel cysteine protease inhibitors or compositions comprising novel cysteine protease inhibitors. In some embodiments, the cysteine protease inhibitors are calpain inhibitors.

17 Claims, 16 Drawing Sheets

Specification includes a Sequence Listing.

(56) References Cited

OTHER PUBLICATIONS

Di Rosa et al., "Calpain Inhibitors: A Treatment for Alzheimer's Disease," J. Mol. Neurosci., 19, pp. 135-141 (2002).
Donkor, "A Survey of Calpain Inhibitors," Current Medicinal Chemistry, 7, pp. 1171-1188 (2000).
Dufty et al., "Calpain-cleavage of alpha-synuclein: connecting proteolytic processing to disease-linked aggregation," The American Journal of Pathology, vol. 170, pp. 1725-1738 (2007).
English translation of Office Action dated Sep. 12, 2016 in corresponding Japanese Patent Application No. 2014-555762 (2 pages).
Extended European Search Report for corresponding European Patent Application No. 13743556.6, dated Aug. 20, 2015 (3 pages).
Goll et al., "The calpain system," Physiological Reviews 2003, 83, 731-801.
Govindarajan et al., "Neuroprotection in glaucoma using calpain-1 inhibitors: regional differences in calpain-1 activity in the trabecular meshwork, optic nerve and implications for therapeutics," Author Manuscript published in final edited form as: CNS Neurol. Disord. Drug Targets, 7, pp. 295-304 (2008), 18 pages.
Greenbaum et al., "Epoxide electrophiles as activity-dependent cysteine protease profiling and discovery tools," Chem. Biol., 7, pp. 569-581 (2000).
Greenbaum et al., "Small molecule affinity fingerprinting. A tool for enzyme family subclassification, target identification, and inhibitor design," Chemistry & Biology, 9, pp. 1085-1094 (2002).
Hanada et al., "A specific thiolprotease inhibitor, E-64 and its derivatives," Peptide Chemistry, pp. 31-36 (1980).
Hanada et al., "Isolation and Characterization of E-64, a New Thiol Protease Inhibitor," Agricultural and Biological Chemistry, 42(3), pp. 523-528 (1978).
Hanna et al., "Calcium-bound structure of calpain and its mechanism of inhibition by calpastatin," Nature, 456, pp. 409-412, 5 pages total (2008).
Hong et al., "Neuroprotection with a calpain inhibitor in a model of focal cerebral ischemia," Stroke, 25, pp. 663-669 (1994).
Hook et al., "Cysteine protease inhibitors reduce brain beta-amyloid and beta-secretase activity in vivo and are potential Alzheimer's disease therapeutics," Biol. Chem., 388, pp. 979-983 (2007).
Huang and Wang, "The calpain family and human disease," Trends in Molecular Medicine, 7(8), pp. 355-362 (2001).
International Search Report and Written Opinion for International Application No. PCT/US2013/024364 dated May 6, 2013 (8 pages).
Lampi et al., "Comparison of cell-permeable calpain inhibitors and E64 in reduction of cataract in cultured rat lenses," Toxicology and Applied Pharmacology 117, pp. 53-57 (1992).
Vosler et al., "Calpain-mediated signaling mechanisms in neuronal injury and neurodegeneration," Author Manuscript published in final edited form as: Molecular Neurobiology, 38, pp. 78-100 (2008), 36 pages.
Miura et al., "Plasma drug concentrations and clinical observations after single or repeated oral administration of afloqualone in healthy volunteers: a phase I study," Rinsho Yakuri, 16, pp. 649-657 (1985).
Mladenovic et al., "Atomistic Insights into the Inhibition of Cysteine Proteases: First QM/MM Calculations Clarifying the Stereoselectivity of Epoxide-Based Inhibitors," The Journal of Physical Chemistry B, 112, pp. 11798-11808 (2008).
Moldoveanu et al., "A $Ca^{2+}$ Switch Aligns the Active Site of Calpain," Cell, 108, pp. 649-660 (2002).
Moldoveanu et al., "Crystal Structures of Calpain-E64 and -Leupeptin Inhibitor Complexes Reveal Mobile Loops Gating the Active Site," Journal of Molecular Biology, 343, pp. 1313-1326 (2004).
Otto and Schirmeister, "Cysteine Proteases and Their Inhibitors," Chem. Rev., 97, pp. 133-171 (1997).
Parkes et al., "Calpain inhibition by peptide epoxides," Biochem. J., 230(2), pp. 509-516 (1985).
Perlmutter et al., "The Ultrastructural Localization of Calcium-Activated Protease "Calpain" in Rat Brain," Synapse, 2, pp. 79-88 (1988).
Pike et al., "Accumulation of calpain and caspase-3 proteolytic fragments of brain-derived alphaII-spectrin in cerebral spinal fluid after middle cerebral artery occlusion in rats," J. Cereb. Blood Flow Metab., 24, pp. 98-106 (2004).
Randriamboavonjy and Fleming, "All cut up! the consequences of calpain activation on platelet function," Vascul. Pharmacol., 56, pp. 210-215 (2012).
Randriamboavonjy et al., "Calpain inhibition stabilizes the platelet proteome and reactivity in diabetes," Blood, 120, pp. 415-423 (2012).
Robertson et al., "Calpain May Contribute to Hereditary Cataract Formation in Sheep," Investigative Ophthalmology & Visual Science, 46, pp. 4634-4640 (2005).
Robertson et al., "Calpain—induced proteolysis in lens epithelial cell death during ovine inherited cataract," Investigative Ophthalmology & Visual Science, 45, 2 pages (2004), Abstract only.
Saatman et al., "Calpain as a therapeutic target in traumatic brain injury," Neurotherapeutics, 7, pp. 31-42 (2010).
Saito et al., "Diethyl (2S,3R)-2-(N-tert-Butoxycarbonyl)Amino-3-Hydroxysuccinate," Organic Syntheses, Coll., vol. 9, p. 220 (1998); vol. 73, pp. 184-193 (1996).
Satoyoshi, "Therapeutic Trials on Progressive Muscular Dystrophy," Intern. Med., 31, pp. 841-846 (1992).
Schiefer et al., "Design, Synthesis, and Optimization of Novel Epoxide Incorporating Peptidomimetics as Selective Calpain Inhibitors," J. Med. Chem., vol. 56, pp. 6054-6068 (2013).
Schirmeister, "New Peptidic Cysteine Protease Inhibitors Derived from the Electrophilic α-Amino Acid Aziridine-2,3-dicarboxylic Acid," Journal of Medicinal Chemistry, 42, pp. 560-572 (1999).
Shea, "Restriction of μM-calcium-requiring calpain activation to the plasma membrane in human neuroblastoma cells: evidence for regionalized influence of a calpain activator protein," J. Neurosci. Res., 48, pp. 543-550 (1997).
Shields et al., "A putative mechanism of demyelination in multiple sclerosis by a proteolytic enzyme, calpain," Proceedings of the National Academy of Sciences, 96, pp. 11486-11491 (1999).
Sugita et al., "Inhibition of epoxide derivatives on chicken calcium-activated neutral protease (CANP) in vitro and in vivo," Journal of Biochemistry, 87, pp. 339-341 (1980).
Suzuki et al., "Amino acid sequence around the active site cysteine residue of calcium-activated neutral protease (CANP)," FEBS Letters, 152, pp. 67-70 (1983).
Murachi, "Calpain and calpastatin," Trends in Biochemical Sciences, 8(5), pp. 167-169 (1983).
Tamai et al., "Prolongation of life span of dystrophic hamster by cysteine proteinase inhibitor, loxistatin (EST)," J. Pharmacobio-Dyn., 10, pp. 678-681 (1987).
Yamashima, "$Ca^{2+}$-dependent proteases in ischemic neuronal death: a conserved 'calpain-cathepsin cascade' from nematodes to primates," Cell Calcium, 36, pp. 285-293 (2004).
Towatari et al., "Novel epoxysuccinyl peptides. A selective inhibitor of cathepsin B, in vivo," FEBS Letters, 280(2), pp. 311-315 (1991).
Veeranna et al., "Calpain mediates calcium-induced activation of the erk1,2 MAPK pathway and cytoskeletal phosphorylation in neurons: relevance to Alzheimer's disease," Am. J. Pathol., 165, pp. 795-805 (2004).
Moseley, J.D. et al., "Preparation of Dicarboxylate Analogues of Cerulenin", Journal of Heterocyclic Chemistry, DOI: 10.1002/HJET.5570420511, 42(5):819-830, Jul.-Aug. 2005 (12 pages).

* cited by examiner

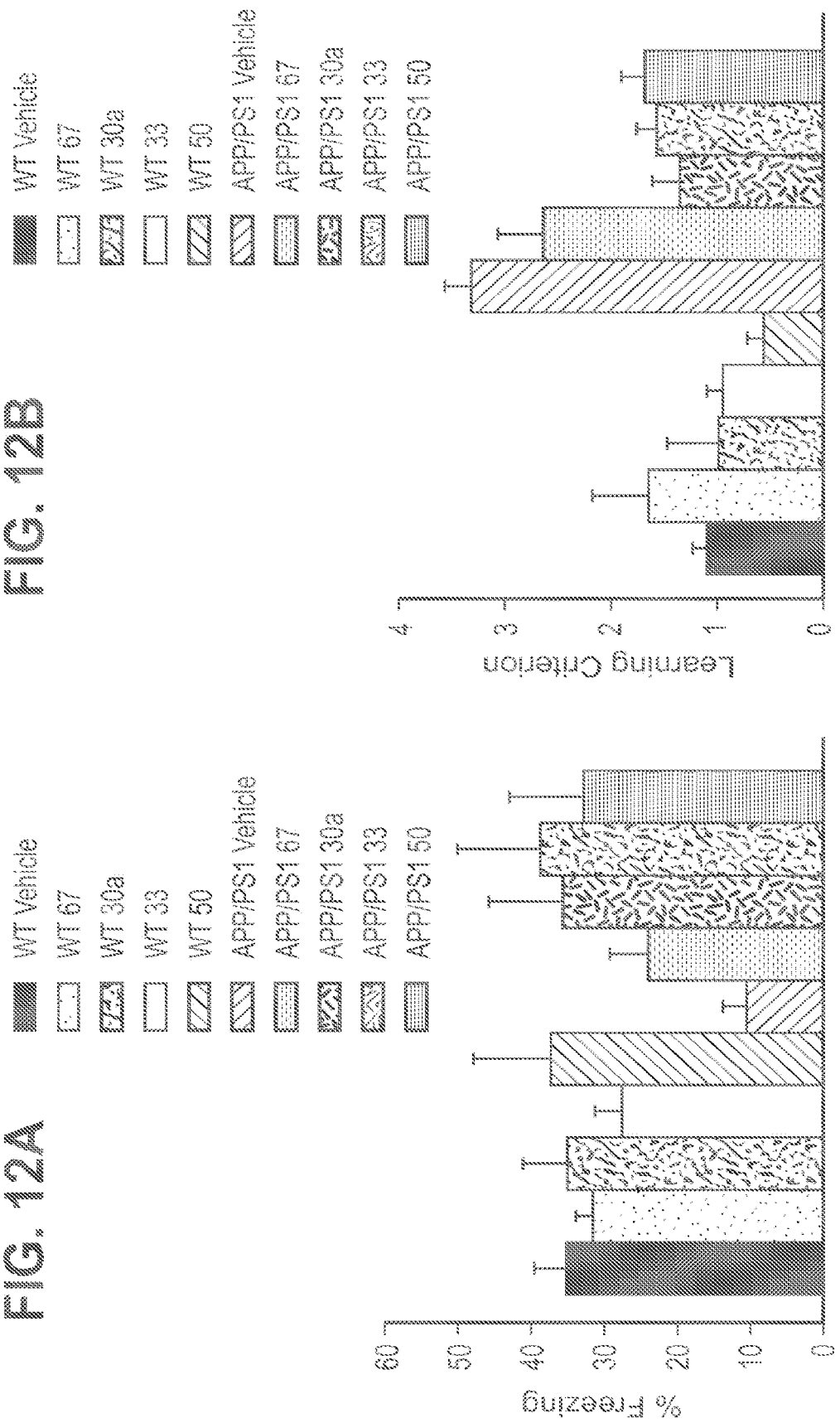

CYSTEINE PROTEASE INHIBITORS AND USES THEREOF

This application claims the benefit of and priority to U.S. Provisional Patent Application No. 61/593,664, filed on Feb. 1, 2012, the content of which is hereby incorporated by reference in its entirety.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

GOVERNMENT SUPPORT

This invention was made with government support under grant AG028713 awarded by the National Institutes of Health. The Government has certain rights in this invention.

BACKGROUND OF THE INVENTION

Calpains are a class of ubiquitously expressed calcium-dependent cysteine proteases that regulate numerous intracellular signaling cascades and are fundamentally involved in regulating protein kinases responsible for cytoskeletal dynamics and remodeling. Under physiological conditions, transient and localized $Ca^{2+}$ fluxes from extracellular or intracellular calcium stores result in controlled activation of local calpain populations. Once activated, calpains are tightly regulated by a selective endogenous peptidyl inhibitor, calpastatin (CAPN). While regional calpain proteolytic activity is essential for native $Ca^{2+}$ signaling and cytoskeletal remodeling, pathological conditions may produce excessive levels of $Ca^{2+}$, resulting in widespread calpain activation and unregulated proteolysis leading to exacerbation of pathological conditions. Hyperactivation of calpain 1 is implicated as a primary or secondary pathological event in a wide range of afflictions and neurodegenerative states, including Alzheimer's Disease. Calpain 1 is primarily localized in synapses, and is abnormally activated in post mortem brains of Alzheimer's Disease patients, while calpastatin is found in significantly low amounts.

Alzheimer's Disease (AD) is a progressive and terminal condition characterized by debilitating memory loss and extensive deterioration of cognitive and functional abilities. Currently available therapies for AD are palliative and do not decelerate or arrest progression of the disease. Cholinesterase inhibitors such as Razadyne® (galantamine), Exelon® (rivastigmine), Aricept® (donepezil), and Cognex® (tacrine) have been prescribed for early stages of AD, and may temporarily delay or halt progression of symptoms. However, as AD progresses, the brain loses less acetylcholine, thereby rendering cholinesterase inhibitors ineffective. Namenda® (memantine), an N-methyl D-aspartate (NMDA) antagonist, is also prescribed to treat moderate to severe Alzheimer's disease; however only temporary benefits are realized.

There is a need for novel calpain inhibitors. There is also a need for novel treatments for a variety of disease states for which calpain 1 is implicated.

SUMMARY OF THE INVENTION

In one aspect, the invention is directed to a class of epoxide derivatives of formula (I)

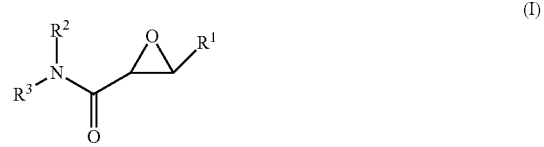

wherein $R^1$ is —$CO_2H$, —$CO_2(C_1$-$C_4)$-alkyl, or aryl;

$R^2$ is hydrogen or —$(C_1$-$C_4)$-alkyl;

$R^3$ is hydrogen, —$(C_1$-$C_4)$-alkyl, —$(C_1$-$C_4)$-alkyl-aryl-$(C_1$-$C_4)$-alkyl-$OR^{10}$, or

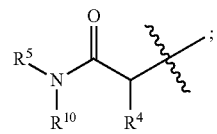

$R^4$ is —$(C_1$-$C_4)$-alkyl, —$(CH_2)$-heteroaryl, wherein said heteroaryl is optionally substituted with one or more —$(C_1$-$C_2)$-alkyl groups, or $R^4$ along with the carbon atom to which it is attached forms a —$(C_4$-$C_8)$-cycloalkyl ring;

$R^5$ is —$(C_1$-$C_6)$-alkyl-$R^6$, —$(C_2$-$C_5)$-alkenyl, —$(C_2$-$C_5)$-alkynyl, —$(CH_2)_n$-aryl, or —$(CH_2)_n$-heteroaryl, wherein said aryl or heteroaryl are optionally substituted with one or more $R^7$ groups;

$R^6$ is —$N(R^{10})C(O)R^8$, —$N(R^{10})S(O)_2R^8$, —$N(R^{10})C(NH)N(R^{10})_2$;

$R^7$ is independently halogen, —$(C_1$-$C_3)$-alkyl, aryl, methylenedioxyphenyl, —$S(O)_2N(R^{10})_2$, or —$S(O)_2N(R^{10})_2$, wherein said aryl is optionally substituted with one or more $R^9$ groups;

$R^8$ is —$(C_1$-$C_6)$-alkyl-$R^{11}$ or aryl, wherein aryl is optionally substituted with one or more $R^9$ groups;

$R^9$ is independently hydrogen, halogen, —$(C_1$-$C_4)$-alkyl, —$(C_1$-$C_4)$-haloalkyl, —$(C_2$-$C_4)$-alkynyl, CN, $NO_2$, —$S(O)_2N(R^{10})_2$, or

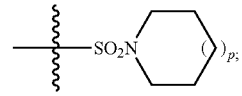

$R^{10}$ is independently hydrogen or —$(C_1$-$C_4)$-alkyl;

$R^{11}$ is hydrogen,

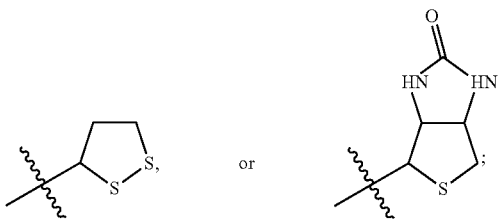 [SMILES: *C1CCSS1 ; *C1SCC2NC(=O)NC21]

n is an integer from 0-4; and
p is an integer from 0-3; or a pharmaceutically acceptable salt thereof.

In some embodiments, $R^1$ is not —$CO_2H$ when $R^2$ is hydrogen and $R^3$ is isopropyl,

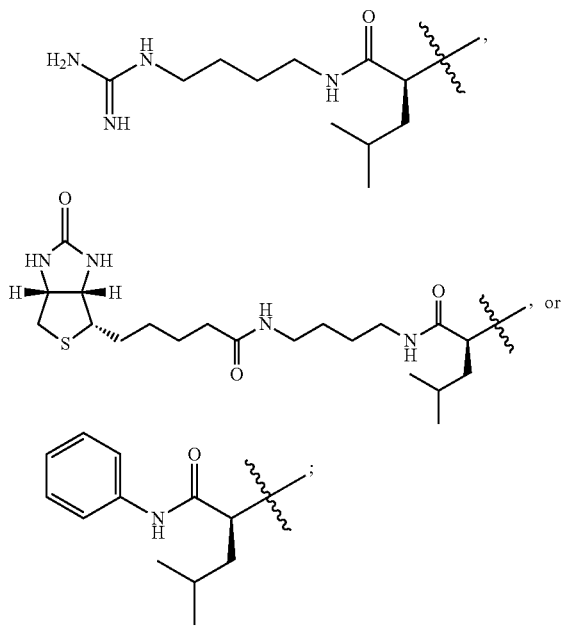

and
$R^1$ is not —$CO_2$-ethyl when $R^2$ and $R^3$ are both hydrogen.

In another aspect, the invention is directed to compositions comprising a compound of formula (I) and a pharmaceutically acceptable carrier.

In another aspect, the invention is directed to a method of inhibiting a cysteine protease comprising contacting a cysteine protease with a compound of formula (I) or a composition comprising a compound of formula (I). In some embodiments, the cysteine protease is calpain.

In another aspect, the invention is directed to a method of treating neurodegenerative disease in a subject comprising administration of a therapeutically effective amount of a compound of formula (I). In some embodiments, the disease is Alzheimer's Disease.

In another aspect, the invention is directed to a method of increasing long-term potentiation in a subject comprising administration of a therapeutically effective amount of a compound of formula (I).

In another aspect, the invention is directed to a method of improving memory in a subject comprising administration of a therapeutically effective amount of a compound of formula (I). In some embodiments, the subject has a neurodegenerative disease. In some embodiments, the neurodegenerative disease is Alzheimer's Disease.

In another aspect, the invention is directed to a method of improving synaptic function in a subject comprising administration of a therapeutically effective amount of a compound of formula (I). In some embodiments, the subject has a neurodegenerative disease. In some embodiments, the neurodegenerative disease is Alzheimer's Disease.

Still other objects and advantages of the invention will become apparent to those of skill in the art from the disclosure herein, which is simply illustrative and not restrictive. Thus, other embodiments will be recognized by the skilled artisan without departing from the spirit and scope of the invention.

BRIEF DESCRIPTION OF THE FIGURES

(FIG. 3A) After capping of free cysteines with iodoacetamide (IAA) and in gel digest, peptide fragments were analyzed by LC-MS/MS. (FIG. 3B) Total ion chromatograms (TIC) for the incubation of recombinant Cal1$_{cat}$ (5 µM) in the absence or presence of inhibitors (10 µM). A non-active site and IAA-capped peptide fragment ($R_t$=41.3 min) was used as an internal standard for EIC quantitation. (FIG. 3C) Active site Cys modification of Cal1$_{cat}$ was concentration dependent in incubation containing Cal1$_{cat}$ (1 µM) and vary concentrations of inhibitors. (FIG. 3D) Co-incubation of Cal1$_{cat}$ (1 µM) with an inhibitor mixture (5 µM) showed competitive modification of the active site by 24a and E-64.

FIG. 5A) Structural overlay of putative docking poses; FIG. 5B) Magnified S2 pocket illustrating proposed H-bond formed between the conserved $H_2O$ molecule and the P2 moiety. Docking was carried out via GOLD docking platform using Sybyl molecular modeling software. Docking poses rendered using UCSF Chimera molecular modeling software.

FIG. 12A-12B shows daily treatment with 67, 30a, 33 and 50 from the age of 2 months until 3 months ameliorated the defect in contextual fear memory (A) and reference memory (B) in APP/PS1 mice. APP/PS1-vehicle: n=15; APP/PS1-67: n=6; APP/PS1-30a: n=10; WT-vehicle: n=15; WT-67=5; WT-30a: n=8, APP/PS1-33: n=11; WT-33: n=8, APP/PS1-50: n=10; WT-50: n=8. $P<0.05$ in all transgenic groups treated with compound compared to their respective vehicle-treated transgenics.

DETAILED DESCRIPTION OF THE INVENTION

Figure 1:
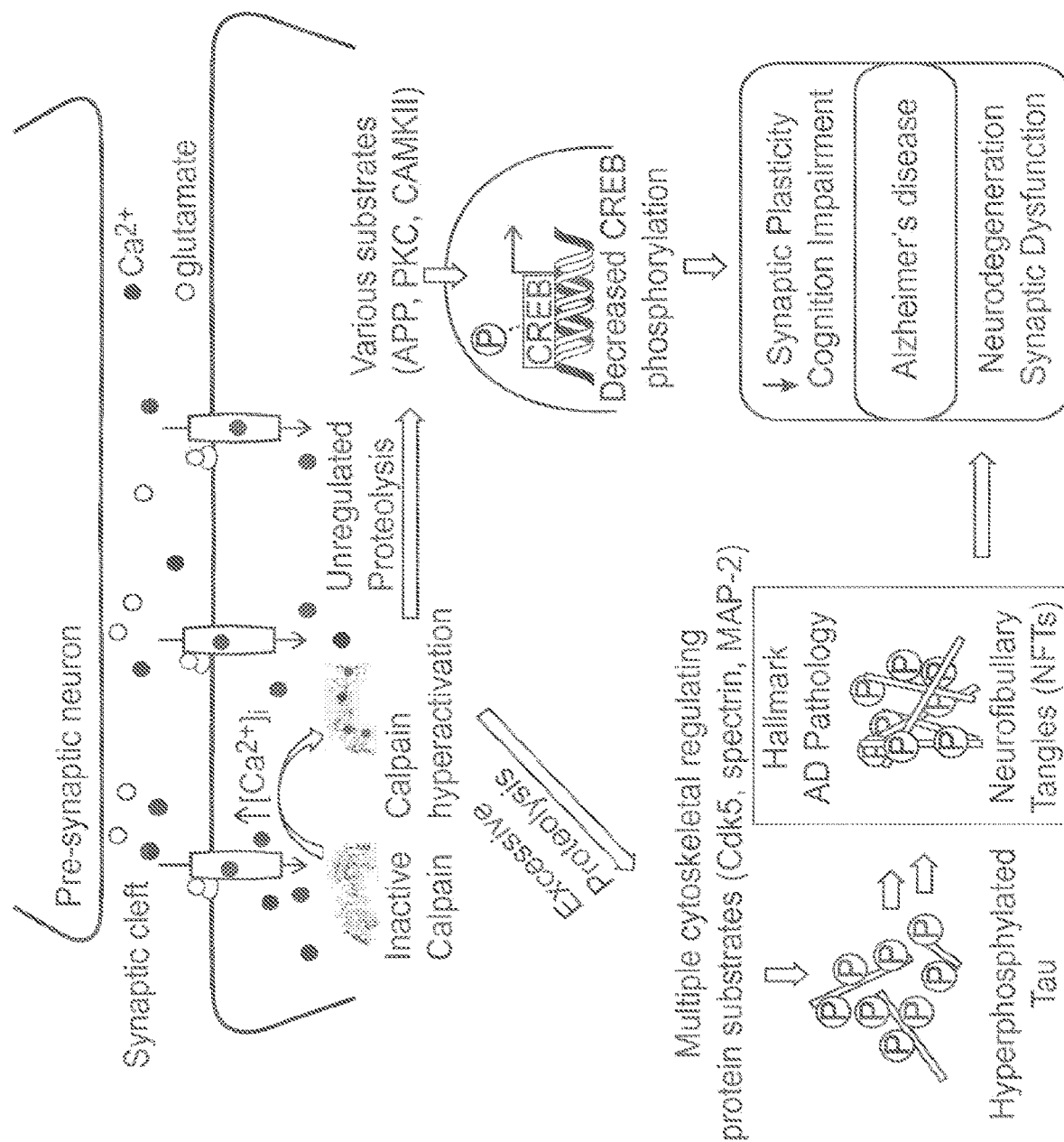
FIG. 1 shows the involvement of calpain in various biological processes.

Calpains are a class of ubiquitously expressed calcium-dependent cysteine proteases that regulate numerous intracellular signaling cascades and are fundamentally involved in regulating protein kinases responsible for cytoskeletal dynamics and remodeling (Goll, D. E. et al., *Physiological Reviews* 2003, 83, 731-801; Perlmutter, L. S. et al., *Synapse* 1988, 2, 79-88; Veeranna et al., *Am J Pathol* 2004, 165, 795-805; Shea, T. B. *J Neurosci Res* 1997, 48, 543-50; each herein incorporated by reference in its entirety). Under physiological conditions, transient and localized $Ca^{2+}$ fluxes from extracellular or intracellular calcium stores result in controlled activation of local calpain populations (FIG. 1). Once activated, calpains are tightly regulated by a selective 47 kDa endogenous peptidyl inhibitor, calpastatin (CAPN) (Goll, D. E. et al., *Physiological Reviews* 2003, 83, 731-801; Hanna, R. A. et al., *Nature* 2008, 456, 409-412; Takashi, M. *Trends in Biochemical Sciences* 1983, 8, 167-169; each herein incorporated by reference in its entirety).

While regional calpain proteolytic activity is essential for native $Ca^{2+}$ signaling and cytoskeletal remodeling, pathological conditions may produce excessive levels of $Ca^{2+}$, resulting in widespread calpain activation and unregulated proteolysis leading to exacerbation of pathological conditions (Di Rosa, G. et al., *J Mol Neurosci* 2002, 19, 135-41; Huang, Y. et al., *Trends in Molecular Medicine* 2001, 7, 355-362; each herein incorporated by reference in its entirety). Calpain proteolytic activity contributes to secondary degeneration in situations of acute cellular stress following myocardial ischemia, cerebral ischemia, and traumatic brain injury (Saatman, K. et al., *Neurotherapeutics* 2010, 7, 31-42; Hong, S. C. et al., *Stroke* 1994, 25, 663-9; Yamashima, T. *Cell Calcium* 2004, 36, 285-293; Pike, B. R. et al., *J Cereb Blood Flow Metab* 2004, 24, 98-106; each herein incorporated by reference in its entirety). Furthermore, calpain hyperactivation has been suggested to be a primary contributor in a wide range of pathological states associated with altered $Ca^{2+}$ homeostasis, including: Huntington's disease, Parkinson's disease (PD), cataract formation, glaucoma, multiple sclerosis (MS); and Alzheimer's disease (AD) (Di Rosa, G. et al., *J Mol Neurosci* 2002, 19, 135-41; Shields, D. C. et al., *Proceedings of the National Academy of Sciences* 1999, 96, 11486-11491; Dufty, B. M. et al., *The American Journal of Pathology* 2007, 170, 1725-1738; Vosler, P. et al., *Molecular Neurobiology* 2008, 38, 78-100; Robertson, L. J. G. et al., *Investigative Ophthalmology & Visual Science* 2005, 46, 4634-4640; Robertson, L. J. G. et al., *Invest. Ophthalmol. Vis. Sci.* 2004, 45, 2653-B288; Govindarajan, B. et al., *CNS Neurological Disorders—Drug Targets (Formerly Current Drug Targets—CNS & Neurological Disorders)* 2008, 7, 295-304; each herein incorporated by reference in its entirety). Enhanced calpain activity in platelets is a contributor to atherothrombosis and diabetes pathology (Randriamboavonjy, V. et al., *Vascul Pharmacol* 2012, 56, 210-5; Randriamboavonjy, V. et al., *Blood* 2012, 120, 415-23; each herein incorporated by reference in its entirety). Direct blockade of clapain proteolytic activity has been shown to rescue neurons from glutamate excitotoxicity. Calpain hyperactivation is involved in downregulating phosphorylation of the memory related transcription factor CREB, resulting in weakened synaptic transmission and cognition impairment. In this context, a selective and potent calpain inhibitor may hold therapeutic potential for a range of disease states.

Attempts to develop calpain inhibitors have been cataloged previously (Donkor, I. O., *Current Medicinal Chemistry* 2000, 7, 1171; herein incorporated by reference in its entirety). The structural nomenclature of cysteine protease substrates and inhibitors is introduced in FIG. 2. The majority of reported calpain inhibitors rely upon the ability of an electrophilic reactive group, or "warhead", to either reversibly or irreversibly modify the active site cysteine of calpain. A natural product, E-64, L-trans-epoxysuccinyl-leucylamido(4-guanidino)butane (FIG. 2), was an early identified cysteine protease inhibitor, utilizing an epoxide for active site modification (Parkes, C. et al., *Biochem. J* 1985, 230, 509-516; Sugita, H. et al., *Journal of Biochemistry* 1980, 87, 339-341; each herein incorporated by reference in its entirety). While being non-reactive towards other protease super-families (i.e. aspartic, serine, etc.), E-64 serves as a high affinity, non-selective, irreversible calpain inhibitor with poor bioavailability (K. Hanada, M. T. et al., *Agricultural and Biological Chemistry* 1978, 42, 523-528; Barrett, A. J. et al., *Biochem. J* 1982, 201, 189-198; each herein incorporated by reference in its entirety).

CA clan cysteine proteases (i.e. papain, calpains, and lysosomal cathepsins) have similar P1-P3 substrate binding pockets, which results in a common preference for hydrophobic residues at the S2 subsite (i.e. Leu, Ile, Val, Phe, Tyr) (Greenbaum, D. et al., *Chem Biol* 2000, 7, 569-81; Greenbaum, D. C. et al., *Chemistry & Biology* 2002, 9, 1085-1094; each herein incorporated by reference in its entirety). It has been suggested that inhibitors containing S,S epoxide stereochemistry bind preferentially into the P1-P3 pocket of CA clan proteases (Mladenovic, M. et al., *The Journal of Physical Chemistry B* 2008, 112, 11798-11808; Otto, H. H. et al., *Chem Rev* 1997, 97, 133-172; each herein incorporated by reference in its entirety). Accordingly, E-64 and related S,S epoxides containing hydrophobic residues at the P2 position have shown poor selectivity and high potency for these proteases. Recent efforts examined an array of P4-P3-P2-epoxysuccinate peptides for inhibitory activity against CA clan cysteine proteases, including: Cal1, Cal1$_{cat}$ (calpain-1 catalytic domain), the lysosomal cysteine protease cathepsin (Cath), and papain (Cuerrier, D. et al., *J Biol Chem* 2007, 282, 9600-11; herein incorporated by reference in its entirety). While these peptides possessed poor drug like properties, their activity profiles give valuable insight into the design and development of novel selective calpain inhibitors using peptidomimetic epoxides. Herein, we describe the development of such potent, selective, calpain inhibitors. Three successive generations of inhibitors were synthesized using computationally assisted design and Cal1 inhibition data. Modification of the active site cysteine was confirmed using LC-MS/MS and the relative selectivity assessed: i) against CathB using a novel biotinylated probe; and ii) against papain using an enzyme kinetics analysis.

Figure 2:
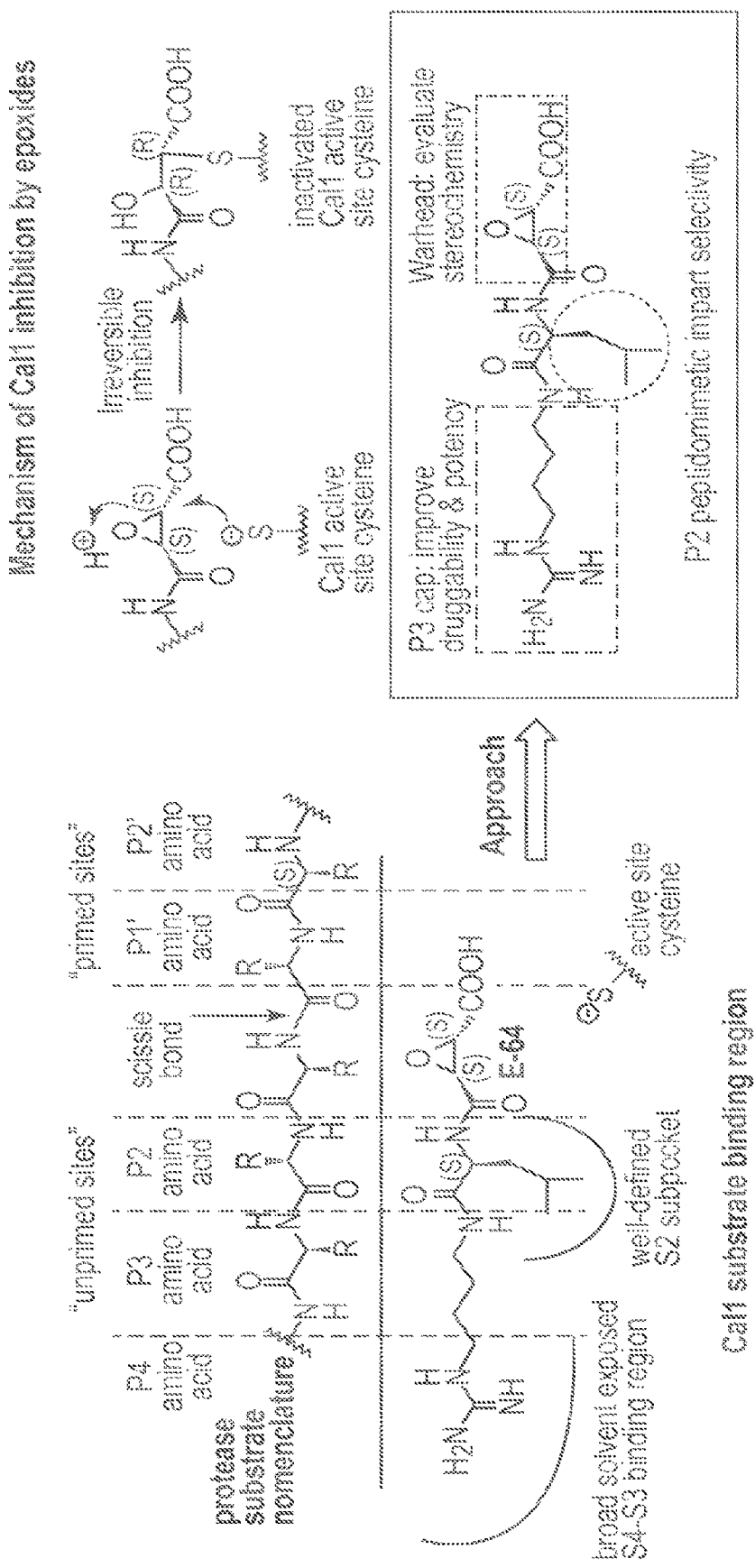
FIG. 2 shows protease substrates are designated according to their amino acid residues extending from the scissile bond. "Unprimed" and "primed" substrate residues are designated P1, P2, etc. and P1', P2', etc., respectively. The design rationale is illustrated using E-64 as a lead.

The epoxysuccinate moiety of E-64 is considered to be essential for potent cysteine protease inhibition. Alternatives to the epoxide warhead, such as alkene and aziridine analogs, possess weak inhibitory activity (Parkes, C. et al., *Biochem. J* 1985, 230, 509-516; Schirmeister, T. *Journal of Medicinal Chemistry* 1999, 42, 560-572; each herein incorporated by reference in its entirety). Despite concerns regarding potential ADMET complications stemming from incorporation of the epoxysuccinate moiety, E-64 and derivatives have been approved for clinical studies (Miyahara, T. et al., *Rinsho Yakuri* 1985, 16, 537-546; Satoyashi, E. *Intern. Med.* 1992, 31, 841-846; Scrip. 1992, 1765; each herein incorporated by reference in its entirety), and there are multiple reports of in vivo efficacy and safety by E-64 and related epoxysuccinate analogs in mice (M. Tamai, K. M. et al., *J. Pharmacobiodyn.* 1986, 9, 672-677; Towatari, T. et al., *FEBS Letters* 1991, 280, 311-15; Hook, G. et al., *Biol Chem* 2007, 388, 979-83; Masaharu Tamai, S. O. et al., *Journal of Pharmacobio-Dynamics* 1987, 10, 678-681; each herein incorporated by reference in its entirety). Retention of the epoxysuccinate group also facilitates the design of activity-based probes to identify off-target proteins that may contribute to efficacy. Given these considerations, we chose to retain the epoxysuccinate moiety and focused optimization efforts on modifying and evaluating two main portions of the peptidomimetic scaffold: 1) the P3/P4 cap group, and 2) the P2 site that is occupied by a L-leucine in E-64 (FIG. 2).

In one aspect, the invention is directed to a class of epoxide derivatives of formula (I).

In some embodiments of formula (I), $R^1$ is —$CO_2H$ or —$CO_2(C_1$-$C_4)$-alkyl;
$R^2$ is hydrogen or —$(C_1$-$C_4)$-alkyl;
$R^3$ is

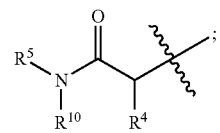

$R^4$ is —$(C_1$-$C_4)$-alkyl, —$(CH_2)$-heteroaryl, wherein said heteroaryl is optionally substituted with one or more —$(C_1$-$C_2)$-alkyl groups, or $R^4$ along with the carbon atom to which it is attached forms a —$(C_4$-$C_8)$-cycloalkyl ring;
$R^5$ is —$(C_1$-$C_6)$-alkyl-$R^6$, —$(C_2$-$C_5)$-alkenyl, —$(C_2$-$C_5)$-alkynyl, —$(CH_2)_n$-aryl, or —$(CH_2)_n$-heteroaryl, wherein said aryl or heteroaryl are substituted with one or more $R^7$ groups;
$R^6$ is —$N(R^{10})C(O)R^8$ or —$N(R^{10})S(O)_2R^8$;
$R^7$ is independently halogen, —$(C_1$-$C_3)$-alkyl, aryl, methylenedioxyphenyl, —$S(O)_2N(R^{10})_2$, or —$S(O)_2N(R^{10})_2$, wherein said aryl is optionally substituted with one or more $R^9$ groups;
$R^8$ is —$(C_1$-$C_6)$-alkyl-$R^{11}$ or aryl, wherein aryl is optionally substituted with one or more $R^9$ groups;
$R^9$ is independently hydrogen, halogen, —$(C_1$-$C_4)$-alkyl, —$(C_1$-$C_4)$-haloalkyl, —$(C_2$-$C_4)$-alkynyl, CN, $NO_2$, —$S(O)_2N(R^{10})_2$, or

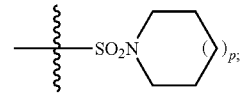

$R^{10}$ is independently hydrogen or —$(C_1$-$C_4)$-alkyl;
$R^{11}$ is hydrogen or

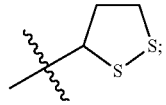 [SMILES: *C1CCSS1]

n is an integer from 0-4; and
p is an integer from 0-3.

In some embodiments, the compound of formula (I) is a compound of formula (I-a),

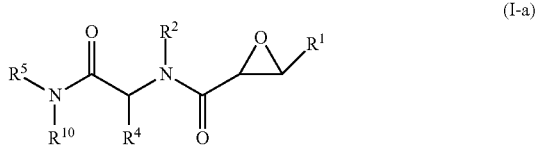

wherein, $R^1$ is —$CO_2H$ or —$CO_2(C_1$-$C_4)$-alkyl;

$R^2$ is hydrogen or —$(C_1$-$C_4)$-alkyl;

$R^4$ is —$(C_1$-$C_4)$-alkyl, —$(CH_2)$-heteroaryl, wherein said heteroaryl is optionally substituted with one or more —$(C_1$-$C_2)$-alkyl groups, or $R^4$ along with the carbon atom to which it is attached forms a —$(C_4$-$C_8)$-cycloalkyl ring;

$R^5$ is —$(C_1$-$C_6)$-alkyl-$R^6$, —$(C_2$-$C_5)$-alkenyl, —$(C_2$-$C_5)$-alkynyl, —$(CH_2)_n$-aryl, or —$(CH_2)_n$-heteroaryl, wherein said aryl or heteroaryl are substituted with one or more $R^7$ groups;

$R^6$ is —$N(R^{10})C(O)R^8$ or —$N(R^{10})S(O)_2R^8$;

$R^7$ is independently halogen, —$(C_1$-$C_3)$-alkyl, aryl, methylenedioxyphenyl, —$S(O)_2N(R^{10})_2$, or —$S(O)_2N(R^{10})_2$, wherein said aryl is optionally substituted with one or more $R^9$ groups;

$R^8$ is —$(C_1$-$C_6)$-alkyl-$R^{11}$ or aryl, wherein aryl is optionally substituted with one or more $R^9$ groups;

$R^9$ is independently hydrogen, halogen, —$(C_1$-$C_4)$-alkyl, —$(C_1$-$C_4)$-haloalkyl, —$(C_2$-$C_4)$-alkynyl, CN, $NO_2$, —$S(O)_2N(R^{10})_2$, or

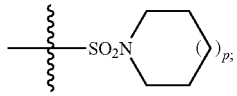

$R^{10}$ is independently hydrogen or —$(C_1$-$C_4)$-alkyl;
$R^{11}$ is hydrogen or

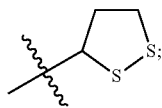

n is an integer from 0-4; and
p is an integer from 0-3.

ABBREVIATIONS AND DEFINITIONS

The term "compound of the invention" as used herein means a compound of formula (I) or any subgenus or species thereof. The term is also intended to encompass salts, hydrates, and solvates thereof.

The term "composition(s) of the invention" as used herein means compositions comprising a compound of the invention. The compositions of the invention may further comprise other agents such as, for example, carriers, excipients, stabilants, lubricants, solvents, and the like.

A "pharmaceutical composition" refers to a mixture of one or more of the compounds of the invention with other chemical components, such as physiologically acceptable carriers and excipients. The purpose of a pharmaceutical composition is to facilitate administration of a compound to an organism or subject.

The term "pharmaceutically acceptable salt" is intended to include salts derived from inorganic or organic acids including, for example hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids; and salts derived from inorganic or organic bases including, for example sodium, potassium, calcium, ammonium or tetrafluoroborate. Exemplary pharmaceutically acceptable salts are found, for example, in Berge, et al. (J. Pharm. Sci. 1977, 66(1), 1; hereby incorporated by reference in its entirety).

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in Remington's Pharmaceutical Sciences (Alfonso Gennaro ed., Krieger Publishing Company (1997); Remington's: The Science and Practice of Pharmacy, 21$^{st}$ Ed. (Lippincot, Williams & Wilkins (2005); Modern Pharmaceutics, vol. 121 (Gilbert Banker and Christopher Rhodes, CRC Press (2002); each of which hereby incorporated by reference in its entirety).

In some embodiments, $R^1$ is —$CO_2H$ or —$CO_2(C_1$-$C_4)$-alkyl. In some embodiments, $R^1$ is —$CO_2H$ or —$CO_2(C_1$-$C_2)$-alkyl. In some embodiments, $R^1$ is —$CO_2H$.

In some embodiments, $R^2$ is hydrogen or —$(C_1$-$C_4)$-alkyl. In some embodiments, $R^2$ is hydrogen or —$(C_1$-$C_2)$-alkyl. In some embodiments, $R^2$ is hydrogen or methyl. In some embodiments, $R^2$ is hydrogen.

In some embodiments, $R^3$ is hydrogen, —$(C_1$-$C_4)$-alkyl, —$(C_1$-$C_4)$-alkyl-aryl-$(C_1$-$C_4)$-alkyl-$OR^{10}$, or

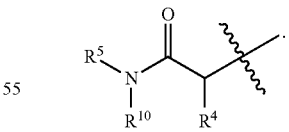

In some embodiments, $R^3$ is hydrogen, —$(C_1$-$C_4)$-alkyl, or

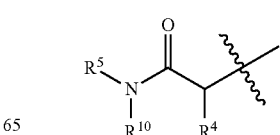
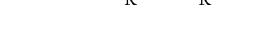

In some embodiments, $R^3$ is hydrogen, —($C_1$-$C_2$)-alkyl, or

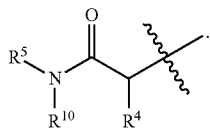

In some embodiments, $R^3$ is

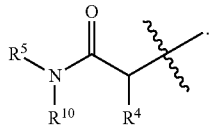

In some embodiments, $R^4$ is —($C_1$-$C_4$)-alkyl, —($CH_2$)-heteroaryl, wherein said heteroaryl is optionally substituted with one or more —($C_1$-$C_2$)-alkyl groups, or $R^4$ along with the carbon atom to which it is attached forms a —($C_4$-$C_8$)-cycloalkyl ring. In some embodiments, $R^4$ is —($C_1$-$C_4$)-alkyl, —($CH_2$)-heteroaryl, wherein said heteroaryl is optionally substituted with one or more —($C_1$-$C_2$)-alkyl groups. In some embodiments, $R^4$ is —($C_2$-$C_4$)-alkyl, —($CH_2$)-heteroaryl, wherein said heteroaryl is optionally substituted with one or more —($C_1$-$C_2$)-alkyl groups. In some embodiments, $R^4$ is —$CH_2CH(CH_3)_2$, —($CH_2$)-thiazolyl, —($CH_2$)-imidazolyl, wherein said thiazolyl or imidazolyl is optionally substituted with one or more —($C_1$-$C_2$)-alkyl groups. In some embodiments, $R^4$ is —$CH_2CH(CH_3)_2$, —($CH_2$)-thiazolyl, —($CH_2$)-imidazolyl, wherein said thiazolyl or imidazolyl is optionally substituted with one or more —($C_1$-$C_2$)-alkyl groups. In some embodiments, $R^4$ is —($CH_2$)-thiazolyl, —($CH_2$)-imidazolyl, wherein said imidazolyl is optionally substituted with a methyl group. In some embodiments, $R^4$ is

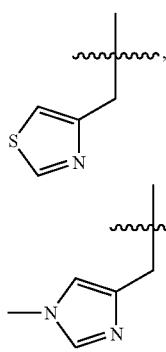
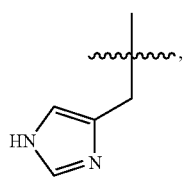

In some embodiments, $R^4$ is

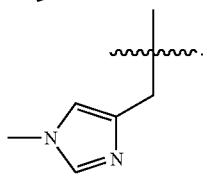

In some embodiments, $R^4$ is

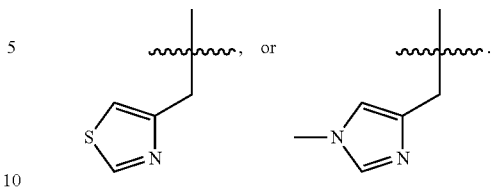

In some embodiments, $R^4$ is

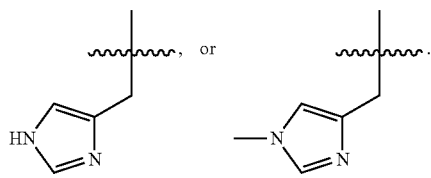

In some embodiments, $R^4$ is

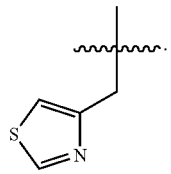

In some embodiments, $R^4$ is

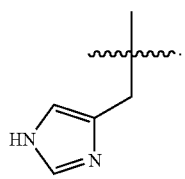

In some embodiments, $R^4$ is

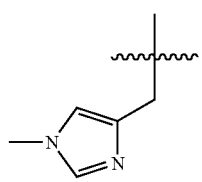

In some embodiments, $R^5$ is —($C_1$-$C_6$)-alkyl-$R^6$, —($C_2$-$C_5$)-alkenyl, —($C_2$-$C_5$)-alkynyl, —($CH_2$)$_n$-aryl, or —($CH_2$)$_n$-heteroaryl, wherein said aryl or heteroaryl are optionally substituted with one or more $R^7$ groups. In some embodiments, $R^5$ is —($C_1$-$C_6$)-alkyl-$R^6$, —($C_2$-$C_5$)-alkenyl, —($C_2$-$C_5$)-alkynyl, —($CH_2$)$_n$-aryl, or —($CH_2$)$_n$-heteroaryl, wherein said aryl or heteroaryl are substituted with one or more $R^7$ groups. In some embodiments, $R^5$ is —($C_1$-$C_4$)-alkyl-$R^6$, —($CH_2$)$_n$-aryl, or —($CH_2$)$_n$-heteroaryl, wherein said aryl or heteroaryl are substituted with one or more $R^7$ groups. In some embodiments, $R^5$ is —($CH_2$)$_n$-aryl, or —($CH_2$)$_n$-heteroaryl, wherein said aryl or heteroaryl are substituted with one or more $R^7$ groups. In some embodiments, $R^5$ is —($CH_2$)$_n$-phenyl, or —($CH_2$)$_n$-heteroaryl, wherein said phenyl or heteroaryl are substituted with one or more $R^7$ groups. In some embodiments, $R^5$ is thiazolyl or —(CH$_2$)-triazolyl, wherein said thiazolyl or triazolyl are substituted with an $R^7$ group. In some embodiments, $R^5$ is

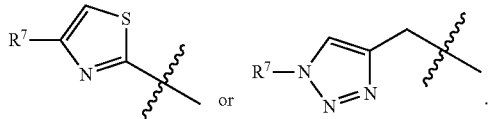

In some embodiments, $R^5$ is

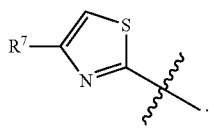

In some embodiments, $R^5$ is

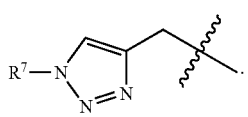

In some embodiments, $R^6$ is —N($R^{10}$)C(O)$R^8$, —N($R^{10}$)S(O)$_2R^8$, —N($R^{10}$)C(NH)N($R^{10}$)$_2$. In some embodiments, $R^6$ is —N($R^{10}$)C(O)$R^8$. In some embodiments, $R^6$ is —N($R^{10}$)S(O)$_2R^8$.

In some embodiments, $R^7$ is independently halogen, —(C$_1$-C$_3$)-alkyl, aryl, methylenedioxyphenyl, —S(O)$_2$N(R$^{10}$)$_2$, or —S(O)$_2$N(R$^{10}$)$_2$, wherein said aryl is optionally substituted with one or more $R^9$ groups. In some embodiments, $R^7$ is independently halogen, —(C$_1$-C$_3$)-alkyl, phenyl, methylenedioxyphenyl, —S(O)$_2$N(R$^{10}$)$_2$, or —S(O)$_2$N(R$^{10}$)$_2$, wherein said phenyl is optionally substituted with one or more $R^9$ groups. In some embodiments, $R^7$ is phenyl optionally substituted with one or more $R^9$ groups.

In some embodiments, $R^8$ is —(C$_1$-C$_6$)-alkyl-$R^{11}$ or aryl, wherein aryl is optionally substituted with one or more $R^9$ groups. In some embodiments, $R^8$ is —(C$_1$-C$_6$)-alkyl-$R^{11}$ or phenyl, wherein phenyl is optionally substituted with one or more $R^9$ groups.

In some embodiments, $R^9$ is independently hydrogen, halogen, —(C$_1$-C$_4$)-alkyl, —(C$_1$-C$_4$)-haloalkyl, —(C$_2$-C$_4$)-alkynyl, CN, NO$_2$, —S(O)$_2$N(R$^{10}$)$_2$, or

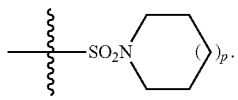

In some embodiments, $R^9$ is independently hydrogen, halogen, —(C$_1$-C$_2$)-alkyl, —(C$_1$-C$_2$)-haloalkyl, —(C$_2$-C$_4$)-alkynyl, CN, NO$_2$, —S(O)$_2$N(R$^{10}$)$_2$, or

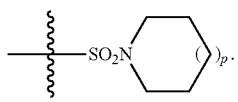

In some embodiments, $R^9$ is independently halogen, —(C$_1$-C$_2$)-alkyl, —(C$_1$-C$_2$)-haloalkyl, —(C$_2$-C$_4$)-alkynyl, CN, NO$_2$, —S(O)$_2$N(R$^{10}$)$_2$, or

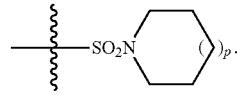

In some embodiments, $R^9$ is independently halogen, —(C$_1$-C$_2$)-alkyl, —(C$_1$-C$_2$)-haloalkyl, —(C$_2$-C$_4$)-alkynyl, NO$_2$, —S(O)$_2$N(R$^{10}$)$_2$, or

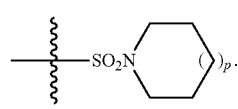

In some embodiments, $R^9$ is independently halogen, —(C$_1$-C$_2$)-alkyl, —(C$_1$-C$_2$)-haloalkyl, —S(O)$_2$N(R$^{10}$)$_2$, or

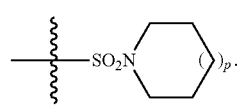

In some embodiments, $R^9$ is independently halogen, methyl, halomethyl, —S(O)$_2$N(R$^{10}$)$_2$, or

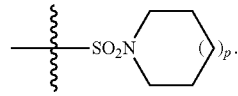

In some embodiments, $R^9$ is independently F, Br, Cl, methyl, trifluoromethyl, —S(O)$_2$NH$_2$, or

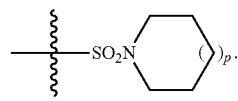

In some embodiments, $R^9$ is independently F, Br, Cl, methyl, trifluoromethyl, or

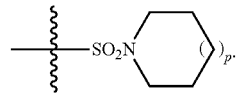

In some embodiments, $R^9$ is independently F, Br, Cl, methyl, or trifluoromethyl. In some embodiments, $R^9$ is independently F, Br, Cl, or trifluoromethyl. In some embodiments, $R^9$ is halogen. In some embodiments, $R^9$ is independently F, Br, or Cl. In some embodiments, $R^9$ is independently F or Br. In some embodiments, $R^9$ is F.

In some embodiments, $R^{10}$ is independently hydrogen or —(C$_1$-C$_4$)-alkyl. In some embodiments, $R^{10}$ is independently hydrogen or —(C$_1$-C$_2$)-alkyl. In some embodiments, $R^{10}$ is independently hydrogen or methyl. In some embodiments, $R^{10}$ is hydrogen. In some embodiments, $R^{10}$ is methyl.

In some embodiments, $R^{11}$ is hydrogen or

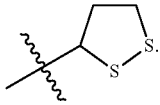

In some embodiments, $R^{11}$ is hydrogen. In some embodiments, $R^{11}$ is

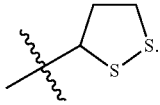

In some embodiments, n is an integer from 0-4. In some embodiments, n is an integer from 0-3. In some embodiments, n is an integer from 0-2. In some embodiments, n is 0 or 1. In some embodiments, n is an integer from 1-4. In some embodiments, n is an integer from 1-3. In some embodiments, n is 0. In some embodiments, n is 1. In some embodiments, n is 2.

In some embodiments, p is an integer from 0-3. In some embodiments, p is an integer from 0-2. In some embodiments, p is 0 or 1. In some embodiments, p is 0. In some embodiments, p is 1.

In some embodiments, the compounds are of the (S)-configuration at the carbon atom to which $R^4$ is attached. In some embodiments, the compounds are of the (R)-configuration at the carbon atom to which $R^4$ is attached.

In some embodiments, the compounds are of the (S,S)-configuration at the epoxide. In some embodiments, the compounds are of the (R,R)-configuration at the epoxide.

In some embodiments,
$R^1$ is —$CO_2H$ or —$CO_2(C_1\text{-}C_4)$-alkyl;
$R^2$ is hydrogen or —$(C_1\text{-}C_4)$-alkyl;
$R^4$ is —$(C_1\text{-}C_4)$-alkyl, —$(CH_2)$-heteroaryl, wherein said heteroaryl is optionally substituted with one or more —$(C_1\text{-}C_2)$-alkyl groups;
$R^5$ is —$(C_1\text{-}C_4)$-alkyl-$R^6$, —$(CH_2)_n$-aryl, or —$(CH_2)_n$-heteroaryl, wherein said aryl or heteroaryl are substituted with one or more $R^7$ groups;
$R^6$ is —$N(R^{10})C(O)R^8$ or —$N(R^{10})S(O)_2R^8$;
$R^7$ is independently halogen, —$(C_1\text{-}C_3)$-alkyl, aryl, methylenedioxyphenyl, —$S(O)_2N(R^{10})_2$, or —$S(O)_2N(R^{10})_2$, wherein said aryl is optionally substituted with one or more $R^9$ groups;
$R^8$ is —$(C_1\text{-}C_6)$-alkyl-$R^{11}$ or aryl, wherein aryl is optionally substituted with one or more $R^9$ groups;
$R^9$ is independently hydrogen, halogen, —$(C_1\text{-}C_2)$-alkyl, —$(C_1\text{-}C_2)$-haloalkyl, —$(C_2\text{-}C_4)$-alkynyl, CN, $NO_2$, —$S(O)_2N(R^{10})_2$, or

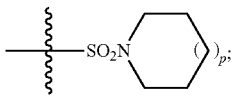

$R^{10}$ is independently hydrogen or —$(C_1\text{-}C_4)$-alkyl;
$R^{11}$ is hydrogen or

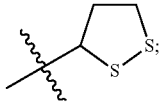 [SMILES: *C1CCSS1]

n is an integer from 0-2; and
p is an integer from 0-1.
In some embodiments,
$R^1$ is —$CO_2H$ or —$CO_2(C_1\text{-}C_4)$-alkyl;
$R^2$ is hydrogen or —$(C_1\text{-}C_4)$-alkyl;
$R^4$ is —$(C_1\text{-}C_4)$-alkyl, —$(CH_2)$-thiazolyl, —$(CH_2)$-imidazolyl, wherein said thiazolyl or imidazolyl is optionally substituted with one or more —$(C_1\text{-}C_2)$-alkyl groups;
$R^5$ is —$(CH_2)_n$-aryl, or —$(CH_2)_n$-heteroaryl, wherein said aryl or heteroaryl are substituted with one or more $R^7$ groups;
$R^7$ is independently halogen, —$(C_1\text{-}C_3)$-alkyl, aryl, methylenedioxyphenyl, —$S(O)_2N(R^{10})_2$, or —$S(O)_2N(R^{10})_2$, wherein said aryl is optionally substituted with one or more $R^9$ groups;
$R^9$ is independently hydrogen, halogen, —$(C_1\text{-}C_2)$-alkyl, —$(C_1\text{-}C_2)$-haloalkyl, —$(C_2\text{-}C_4)$-alkynyl, CN, $NO_2$, —$S(O)_2N(R^{10})_2$, or

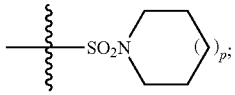

$R^{10}$ is independently hydrogen or —$(C_1\text{-}C_4)$-alkyl;
n is an integer from 0-2; and
p is an integer from 0-1.
In some embodiments,
$R^1$ is —$CO_2H$ or —$CO_2(C_1\text{-}C_2)$-alkyl;
$R^2$ is hydrogen or —$(C_1\text{-}C_2)$-alkyl;
$R^4$ is —$CH_2CH(CH_3)_2$, —$(CH_2)$-thiazolyl, —$(CH_2)$-imidazolyl, wherein said thiazolyl or imidazolyl is optionally substituted with one or more —$(C_1\text{-}C_2)$-alkyl groups;
$R^5$ is —$(CH_2)_n$-phenyl, or —$(CH_2)_n$-heteroaryl, wherein said phenyl or heteroaryl are substituted with one or more $R^7$ groups;
$R^7$ is independently halogen, —$(C_1\text{-}C_3)$-alkyl, phenyl, methylenedioxyphenyl, —$S(O)_2N(R^{10})_2$, or —$S(O)_2N(R^{10})_2$, wherein said phenyl is optionally substituted with one or more $R^9$ groups;
$R^9$ is independently hydrogen, halogen, —$(C_1\text{-}C_2)$-alkyl, —$(C_1\text{-}C_2)$-haloalkyl, —$(C_2\text{-}C_4)$-alkynyl, CN, $NO_2$, —$S(O)_2N(R^{10})_2$, or

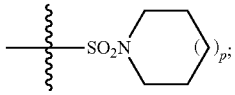

$R^{10}$ is independently hydrogen or —$(C_1\text{-}C_2)$-alkyl;
n is an integer from 0-2; and
p is an integer from 0-1.
In some embodiments,
$R^1$ is —$CO_2H$ or —$CO_2(C_1\text{-}C_2)$-alkyl;
$R^2$ is hydrogen or —$(C_1\text{-}C_2)$-alkyl;

$R^4$ is —CH$_2$CH(CH$_3$)$_2$, —(CH$_2$)-thiazolyl, —(CH$_2$)-imidazolyl, wherein said thiazolyl or imidazolyl is optionally substituted with one or more —(C$_1$-C$_2$)-alkyl groups;

$R^5$ is thiazolyl or —(CH$_2$)-triazolyl, wherein said thiazolyl or triazolyl are substituted with an $R^7$ group;

$R^7$ is phenyl optionally substituted with one or more $R^9$ groups;

$R^9$ is independently halogen, —(C$_1$-C$_2$)-alkyl, —(C$_1$-C$_2$)-haloalkyl, —(C$_2$-C$_4$)-alkynyl, CN, NO$_2$, —S(O)$_2$N(R$^{10}$)$_2$, or

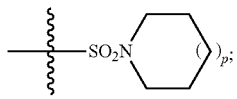

$R^{10}$ is independently hydrogen or —(C$_1$-C$_2$)-alkyl; and p is an integer from 0-1.

In some embodiments, $R^1$ is —CO$_2$H or —CO$_2$(C$_1$-C$_2$)-alkyl;

$R^2$ is hydrogen or —(C$_1$-C$_2$)-alkyl;

$R^4$ is —(CH$_2$)-thiazolyl, —(CH$_2$)-imidazolyl, wherein said imidazolyl is optionally substituted with a methyl group;

$R^5$ is thiazolyl or —(CH$_2$)-triazolyl, wherein said thiazolyl or triazolyl are substituted with an $R^7$ group;

$R^7$ is phenyl optionally substituted with one or more $R^9$ groups;

$R^9$ is independently halogen, —(C$_1$-C$_2$)-alkyl, —(C$_1$-C$_2$)-haloalkyl, —(C$_2$-C$_4$)-alkynyl, CN, NO$_2$, —S(O)$_2$N(R$^{10}$)$_2$, or

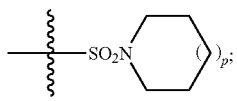

$R^{10}$ is independently hydrogen or methyl; and p is an integer from 0-1.

In some embodiments, $R^1$ is —CO$_2$H or —CO$_2$(C$_1$-C$_2$)-alkyl;

$R^2$ is hydrogen; $R^4$ is

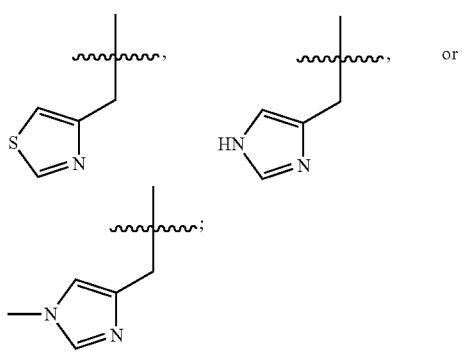

$R^5$ is

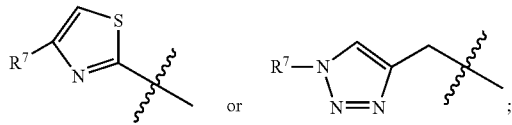

$R^7$ is phenyl optionally substituted with one or more $R^9$ groups;

$R^9$ is independently halogen, —(C$_1$-C$_2$)-alkyl, —(C$_1$-C$_2$)-haloalkyl, —(C$_2$-C$_3$)-alkynyl, NO$_2$, —S(O)$_2$NH$_2$, or

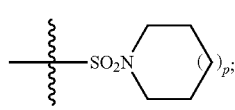

and p is an integer from 0-1.

In some embodiments, the compound is selected from
(2S,3S)-3-((S)-1-(2,6-difluorophenylamino)-4-methyl-1-oxopentan-2-ylcarbamoyl)oxirane-2-carboxylic acid;
(2S,3S)-3-((S)-1-(4-(4-fluorophenyl)thiazol-2-ylamino)-4-methyl-1-oxopentan-2-ylcarbamoyl)oxirane-2-carboxylic acid;
(2R,3R)-3-((S)-1-(4-(4-fluorophenyl)thiazol-2-ylamino)-4-methyl-1-oxopentan-2-ylcarbamoyl)oxirane-2-carboxylic acid;
(2S,3S)-3-(1-(4-(4-fluorophenyl)thiazol-2-ylamino)-3-(1H-imidazol-4-yl)-1-oxopropan-2-ylcarbamoyl)oxirane-2-carboxylic acid;
(2S,3S)-3-((S)-1-(4-(4-fluorophenyl)thiazol-2-ylamino)-1-oxo-3-(thiazol-4-yl)propan-2-ylcarbamoyl)oxirane-2-carboxylic acid;
(2S,3S)-3-((S)-1-(4-(4-ethynylphenyl)thiazol-2-ylamino)-1-oxo-3-(thiazol-4-yl)propan-2-ylcarbamoyl)oxirane-2-carboxylic acid;
(2S,3S)-3-((S)-1-(4-(4-fluorophenyl)thiazol-2-ylamino)-3-(1-methyl-1H-imidazol-4-yl)-1-oxopropan-2-ylcarbamoyl)oxirane-2-carboxylic acid;
(2S,3S)-3-((S)-1-((1-(4-fluorophenyl)-1H-1,2,3-triazol-4-yl)methylamino)-1-oxo-3-(thiazol-4-yl)propan-2-ylcarbamoyl)oxirane-2-carboxylic acid; and
(2S,3S)-3-((S)-1-((1-(4-bromophenyl)-1H-1,2,3-triazol-4-yl)methylamino)-1-oxo-3-(thiazol-4-yl)propan-2-ylcarbamoyl)oxirane-2-carboxylic acid.

In some embodiments, the compound is selected from
(2S,3S)-3-((S)-1-(2,6-difluorophenylamino)-4-methyl-1-oxopentan-2-ylcarbamoyl)oxirane-2-carboxylic acid;
(2S,3S)-3-((S)-1-(4-(4-fluorophenyl)thiazol-2-ylamino)-4-methyl-1-oxopentan-2-ylcarbamoyl)oxirane-2-carboxylic acid;
(2S,3S)-3-(1-(4-(4-fluorophenyl)thiazol-2-ylamino)-3-(1H-imidazol-4-yl)-1-oxopropan-2-ylcarbamoyl)oxirane-2-carboxylic acid;
(2S,3S)-3-((S)-1-(4-(4-fluorophenyl)thiazol-2-ylamino)-1-oxo-3-(thiazol-4-yl)propan-2-ylcarbamoyl)oxirane-2-carboxylic acid;
(2S,3S)-3-((S)-1-(4-(4-ethynylphenyl)thiazol-2-ylamino)-1-oxo-3-(thiazol-4-yl)propan-2-ylcarbamoyl)oxirane-2-carboxylic acid;
(2S,3S)-3-((S)-1-((1-(4-fluorophenyl)-1H-1,2,3-triazol-4-yl)methylamino)-1-oxo-3-(thiazol-4-yl)propan-2-ylcarbamoyl)oxirane-2-carboxylic acid; and (2S,3S)-3-((S)-1-((1-(4-bromophenyl)-1H-1,2,3-triazol-4-yl)methylamino)-1-oxo-3-(thiazol-4-yl)propan-2-ylcarbamoyl)oxirane-2-carboxylic acid.

In some embodiments, the compound is selected from
(2S,3S)-3-(1-(4-(4-fluorophenyl)thiazol-2-ylamino)-3-(1H-imidazol-4-yl)-1-oxopropan-2-ylcarbamoyl)oxirane-2-carboxylic acid;
(2S,3S)-3-((S)-1-(4-(4-fluorophenyl)thiazol-2-ylamino)-1-oxo-3-(thiazol-4-yl)propan-2-ylcarbamoyl)oxirane-2-carboxylic acid;
(2S,3S)-3-((S)-1-((1-(4-fluorophenyl)-1H-1,2,3-triazol-4-yl)methylamino)-1-oxo-3-(thiazol-4-yl)propan-2-ylcarbamoyl)oxirane-2-carboxylic acid; and
(2S,3S)-3-((S)-1-((1-(4-bromophenyl)-1H-1,2,3-triazol-4-yl)methylamino)-1-oxo-3-(thiazol-4-yl)propan-2-ylcarbamoyl)oxirane-2-carboxylic acid.

In another aspect, the invention is directed to compositions comprising a compound of formula (I) and a pharmaceutically acceptable carrier.

In another aspect, the invention is directed to a method of treating disease in a subject comprising administration of a therapeutically effective amount of a compound of formula (I). In some embodiments, the disease is characterized by calpain hyperactivation. In some embodiments, the disease is cataract formation, glaucoma, atherothrombosis or diabetes. In some embodiments, the disease is a neurological disorder. In some embodiments, the disease is a neurodegenerative disease. In some embodiments, the neurodegenerative disease is Huntington's Disease, Parkinson's Disease, multiple sclerosis or Alzheimer's Disease. In some embodiments, the disease is Alzheimer's Disease.

In another aspect, the invention is directed to a method of treating neurodegenerative disease in a subject comprising administration of a therapeutically effective amount of a composition comprising a compound of formula (I). In some embodiments, the disease is Alzheimer's Disease.

In another aspect, the invention is directed to a method of increasing long-term potentiation in a subject comprising administration of a therapeutically effective amount of a compound of formula (I). In some embodiments, the subject has a neurodegenerative disease. In some embodiments, the neurodegenerative disease is Alzheimer's Disease.

In another aspect, the invention is directed to a method of increasing long-term potentiation in a subject comprising administration of a therapeutically effective amount of a composition comprising a compound of formula (I). In some embodiments, the subject has a neurodegenerative disease. In some embodiments, the neurodegenerative disease is Alzheimer's Disease.

In another aspect, the invention is directed to a method of improving memory in a subject comprising administration of a therapeutically effective amount of a compound of formula (I). In some embodiments, the subject has a neurodegenerative disease. In some embodiments, the neurodegenerative disease is Alzheimer's Disease.

In another aspect, the invention is directed to a method of improving memory in a subject comprising administration of a therapeutically effective amount of a composition comprising a compound of formula (I). In some embodiments, the subject has a neurodegenerative disease. In some embodiments, the neurodegenerative disease is Alzheimer's Disease.

In another aspect, the invention is directed to a method of improving synaptic function in a subject comprising administration of a therapeutically effective amount of a compound of formula (I). In some embodiments, synaptic function comprises synaptic plasticity. In some embodiments, synaptic plasticity comprises learning, memory, or a combination thereof. In some embodiments, synaptic plasticity comprises long term potentiation (LTP). In some embodiments, the subject has a neurodegenerative disease. In some embodiments, the neurodegenerative disease is Alzheimer's Disease.

In another aspect, the invention is directed to a method of improving synaptic function in a subject comprising administration of a therapeutically effective amount of a composition comprising a compound of formula (I). In some embodiments, synaptic function comprises synaptic plasticity. In some embodiments, synaptic plasticity comprises learning, memory, or a combination thereof. In some embodiments, synaptic plasticity comprises long term potentiation (LTP). In some embodiments, the subject has a neurodegenerative disease. In some embodiments, the neurodegenerative disease is Alzheimer's Disease.

Another aspect of the invention provides a method for increasing memory retention in a subject afflicted with a neurodegenerative disease, the method comprising administering to a subject a therapeutic amount of a compound of formula (I) or a composition comprising a compound of formula (I).

In some embodiments, a compound of formula (I) is administered. In some embodiments, a composition comprising a compound of formula (I) is administered.

Exemplary neurodegenerative diseases and methods of treatment therefor are also described in WO 2010/074783, WO2011/072243, and WO2012/088420, each herein incorporated by reference in its entirety.

Compounds of formula (I) can be incorporated into pharmaceutical compositions suitable for administration. Such compositions can comprise a compound of formula (I) and a pharmaceutically acceptable carrier. Thus, in some embodiments, the compounds of the invention are present in a pharmaceutical composition.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

Any of the therapeutic applications described herein can be applied to any subject in need of such therapy, including, for example, a mammal such as a mouse, a rat, a dog, a cat, a cow, a horse, a rabbit, a monkey, a pig, a sheep, a goat, or a human. In some embodiments, the subject is a mouse, rat or human. In some embodiments, the subject is a mouse. In some embodiments, the subject is a rat. In some embodiments, the subject is a human.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyethylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the compound in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Epoxide based cysteine protease inhibitors are synthesized by methods within the purview of the ordinarily skilled artisan. Exemplary methods by which such derivatives can be synthesized are as follows. Generation of a library of peptidomimetic epoxides possessing either natural or non-natural peptidomimetic residues at the P2 position, designated the $R_1$ substituent, and varying the P3/P4 cap groups, designated as $R_2$ in Scheme 1.

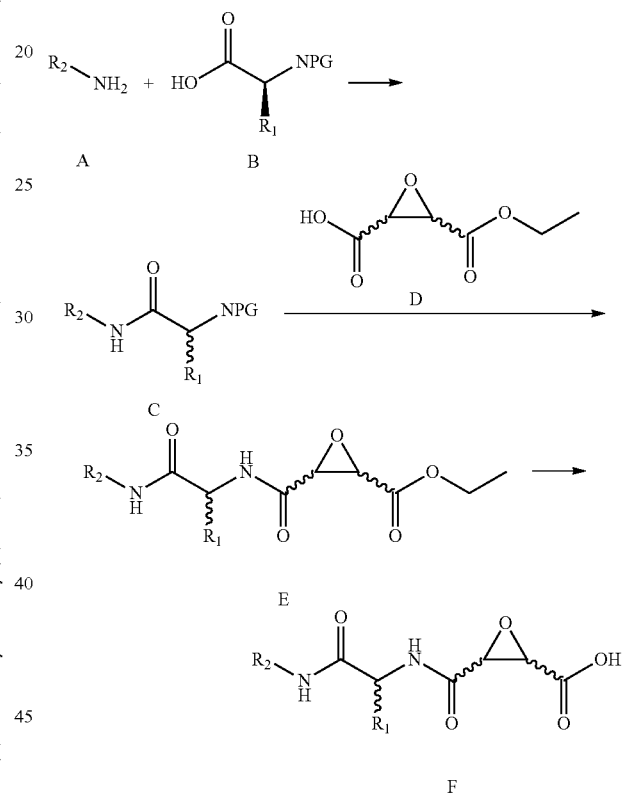

Scheme 1. Exemplary Synthesis of Compounds of the Invention.

Initially, the $R_2$-amines (A) can be coupled to the commercially available protected (PG denotes protecting group) amino acids (B) following typical peptide coupling procedures using, exemplary coupling reagents such as HOBT and EDCI, or in the presence of CDI to give the corresponding protected peptidomimetic scaffolds (C) (Scheme 1). The epoxysuccinates D can be synthesized in 3 steps starting from either L-DET or D-DET following published procedures (Saito, S. et al., Organic Syntheses 1996, 73, 184; herein incorporated by reference in its entirety). Following removal of the protecting group, the appropriate peptidomimetic scaffold can be coupled to epoxysuccinates D using coupling reagents such as, for example, EDCI and HOBT to give the corresponding epoxide esters (E). Ester saponification using, for example a base such as LiOH, provides the analogous epoxy acids F.

An alternative convergent synthesis can also be employed wherein the epoxide functionality is incorporated after derivatization, although a divergent synthetic approach is preferred for library development during lead optimization (Scheme 2). An exemplary convergent route entails synthesis of G by conventional means, followed by installation of epoxides D and ultimate conversion to compounds F. A divergent approach has also been developed wherein a key intermediate such as G' is used to develop a library of compounds F'.

Dipolar cycloaddition reactions such as the copper catalyzed Huisgen cycloaddition, a.k.a. "click chemistry", have received much attention in the past decade due to low cross-reactivity with other functional groups, making it a useful tool for the generation of a library of epoxide compounds of the invention. For example, a key alkynyl intermediate such as G'' can be functionalized with azides using a copper catalyzed Huisgen cycloaddition (Scheme 3), with the aid of TBTA to give the corresponding triazole-epoxyesters H, followed by saponification to provide F'''.

Scheme 2. Exemplary Convergent and Divergent Approaches for Synthesis of Compounds of the Invention.

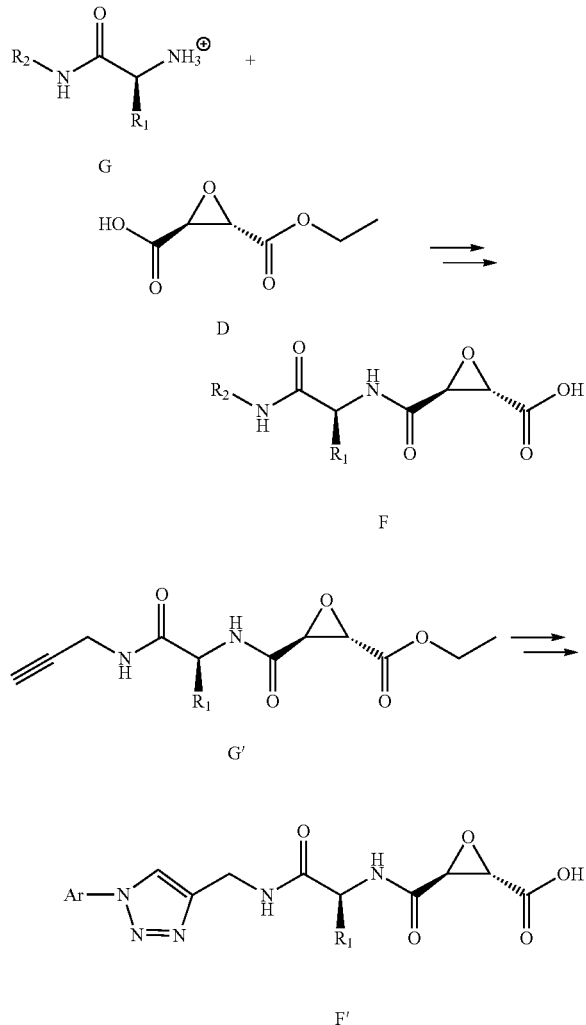

Scheme 3. Click chemistry route to triazole containing compounds of the invention.

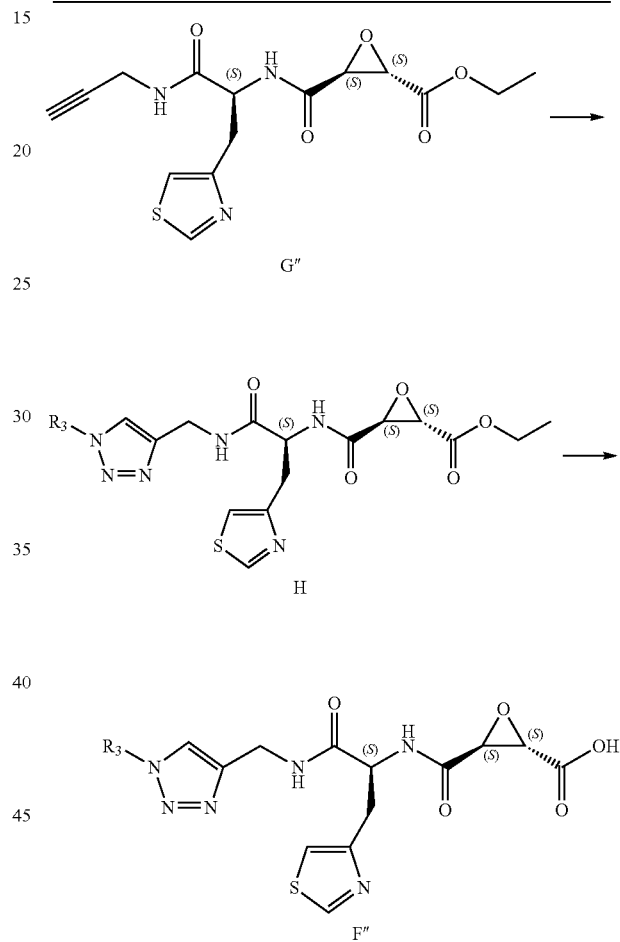

In some embodiments, the compound of the invention are selected from the following:

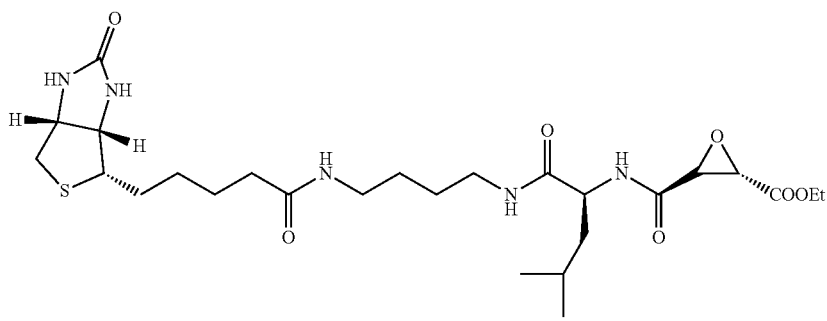

-continued
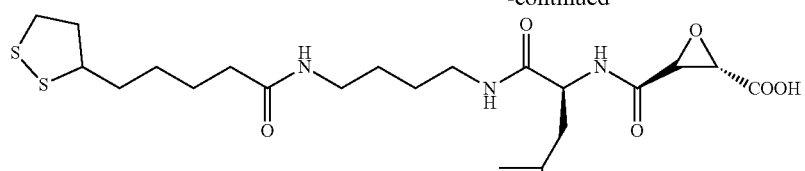
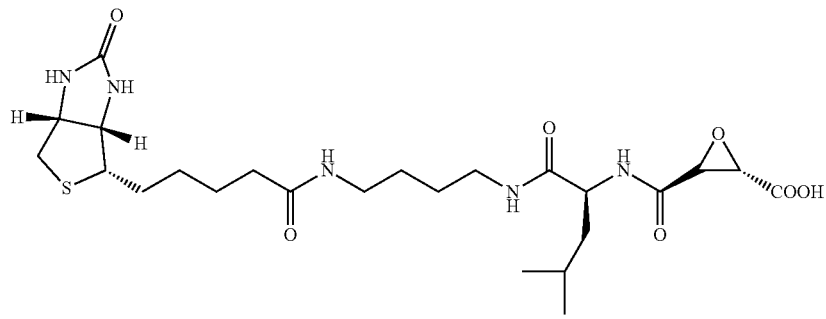
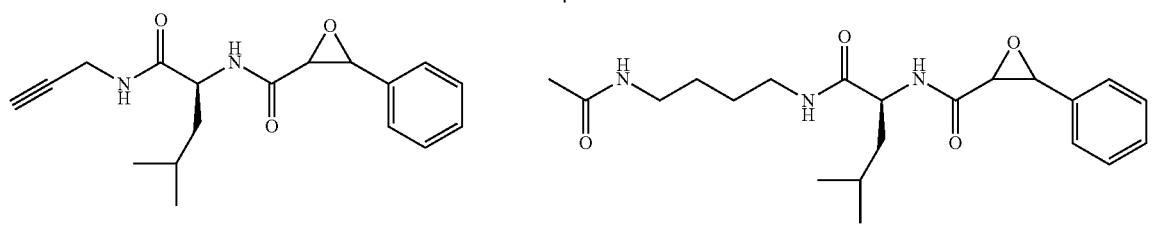
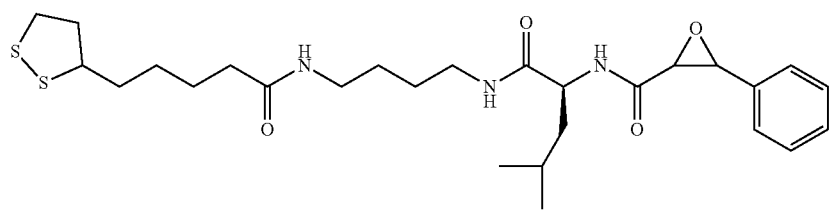
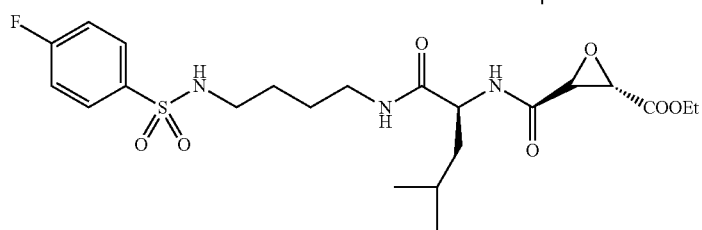
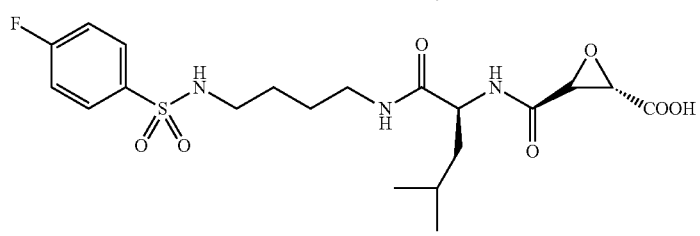
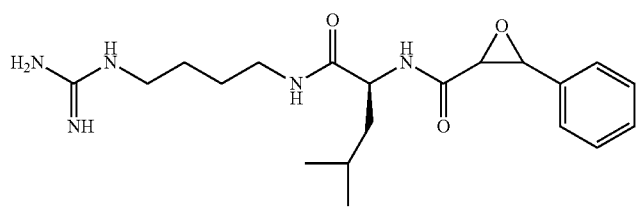
HCl Salt

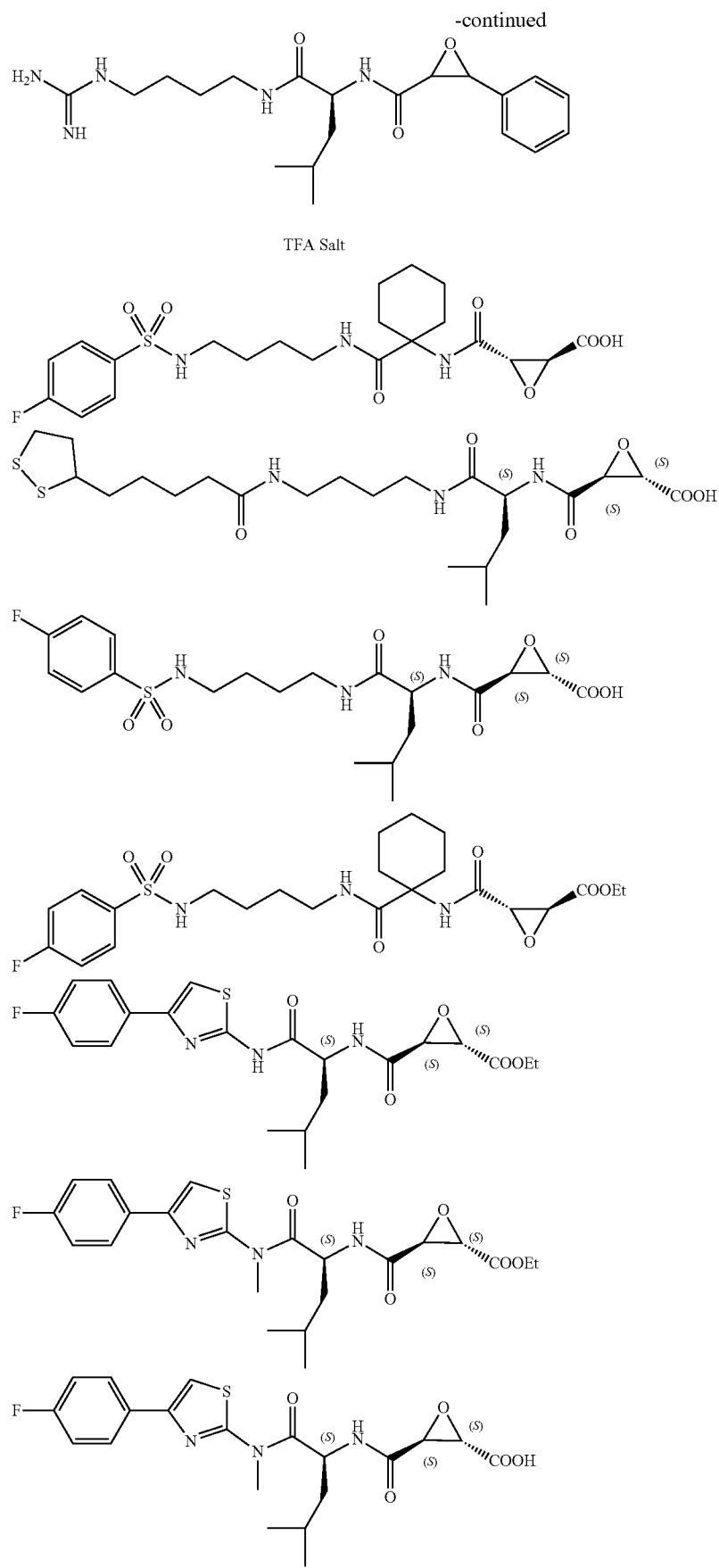

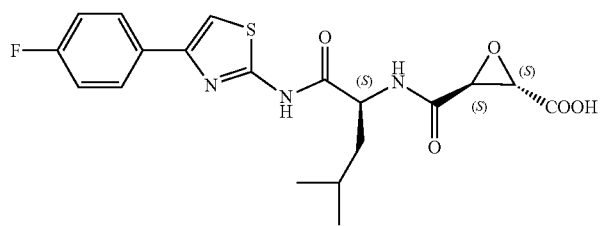
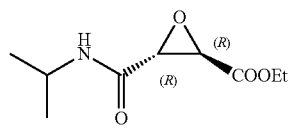
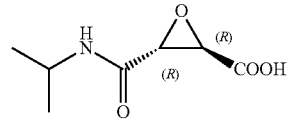
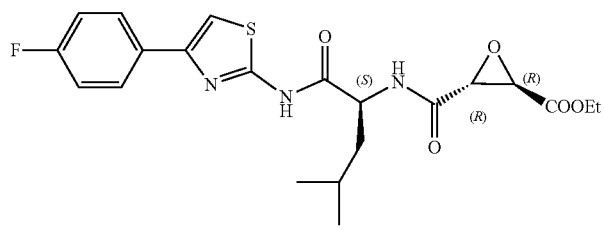
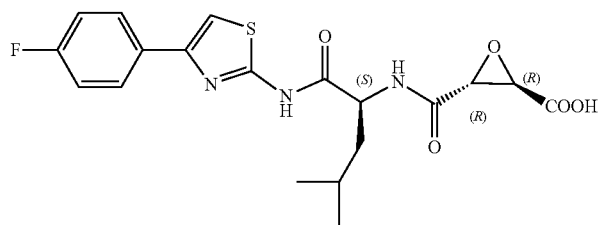
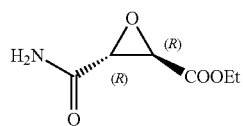
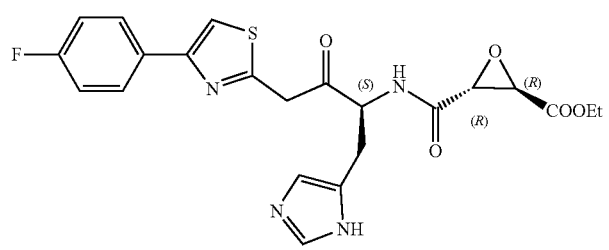
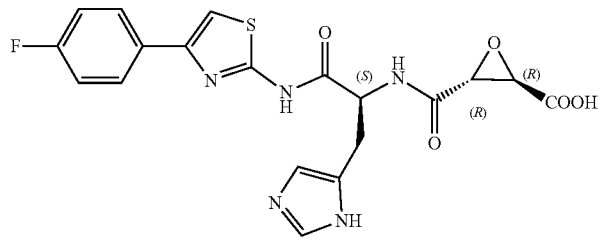
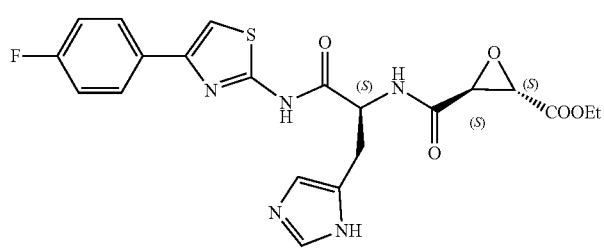

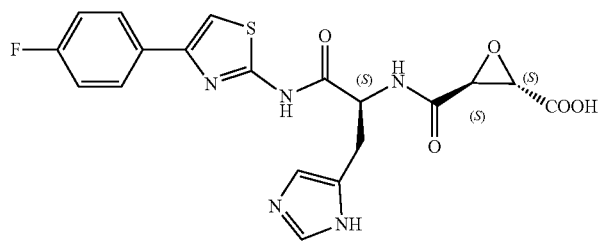
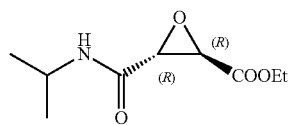
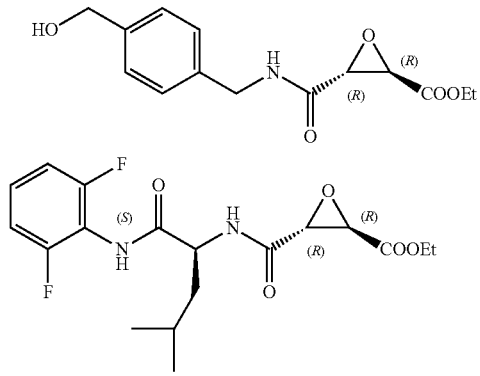
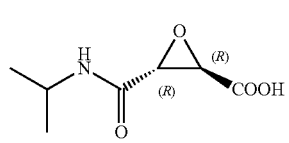
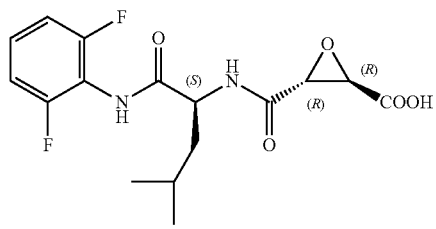
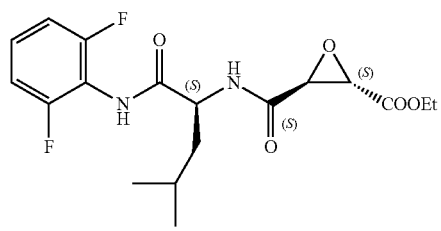
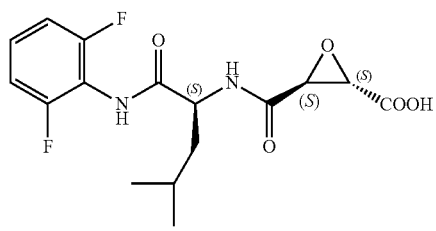
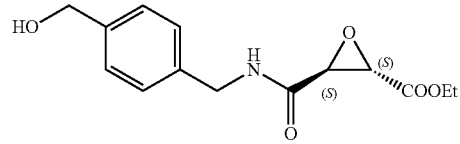
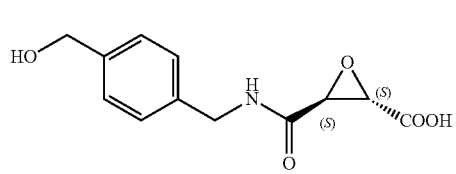
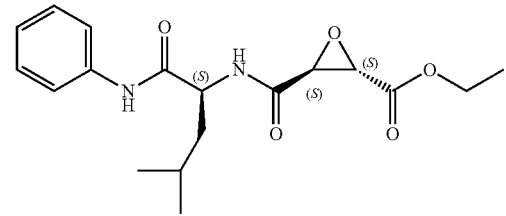
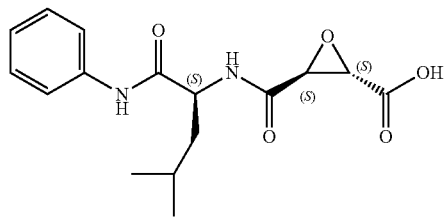
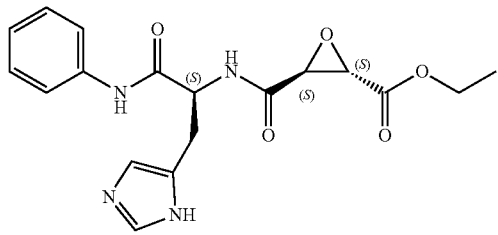

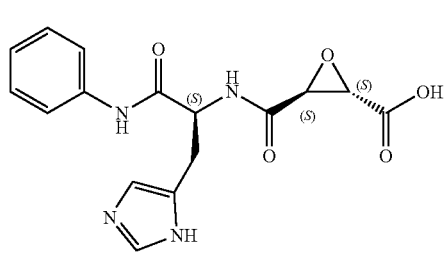
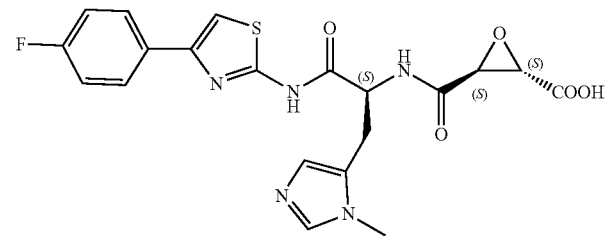
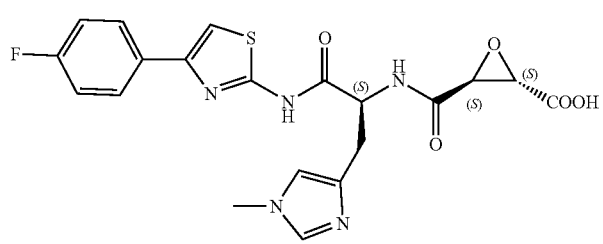
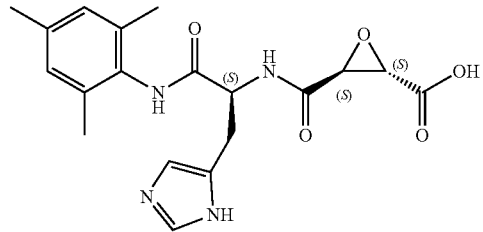
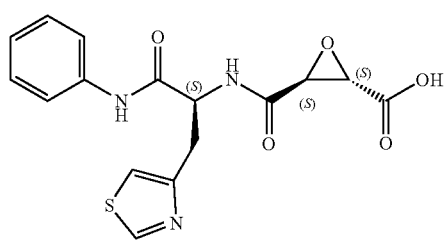
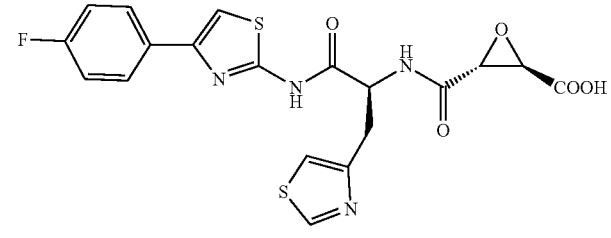
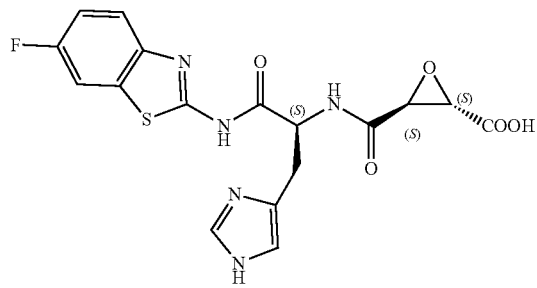
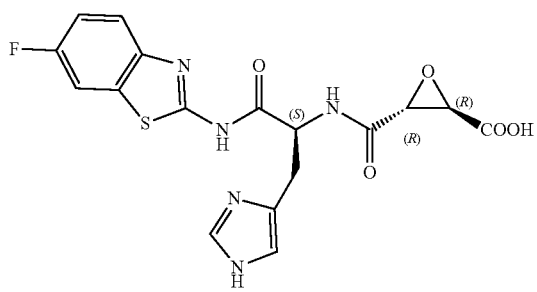
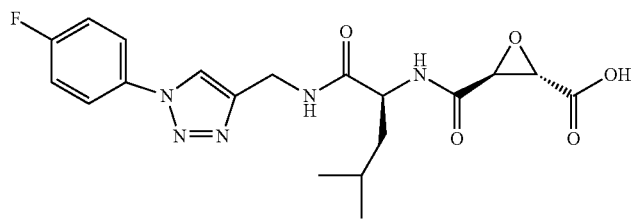
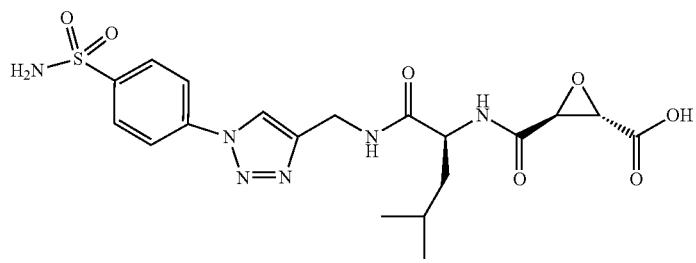

35
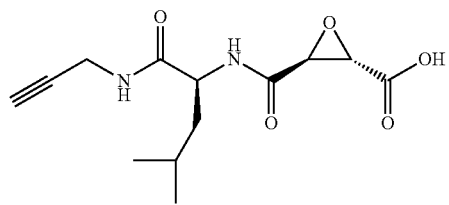
36
-continued
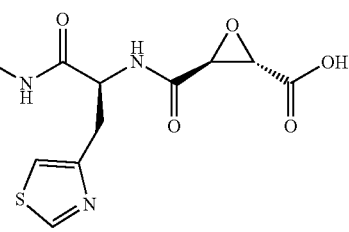
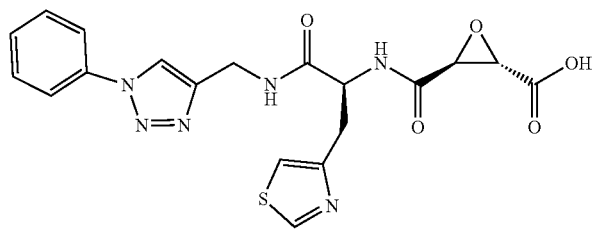
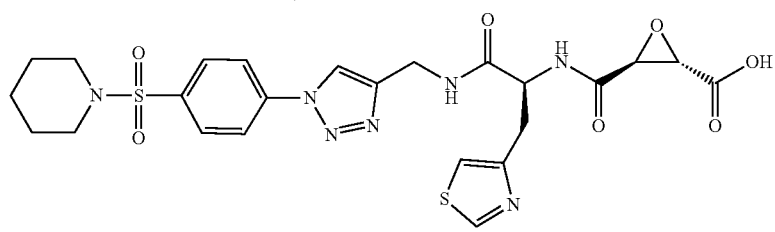
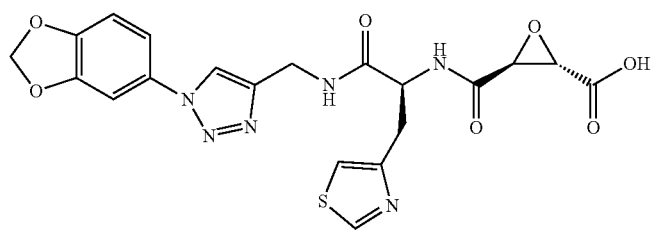
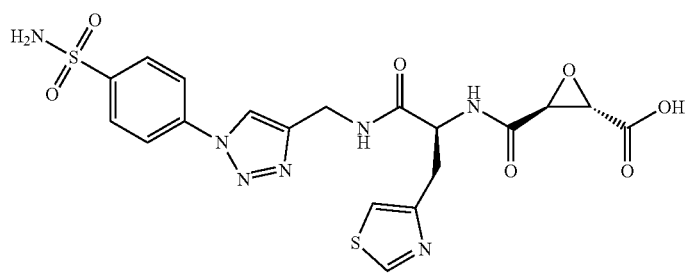
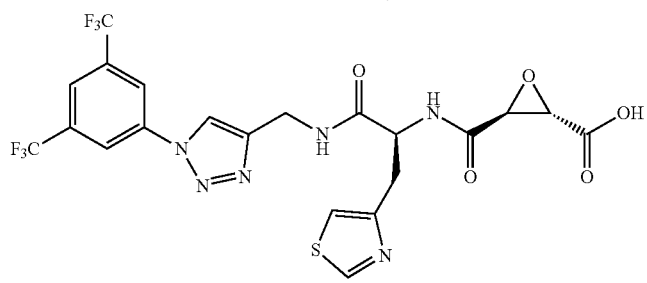
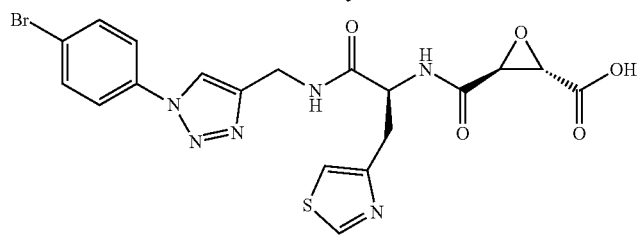

-continued

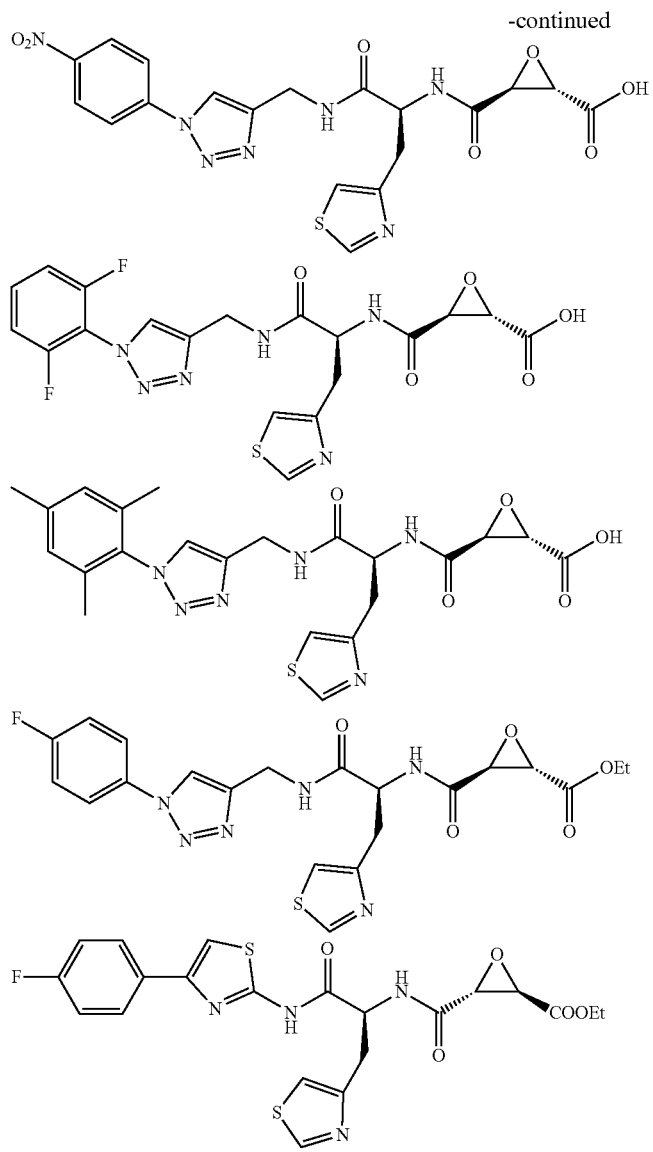

In some embodiments, the compounds of the invention exhibit inhibition of a cysteine protease with an $IC_{50}$ less than about 1 µM. In some embodiments, the $IC_{50}$ is less than about 500 nM. In some embodiments, the $IC_{50}$ is less than about 250 nM, less than about 100 nM, less than about 50 nM, less than about 25 nM, less than about 10 nM, less than about 5 nM, or less than about 1 nM.

In some embodiments, the compounds of formula (I) are selective inhibitors of cysteine proteases. In some embodiments, the compounds inhibit calpain.

It will recognized that one or more features of any embodiments disclosed herein may be combined and/or rearranged within the scope of the invention to produce further embodiments that are also within the scope of the invention. Those skilled in the art will recognize, or be able to ascertain using no more than routine experimentation, many equivalents to the specific embodiments of the invention described herein. Such equivalents are intended to be within the scope of the present invention.

The invention is further described by the following non-limiting Examples.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are illustrative only, since alternative methods can be utilized to obtain similar results.

Example 1: Selection of Epoxides

Several novel compounds were initially synthesized and observed to be stable towards reaction with free thiols and to provide Cal 1 inhibitors with sub-micromolar potency. A set of 45 epoxides was synthesized and assayed for inhibition of Cal1 (to select compounds with an $IC_{50}$<100 nM). The primary goal at this stage was to provide training set data for parameterization and correlation of computational methods. The P2 recognition group is important for the selectivity towards Cal1 vs. CathB. Therefore, modifications in the P3 recognition group were used to permit diversification. As a final refinement of the 3$^{rd}$ generation of inhibitors, a synthesis was developed to allow diversification of the P3 recognition group using click chemistry. Several compounds were screened in silico using a combination of docking scores to multiple Ca1 crystal structures and a geometric parameter associated with the transition state for covalent modification. This QSAR analysis gave Nsig values, from which inhibitors were selected for synthesis and enzyme assay. Compounds predicted to be poor inhibitors yielded high IC$_{50}$ values, whereas 4 of the 5 compounds with high Nsig values were sub-micromolar inhibitors.

Example 2: Synthetic Methods

Unless stated otherwise, all reactions were carried out under an atmosphere of dry argon in oven-dried glassware. Indicated reaction temperatures refer to those of the reaction bath, while room temperature (rt) is noted as 25° C. Dichloromethane (CH$_2$Cl$_2$) was distilled over CaH$_2$, and THF distilled over Na(s). All other solvents were of anhydrous quality purchased from Aldrich Chemical Co. and used as received. Pure reaction products were typically dried under high vacuum in the presence of phosphorus pentoxide. Commercially available starting materials and reagents were purchased from Aldrich, TCI and Fisher Scientific and were used as received unless specified otherwise. Analytical thin layer chromatography (TLC) was performed with (5×20 cm, 60 Å, 250 µm). Visualization was accomplished using a 254 nm UV lamp. $^1$H and $^{13}$C NMR spectra were recorded on either a Bruker Avance 400 MHz spectrometer or Bruker DPX 400 MHz spectrophotometer. Chemical shifts are reported in ppm with the solvent resonance as internal standard ([CDCl$_3$ 7.27 ppm, 77.23 ppm] [DMSO-d$_6$ 2.5 ppm, 39.51 ppm] and [MeOD-d$_4$ 4.78, 49.0] for $^1$H, $^{13}$C respectively). Data are reported as follows: chemical shift, multiplicity (s=singlet, d=doublet, dd=doublet of doublet, t=triplet, q=quartet, br=broad, m=multiplet, abq=ab quartet), number of protons, and coupling constants. Low-resolution mass spectra (LRMS) were acquired on an Agilent 6300 Ion-Trap LC/MS. High resolution mass spectral data was collected in-house using a Shimadzu QTOF 6500. All compounds submitted for biological testing were confirmed to be >95% pure by analytical HPLC.

Coupling of Arylamines to N-Protected Peptidomimetics.

A round bottom was charged with the appropriate Boc-protected carboxylic acid (1.0 eq) dissolved in minimal DMF (~3 ml/mmol) under argon and maintained at 0° C. EDCI (1.2 eq) was then added in one portion and the suspension stirred until homogenous (typically <5 min), followed by the addition of HOBt (1.5 eq). After stirring for an additional 15 min, the amine (1.0 eq) in DMF (~2 ml/mmol) was added dropwise, and the reaction allowed to warm to r.t., monitored by TLC. In instances when the amine remained on TLC after 8 h, reaction was again brought to 0° C., and additional EDCI (0.5 eq) was added, followed by stirring for an additional 4 h. Reaction was acidified to pH ~4 with 1 N HCl, extracted CH$_2$Cl$_2$ (3×). Combined organic extracts were washed with 1 N HCl (2×), and brine (1×), dried over Na$_2$SO$_4$, concentrated in vacuo, and purified by column chromatography to give the desired peptidomimetic scaffolds.

Epoxide Synthesis.

General Procedure for Large Scale Production of the Bromohydrin (2a & 2b).

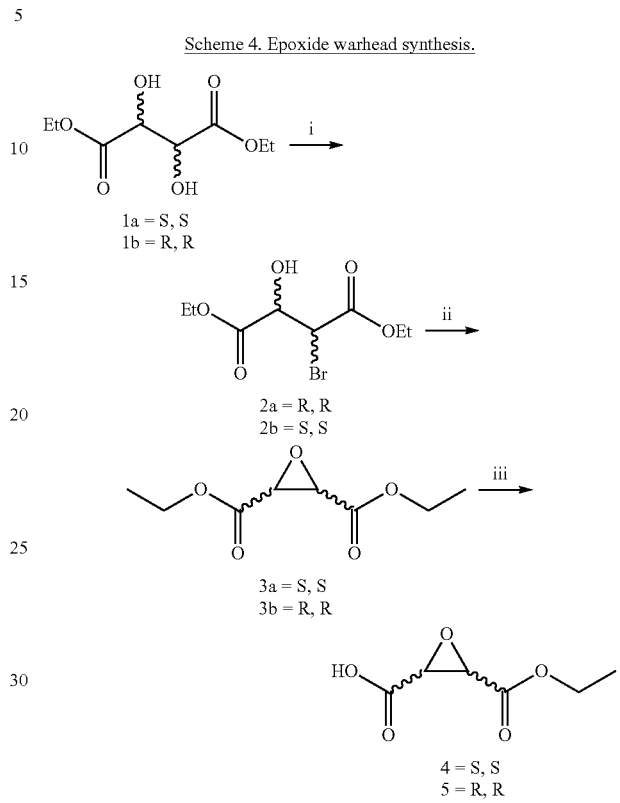

Scheme 4. Epoxide warhead synthesis.

Reagents: i) HBr (33%) in acetic acid, r.t, 12 h, then acetyl chloride, reflux, 12 h, 75-80%; ii) DBU, Et$_2$O, 0° C., 12 h, 70-80%; iii) Ethanolic KOH, 0° C., 6 h, 75-85%.

HBr (33% in acetic acid, 175 ml, 970 mmol) was added dropwise to D-DET (50 g, 242 mmol) at 0° C. over 1 h, and the reaction allowed to warm to r.t. and stirred for 12 h (Scheme 4). The reaction mixture was then poured into ice (~500 g), and the resulting aqueous layer extracted with Et$_2$O (4×200 ml). The combined organic extracts were then washed with H$_2$O (2×300 ml), brine (2×200 ml), dried over Na$_2$SO$_4$ and concentrated under reduced pressure. The resulting pale yellow oil was dissolved in anhydrous EtOH (300 mL) and acetyl chloride (8 ml, 242 mmol) was added dropwise. The solution was heated under gentle reflux for 7 h, cooled to r.t., and concentrated under reduced pressure to give yellow oil. The crude product was purified by under reduced pressure by fractional vacuum distillation to afford the desired bromohydrins as clear colorless oils (2a, 54.0 g, 99.1%; 2b, 51.2 g, 94.0%).

(2R,3R)-diethyl 2-bromo-3-hydroxysuccinate (2a). $^1$H NMR (CDCl$_3$, 400 MHz): δ 4.73-4.72 (d, 1H, 4.0 Hz); 4.69-4.68 (bt, 1H); 4.34-4.24 (m, 4H); 3.43-3.41 (d, 1H, J=7.2 Hz); 1.35-1.31 (t, 6H, J=14.4 Hz). $^{13}$C NMR (CDCl$_3$, 100 MHz): 170.27, 166.62, 72.51, 62.84, 62.62, 47.70, 14.03, 13.92.

(2S,3S)-diethyl 2-bromo-3-hydroxysuccinate (2b). $^1$H NMR (CDCl$_3$, 400 MHz): δ 4.73-4.72 (d, 1H, 4.0 Hz); 4.69-4.68 (bt, 1H); 4.34-4.24 (m, 4H); 3.43-3.41 (d, 1H, J=7.2 Hz); 1.35-1.31 (t, 6H, J=14.4 Hz). $^{13}$C NMR (CDCl$_3$, 100 MHz): 170.27, 166.62, 72.51, 62.84, 62.62, 47.70, 14.03, 13.92.

(2S,3S)-diethyl oxirane-2,3-dicarboxylate (3a). 2a (38.1 g, 142 mmol) was dissolved in anhydrous Et$_2$O (100 ml) and DBU (32.3 g, 212.4 mmol, in Et$_2$O [50 ml]) was added dropwise at 0° C. for 1 h. The reaction was allowed to warm to r.t. and stirred for an additional 4 h. Reaction was quenched with cold 1N HCl to pH ~5. The resulting aqueous layer was extracted with Et$_2$O (3×150 ml). The combined organic extracts were washed with brine (2×100 ml), dried over Na$_2$SO$_4$, and concentrated to give the pure product as faintly yellow oil (21.5 g, 80.7% yield). Product purity typically reflects that of the bromohydrin starting material. If necessary, fractional vacuum distillation can be used for purification. $^1$H NMR (CDCl$_3$, 400 MHz): δ 4.36-4.22 (m, 4H); 3.67 (s, 2H); 1.35-1.31 (t, 6H). $^{13}$C NMR (CDCl$_3$, 100 MHz): 166.75, 62.21, 52.01, 14.01.

(2R,3R)-diethyl oxirane-2,3-dicarboxylate (3b). Followed general procedure for 3a using the following quantities: 2b (34.6 g, 129 mmol); Et$_2$O (100 ml); DBU (29.4 g, 193 mmol, in Et$_2$O [50 ml]); yielded 3b as a colorless oil (18.1 g, 74.8%). $^1$H NMR (CDCl$_3$, 400 MHz): δ 4.36-4.22 (m, 4H); 3.67 (s, 2H); 1.35-1.31 (t, 6H). $^{13}$C NMR (CDCl$_3$, 100 MHz): 166.75, 62.21, 52.01, 14.01.

(2S,3S)-3-(ethoxycarbonyl)oxirane-2-carboxylic acid (4). An ethanolic solution of KOH (4.2 g, 64 mmol, in EtOH [50 ml]) was added dropwise to the 3a (9.7 g, 63 mmol) in EtOH (20 ml) at 0° C. for 30 min, and then the reaction was continued at r.t. for 8 h. The resulting viscous solution was diluted with ice water (150 ml), extracted with EA (2×200 ml). The aqueous layer was acidified with 1N HCl to pH-4, and extracted with EA (3×150 ml). Combined organic extracts washed with brine (2×50 ml), dried over Na$_2$SO$_4$, and concentrated to afford the pure epoxide monoester 4 as colorless oil (8.9 g, 86.9%). $^1$H NMR (CDCl$_3$, 400 MHz): δ 7.57 (br, 1H); 4.35-4.24 (m, 2H); 3.73 (s, 1H); 3.72 (s, 1H); 1.36-1.32 (t, 3H). $^{13}$C NMR (CDCl$_3$, 100 MHz): 171.61, 166.40, 62.45, 52.20, 51.45, 13.89.

(2R,3R)-3-(ethoxycarbonyl)oxirane-2-carboxylic acid (5). Followed general procedure for 4 using the following quantities: 3b (15.2 g, 81 mmol); KOH (4.53 g, 81 mmol, in EtOH [50 ml]); yielded 5 as a colorless oil (9.5 g, 73.5%). $^1$H NMR (CDCl$_3$, 400 MHz): δ 7.57 (br, 1H); 4.35-4.24 (m, 2H); 3.73 (s, 1H); 3.72 (s, 1H); 1.36-1.32 (t, 3H). $^{13}$C NMR (CDCl$_3$, 100 MHz): 171.61, 166.40, 62.45, 52.20, 51.45, 13.89.

Synthesis was directed at generation of a library of peptidomimetic epoxides possessing either natural or non-natural peptidomimetic residues at the P2 position, designated the R$_1$ substituent, and varying the P3/P4 cap groups, designated as R$_2$ in Scheme 5.

Scheme 5. Synthesis of Peptidomimetic Epoxides.

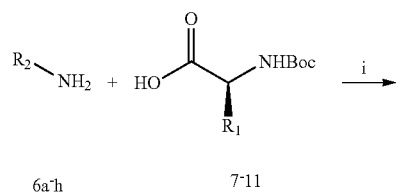

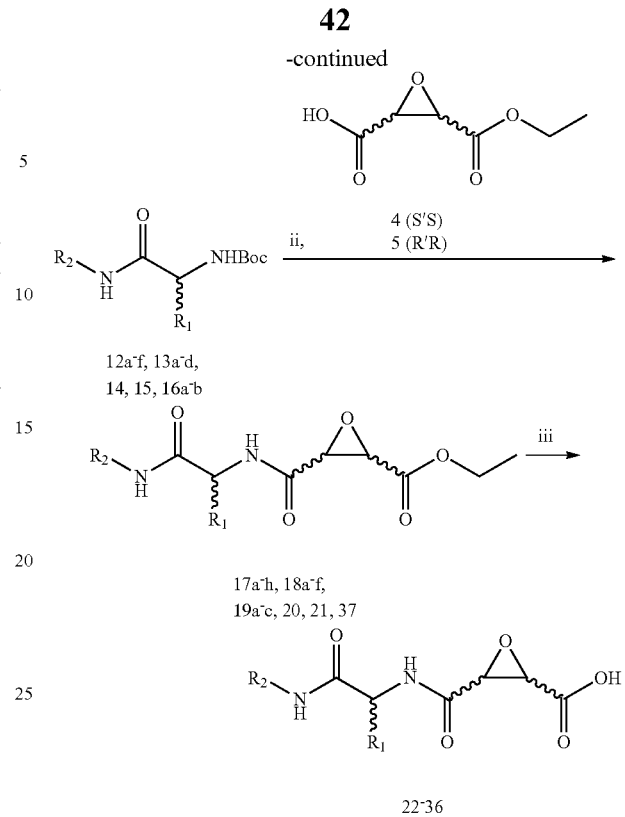

Regents:
i) EDCI, HOBT, DIPEA, CH$_2$Cl$_2$, 0° C.;
ii) EDCI, HOBT, DIPEA, DMF, 0° C.;
iii) LiOH, THF/MeOH, H$_2$O, 0° C.

Initially, the R$_2$-amines were coupled to the commercially available Boc-protected amino acids following typical peptide coupling procedures using either, HOBT and EDCI, or in the presence of CDI to give the corresponding Boc-protected peptidomimetic scaffolds (12-16) (Scheme 5). The epoxysuccinate moiety was synthesized in 3 steps starting from either L-DET or D-DET following published procedures to yield the unambiguous epoxysuccinate R,R (4) and S,S (5), respectively (Saito, S. et al., *Organic Syntheses* 1996, 73, 184; herein incorporated by reference in its entirety). Following TFA deprotection, the appropriate peptidomimetic scaffold was coupled to 4 or 5 using EDCI and HOBT in the presence of DIPEA to give the corresponding epoxide esters (17-21 and 37). Ester saponification using LiOH at 0° C. afforded the analogous epoxy acids 22-36 (Table 3). In four instances (30a, b and 31a, b), histidine containing analogs were found to be diastereomeric mixtures (L/D, S, S) and (L/D, R,R) resulting from racemization of the peptidyl α-carbon during the initial peptide coupling using CDI.

A possible occurrence in the synthesis of epoxide incorporating inhibitors is the propensity of the epoxide to undergo ring-opening. Hence, convergent synthesis is commonly utilized and the epoxide functionality is incorporated after derivatization has taken place, although a divergent synthetic approach is preferred for library development during lead optimization (Scheme 2).

Coupling of the Epoxide Monoester with the Peptidomimetic Amine.

TFA (10 eq) was added to a suspension of the BOC-protected peptidomimetic (1 eq) in freshly distilled CH$_2$Cl$_2$ (10 ml/1 mmol peptidomimetic) at 0° C. and the reaction mixture stirred at the same temperature for 6 h. If needed, additional TFA (5 eq) was added at 0° C. every 30 min until no starting material remained on TLC. The reaction was then concentrated under vacuo and the residual TFA-salt was dissolved in MeOH/H$_2$O and brought to pH of ~7 using a sat. NaHCO$_3$ solution, followed by extraction with CH$_2$Cl$_2$ (3×50 ml) and removal of solvent in vacuo to afford the pure free amine, which was dried under high vacuum and used in the next reaction without further purification. A round bottom was charged with the epoxide monoacid (1.0 eq) dissolved in minimal DMF (~2 ml/mmol) with DIPEA (1.1 eq) under argon and maintained at 0° C. EDCI (1.0 eq) was then added in one portion and the suspension stirred until homogenous (typically <5 min), followed by the addition of HOBt (1.2 eq). After stirring for an additional 15 min, the free amine (1.0 eq) in DMF (~3 ml/mmol) was added dropwise, and the reaction allowed to warm to room temperature, monitored by TLC. After 12 h, the reaction was quenched acidified to pH ~4 with 1 N HCl, extracted CH$_2$Cl$_2$ (3×). Combined organic extracts were washed with 1 N HCl (2×), and brine (1×), dried over Na$_2$SO$_4$, concentrated in vacuo, and purified by column chromatography to give the desired peptidomimetic scaffolds.

Alternative Procedure for Coupling of the Epoxide Monoester with the Peptidomimetic Amine.

TFA (10 eq) was added to a suspension of the BOC-protected peptidomimetic (1eq) in CH$_2$Cl$_2$ (20 ml/1 mmol peptidomimetic) at 0° C. and the reaction mixture stirred at the same temperature for 2 h. Excess TFA and CH$_2$Cl$_2$ were removed under vacuum and the residual TFA-salt was either dried under high vacuum and subjected to next reaction without further purification, or dissolved in MeOH/H$_2$O and brought to pH of ~7 using a saturated NaHCO$_3$ solution, followed by extraction with CH$_2$Cl$_2$ (3×50 ml) and removal of solvent in vacuo to afford the pure free amine, which was used without further purification. The intermediate deprotected amine (1 eq), the epoxide monoester (1 eq), and HOBt (1.1 eq) were dissolved in minimal DMF and then DIPEA (1 mL, 5.6 mmol) and EDCI (326 mg, 1.7 mmol) were added. After stirring at ambient temperature for 12 h water was added to the reaction mixture and diluted with 200 mL of CH$_2$Cl$_2$. The organic layer was separated and washed with 1M HCl (20 mL), saturated NaHCO$_3$ solution (10 mL), water (30 mL), brine (10 mL), and dried over anhydrous Na$_2$SO$_4$ and concentrated in vacuo. Chromatographic purification of the crude mixture gave the title compounds.

Coupling of the Epoxide Monoester with the Peptidomimetic Amine.

Boc-deprotection: TFA (10 eq) was added to a suspension of the appropriate Boc-protected peptidomimetic (1 eq) in freshly distilled CH$_2$Cl$_2$ (10 ml/1 mmol peptidomimetic) at 0° C. and the reaction mixture stirred at the same temperature for 6 h. If needed, additional TFA (5 eq) was added at 0° C. every 30 min until no starting material remained on TLC. The reaction was then concentrated under vacuum and the residual TFA-salt was dissolved in MeOH/H$_2$O and brought to pH of ~7 using a sat. NaHCO$_3$ solution, followed by extraction with CH$_2$Cl$_2$ (3×50 ml) and removal of solvent in vacuo to afford the pure free amine, which was dried under high vacuum and used in the next reaction without further purification.

Coupling: A round bottom was charged with the appropriate epoxide monoacid (1.0 eq) dissolved in minimal DMF (~2 ml/mmol) with DIPEA (1.1 eq) under argon and maintained at 0° C. EDCI (1.0 eq) was then added in one portion and the suspension stirred until homogenous (typically <5 min), followed by the addition of HOBt (1.2 eq). After stirring for an additional 15 min, the free amine (1.0 eq) in DMF (~3 ml/mmol) was added dropwise, and the reaction allowed to warm to room temperature, monitored by TLC. After 12 h, the reaction was quenched acidified to pH ~4 with 1 N HCl, extracted with CH$_2$Cl$_2$ (3×). Combined organic extracts were washed with 1 N HCl (2×), and brine (1×), dried over Na$_2$SO$_4$, concentrated in vacuo, and purified by column chromatography to give the desired peptidomimetic scaffolds.

Peptidomimetic-Epoxide Ester Saponification.

The peptidomimetic epoxide ester (1 eq) was dissolved in THF/MeOH/H$_2$O (3:1:1) and cooled to 0° C. and LiOH (1 eq) was added and reaction allowed to warm to r.t. Additional LiOH (0.2 eq) was added at 0° C. every 3 h as needed until no starting material remained on TLC. The resulting solution was acidified with cold 1 N HCl and poured into CH$_2$Cl$_2$. In some cases the acid precipitated out and was filtered through sintered funnel and washed consecutively with CH$_2$Cl$_2$ and H$_2$O and isolated. In instances when the compound stayed in solution, the aqueous phase was extracted with CH$_2$Cl$_2$ (3×50 ml), combined organic extracts dried over Na$_2$SO$_4$ and concentrated to give the desired product. Typically, the purity of the desired product reflects the purity of the ester starting material. It was found that having sufficiently pure ester starting material is essential to afford a pure acid upon hydrolysis.

TABLE 1

Structure designations for epoxide esters 17-21, and 37.

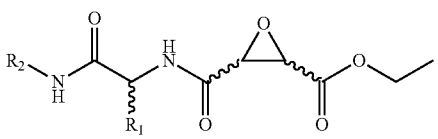

17a-h, 18a-f, 19a-c, 20, 21, 37

| Compound | R$_1$ | R$_2$ | Stereochemistry |
| --- | --- | --- | --- |
| 17a | L-Leucine | Phenyl | S,S,S |
| 17b | L-Leucine | 2,6 difluorophenyl | S,S,S |
| 17c | L-Leucine | 2,6 difluorophenyl | S,R,R |
| 17d | L-Leucine | 4-(4-Fluorophenyl)thiazol-2-amine | S,S,S |
| 17e | L-Leucine | 4-(4-Fluorophenyl)thiazol-2-amine | S,R,R |
| 17f | L-Leucine | 4-F-Phenyl-SO$_2$—NH—(CH$_2$)$_4$—NH$_2$ | S,S,S |

TABLE 1-continued

Structure designations for epoxide esters 17-21, and 37.

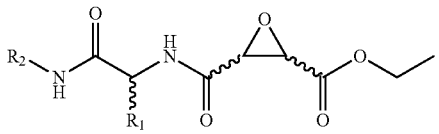

17a-h, 18a-f, 19a-c, 20, 21, 37

| Compound | R1 | R2 | Stereochemistry |
| --- | --- | --- | --- |
| 17g | L-Leucine | Lipoyl-NH—(CH$_2$)$_4$—NH$_2$ | S,S,S |
| 17h | L-Leucine | D-Biotin-NH—(CH$_2$)$_4$—NH$_2$ | S,S,S |
| 18a | L-Histidine | Phenyl | S,S,S |
| 18b | L-Histidine | 1,3,5 trimethylaniline | S,S,S |
| 18c | L-Histidine | 4-(4-Fluorophenyl)thiazol-2-amine | S/R,S,S |
| 18d | L-Histidine | 4-(4-Fluorophenyl)thiazol-2-amine | S/R,R,R |
| 18e | L-Histidine | 6-fluorobenzo[d]thiazol-2-amine | S/R,S,S |
| 18f | L-Histidine | 6-fluorobenzo[d]thiazol-2-amine | S/R,R,R |
| 19a | L-Ala(4-thiazoyl)-OH | Phenyl | S,S,S |
| 19b | L-Ala(4-thiazoyl)-OH | 4-(4-Fluorophenyl)thiazol-2-amine | S,S,S |
| 19c | L-Ala(4-thiazoyl)-OH | 4-(4-Ethynyl)thiazol-2-amine | S,S,S |
| 20 | L-His(2-Me)—OH | 4-(4-Fluorophenyl)thiazol-2-amine | S,S,S |
| 21 | L-His(4-Me)—OH | 4-(4-Fluorophenyl)thiazol-2-amine | S,S,S |
| 37 | L-Ala(4-thiazoyl)-H | Propargylamine | S,S,S |

(2S,3S)-ethyl-3-((S)-4-methyl-1-oxo-1-(phenylamino)pentan-2-ylcarbamoyl)oxirane-2-carboxylate (17a)

General procedure using: Boc-protected peptidomimetic (570 mg, 1.1 mmol); (2S,3S)-epoxysuccinic acid monoester (126 mg, 0.93 mmol), DIPEA (0.16 mL, 0.93 mmol), and HOBT (126 mg, 0.93 mmol) CH$_2$Cl$_2$ (10 ml)/DMF (2 ml); EDCI (220 mg, 1.1 mmol) in DMF (1 mL) gave the title compound (100 mg, 30.6%) as white solid. $^1$H NMR (CDCl$_3$, 400 MHz): δ 7.57-7.55 (d, 2H, J=7.67 Hz); 7.34-7.30 (t, 2H); 7.13-7.10 (t, 1H); 4.63-4.61 (m, 1H); 4.30-4.24 (m, 2H); 3.729-3.725 (d, 1H, J=1.67 Hz); 3.62-3.61 (d, 1H, J=1.72 Hz); 1.76-1.63 (m, 3H); 1.33-1.29 (t, 3H); 1.02-1.00 (t, 6H). $^{13}$C NMR (CDCl$_3$, 100 MHz): 171.22, 169.07, 167.15, 137.98, 128.41, 124.12, 120.14, 52.90, 52.58, 52.50, 51.70, 40.70, 29.50, 24.65, 22.04, 20.60.

(2S,3S)-ethyl-3-((S)-1-(2,6-difluorophenylamino)-4-methyl-1-oxopentan-2-ylcarbamoyl)oxirane-2-carboxylate (17b)

General procedure using: Boc-protected peptidomimetic (600 mg, 1.7 mmol); (2S,3S)-epoxysuccinic acid monoester (280 mg, 1.7 mmol), DIPEA (0.45 mL, 2.6 mmol), in CH$_2$Cl$_2$ (10 ml)/DMF (5 ml); EDCI (280 mg, 1.7 mmol) in DMF (1 mL) gave the title compound (210 mg, 31.6%) as white solid. $^1$H NMR (400 MHz, CDCl$_3$): δ 8.20 (s, 1H); 7.18-7.16 (t, 1H); 6.94-6.90 (t, 2H); 6.72-6.70 (d, 1H); 4.86-4.85 (q, 1H); 4.29-4.23 (m, 2H); 3.83-3.80 (d, 1H, J=1.69 Hz); 3.72-3.55 (d, 1H, J=1.69 Hz); 1.84-1.70 (m, 3H); 1.30-1.26 (t, 3H); 1.01-0.99 (d, 6H). $^{13}$C NMR (DMSO-d$_6$, 100 MHz): 170.10, 166.5, 166.39, 158.92, 156.46, 127.73, 111.88, 111.54, 164.9, 62.27, 53.9, 52.9, 51.01, 41.2, 24.74, 22.5, 14.0.

(2R,3R)-ethyl-3-((S)-1-(2,6-difluorophenylamino)-4-methyl-1-oxopentan-2-ylcarbamoyl)oxirane-2-carboxylate (17c)

General procedure using: Boc-protected peptidomimetic (550 mg, 1.6 mmol); (2S,3S)-epoxysuccinic acid monoester (250 mg, 1.6 mmol), DIPEA (0.65 mL, 3.8 mmol), and HOBT (250 mg, 1.9 mmol) in CH$_2$Cl$_2$ (15 ml)/DMF (5 ml); EDCI (300 mg, 2.0 mmol) in DMF (1 mL) gave the title compound (25 mg, 41.6%) as white solid. $^1$H NMR (400 MHz, CDCl$_3$): δ 8.20 (s, 1H); 7.19-7.17 (t, 1H); 6.94-6.90 (t, 2H); 6.72-6.70 (d, 1H); 4.86-4.85 (q, 1H); 4.31-4.25 (m, 2H); 3.84-3.81 (d, 1H, J=1.69 Hz); 3.73-3.56 (d, 1H, J=1.69 Hz); 1.84-1.69 (m, 3H); 1.32-1.28 (t, 3H); 1.02-1.00 (d, 6H). $^{13}$C NMR (CDCl$_3$, 100 MHz): 170.10, 166.67, 166.39, 158.92, 156.46, 127.73, 111.78, 111.54, 62.28, 53.67, 52.69, 51.21, 40.81, 24.74, 22.74, 22.11, 13.97.

(2S,3S)-ethyl-3-((S)-1-(4-(4-fluorophenyl)thiazol-2-ylamino)-4-methyl-1-oxopentan-2-ylcarbamoyl)oxirane-2-carboxylate (17d)

General procedure using: Boc-protected peptidomimetic (410 mg, 1.0 mmol); (2S,3S)-epoxysuccinic acid monoester (160 mg, 1.0 mmol), DIPEA (0.18 mL, 1.0 mmol), and HOBT (163 mg, 1.2 mmol) in CH$_2$Cl$_2$ (10 ml); EDCI (211 mg, 1.1 mmol) in DMF (0.5 mL) gave the title compound (203 mg, 40.1%) as white solid. $^1$H NMR (400 MHz, CDCl$_3$): δ 9.96 (s, 1H); 7.79-7.76 (q, 2H); 7.11-7.07 (m, 3H); 6.57-6.55 (d, 1H, J=8.4 Hz); 4.80-4.78 (1, 1H); 4.29-4.23 (m, 2H); 3.868-3.864 (d, 1H, J=1.60 Hz); 3.522-3.581 (d, 1H, J=1.60 Hz); 1.86-1.81 (m, 1H); 1.66-1.61 (m, 2H); 1.28-1.24 (m, 4H); 0.98-0.94 (t, 6H). $^{13}$C NMR (DMSO-d$_6$, 100 MHz): 170.28, 167.48, 165.78, 163.43, 161.00, 158.23, 148.34, 135.36, 131.32, 128.17, 116.13, 108.52, 62.01, 53.71, 53.36, 51.82, 14.33. ESI-LRMS (m/z): [M+H]$^+$=450.

(2R,3R)-ethyl-3-((S)-1-(4-(4-fluorophenyl)thiazol-2-ylamino)-4-methyl-1-oxopentan-2-ylcarbamoyl)oxirane-2-carboxylate (17e)

General procedure using: Boc-protected peptidomimetic (290 mg, 0.71 mmol); (2S,3S)-epoxysuccinic acid monoester (113 mg, 0.71 mmol), DIPEA (0.13 mL, 0.71 mmol), and HOBT (115 mg, 0.85 mmol) in DMF (3 ml); EDCI (150 mg, 0.78 mmol) in DMF (0.5 mL) gave the title compound (100 mg, 31.5%) as white solid. $^1$H NMR (400

MHz, CDCl₃): δ 9.96 (s, 1H); 7.79-7.76 (q, 2H); 7.11-7.06 (m, 3H); 6.48-6.46 (d, 1H, J=8.4 Hz); 4.71-4.69 (1, 1H); 4.25-4.22 (m, 2H); 3.78-3.77 (d, 1H, J=1.20 Hz); 3.60-3.59 (d, 1H, J=1.20 Hz); 1.86-1.81 (m, 1H); 1.71-1.60 (m, 2H); 1.30-1.25 (m, 4H); 0.98-0.96 (t, 6H). ¹³C NMR (DMSO-d₆, 100 MHz): 170.24, 167.46, 165.58, 163.43, 161.00, 158.20, 148.34, 135.36, 131.29, 128.09, 115.92, 108.52, 62.01, 53.52, 53.41, 51.85, 14.33. ESI-LRMS (m/z): [M+H]⁺=450.

(2S,3S)-ethyl-3-((S)-1-(4-(4-fluorophenylsulfonamido)butylamino)-4-methyl-1-oxopentan-2-ylcarbamoyl)oxirane-2-carboxylate (17f)

General procedure using: Boc-protected peptidomimetic (442 mg, 1.0 mmol); (2S,3S)-epoxysuccinic acid monoester (154.1 mg, 0.96 mmol), DIPEA (0.17 mL, 0.96 mmol), and HOBT (157 mg, 1.15 mmol) in DMF (5 ml); EDCI (203 mg, 1.05 mmol) in DMF (0.5 mL) gave the title compound (321 mg, 60.5%) as white solid. ¹H NMR (400 MHz, CDCl₃): δ 7.89-7.86 (m, 2H); 7.21-7.19 (t, 2H); 6.87-6.85 (d, 1H, J=8.40 Hz); 6.32 (bs, 1H); 5.25 (t, 1H); 4.27-4.25 (q, 1H); 4.22-4.19 (m, 2H); 3.71-3.70 (d, 1H. J=1.60 Hz); 3.48-3.47 (d, 1H, J=1.60 Hz); 3.28-3.12 (m, 2H); 2.95-2.93 (d, 2H); 1.62-1.45 (m, 9H); 1.33-1.30 (t, 3H); 0.94-0.90 (t, 6H). ¹³C NMR (CDCl₃, 100 MHz): 171.52, 166.67, 166.63, 166.51, 163.98, 130.01, 129.92, 116.66, 116.44, 62.65, 53.99, 53.23, 51.75, 42.98, 41.20, 39.15, 26.80, 26.63, 25.06, 23.06, 22.19, 14.25. ESI-LRMS (m/z): [M+H]⁺=502.

(2S,3S)-ethyl-3-((2S)-1-((5-(1,2-dithiolan-3-yl)pentanamido)methylamino)-4-methyl-1-oxopentan-2-ylcarbamoyl)oxirane-2-carboxylate (17g)

General procedure using: Boc-protected peptidomimetic (170 mg, 0.35 mmol); (2S,3S)-epoxysuccinic acid monoester (56 mg, 0.35 mmol), DIPEA (0.06 mL, 0.35 mmol), and HOBT (56 mg, 0.42 mmol) in DMF (2 ml); EDCI (73 mg, 1.2 mmol) in DMF (0.5 mL) gave the title compound (53 mg, 28%) as white solid. ¹H NMR (CDCl₃, 400 MHz): δ 7.23-7.21 (d, 1H, J=8.4 Hz); 7.18-7.15 (t, 1H); 6.33 (t, 1H); 4.51-4.49 (q, 1H); 4.28-4.24 (m, 2H); 3.717-3.713 (d, 1H, J=1.60 Hz); 3.60-3.57 (m, 1H); 3.524-3.520 (d, 1H, J=1.60 Hz); 3.18-3.11 (m, 7H); 2.47-2.45 (m, 1H); 2.22-2.18 (t, 2H); 1.93-1.90 (m, 1H); 1.67-1.52 (m, 15H); 1.33-1.30 (dd, 4H); 0.94-0.90 (t, 6H). ¹³C NMR (CDCl₃, 100 MHz): 173.66, 171.94, 167.13, 166.52, 62.85, 56.95, 56.92, 54.28, 53.28, 52.01, 41.89, 40.73, 40.10, 39.72, 39.40, 39.23, 38.94, 36.87, 35.07, 29.38, 29.36, 27.65, 27.50, 26.89, 26.27, 25.90, 25.32, 23.41, 22.48, 14.52. ESI-LRMS (m/z): [M+H]⁺=532.

(2S,3R)-ethyl-3-((S)-4-methyl-1-oxo-1-(4-(5-((3aS,4S,6aR)-2-oxohexahydro-1H-thieno[3,4-d]imidazol-4-yl)pentanamido)butylamino)pentan-2-ylcarbamoyl)oxirane-2-carboxylate (17h)

General procedure using: Boc-protected peptidomimetic (570 mg, 1.1 mmol); (2S,3S)-epoxysuccinic acid monoester (176 mg, 1.1 mmol), DIPEA (0.2 mL, 1.1 mmol), and HOBT (178 mg, 1.3 mmol) in DMF (5 ml); EDCI (232 mg, 1.2 mmol) in DMF (1 mL) gave the title compound (624 mg, 85%) as white solid. ¹H NMR (DMSO-d₆, 400 MHz): δ 8.62 (d, 1H); 8.08 (t, 1H); 7.74 (t, 1H); 6.42 (s, 1H); 6.36 (s, 1H); 4.31 (m, 2H); 4.18 (m, 3H); 3.71 (d, 1H); 3.59 (d, 1H); 3.12 (m, 1H); 3.01 (m, 4H); 2.92 (dd, 1H); 2.58 (d, 1H); 2.04 (t, 2H); 1.49 (m, 7H); 1.35 (m, 6H); 1.23 (t, 3H); 0.89 (d, 3H); 0.83 (d, 3H). ¹³C NMR (DMSO-d₆, 100 MHz): 171.7; 170.9; 167.1; 164.4; 162.6; 61.4; 60.9; 59.1; 55.3; 52.8; 51.1; 41.0; 38.2; 37.9; 35.1; 28.1; 27.9; 26.5; 26.4; 25.2; 24.1; 22.8; 21.5; 13.8. ESI-LRMS (m/z): [M+H]⁺=570.

(2S,3S)-ethyl-3-((S)-3-(1H-imidazol-5-yl)-1-oxo-1-(phenylamino)propan-2-ylcarbamoyl)oxirane-2-carboxylate (18a)

General procedure using: Boc-protected peptidomimetic (463 mg, 1.4 mmol); (2S,3S)-epoxysuccinic acid monoester (220 mg, 1.4 mmol), DIPEA (0.24 mL, 1.4 mmol), and HOBT (230 mg, 1.7 mmol) in DMF (5 ml); EDCI (300 mg, 1.5 mmol) in DMF (0.5 mL) gave the title compound (180 mg, 34.5%) as white solid. H NMR (400 MHz, MeOD-d⁴): δ 7.63 (s, 1H); 7.52-7.50 (d, 2H, J=7.72 Hz); 7.33-7.31 (t, 2H); 7.13-7.11 (t, 1H); 6.90 (s, 1H); 4.76-4.75 (t, 1H); 4.29-4.24 (q, 2H); 3.69-3.68 (d, 1H, J=1.56 Hz); 3.64-3.63 (d, 1H, J=1.56 Hz); 3.17-3.05 (qd, 2H); 1.33-1.29 (t, 3H). ¹³C NMR (MeOD-d⁴ 100 MHz): 169.75, 167.25, 166.90, 137.85, 134.98, 127.36, 124.19, 119.88, 61.73, 54.15, 52.90, 51.60, 12.88.

(2S,3S)-ethyl-3-((S)-3-(1H-imidazol-5-yl)-1-(mesitylamino)-1-oxopropan-2-ylcarbamoyl)oxirane-2-carboxylate (18b)

General procedure using: Boc-protected peptidomimetic (180 mg, 0.47 mmol); (2S,3S)-epoxysuccinic acid monoester (75 mg, 0.47 mmol), DIPEA (0.12 mL, 0.7 mmol), and HOBT (76 mg, 0.56 mmol) in DMF (5 ml); EDCI (99 mg, 0.52 mmol) in DMF (0.5 mL) gave the title compound (55 mg, 28.3%) as white solid. ¹H NMR (400 MHz, MeOD-d⁴): δ 7.66 (s, 1H); 6.96 (s, 1H); 6.88 (s, 1H); 4.27-4.25 (q, 2H); 3.68 (s, 1H); 3.32 (s, 1H); 3.21-3.07 (m, 2H); 2.25 (s, 3H); 2.06 (s, 6H); 1.32-1.29 (t, 3H). ¹³C NMR (MeOD): ¹³C NMR (MeOD-d⁴ 100 MHz): 167.22, 136.74, 135.14, 128.25, 61.74, 52.98, 51.80, 19.53, 16.77, 12.88. MS (ESI) m/z 415.2 (M+H)⁺.

(2S,3S)-ethyl-3-(1-(4-(4-fluorophenyl)thiazol-2-ylamino)-3-(1H-imidazol-4-yl)-1-oxopropan-2-ylcarbamoyl)oxirane-2-carboxylate (18c)

General procedure using: the racemic Boc-protected peptidomimetic (400 mg, 1.2 mmol); (2S,3S)-epoxysuccinic acid monoester (160 mg, 1.0 mmol), DIPEA (0.43 mL, 2.5 mmol) and HOBT (76 mg, 0.56 mmol) in DMF (5 ml); EDCI (210 mg, 1.1 mmol) in DMF (0.5 mL) gave the title compound (217 mg, 45.8%) as a racemic mixture in the form of a white solid. ¹H NMR (DMSO-d₆, 400 MHz): δ 12.50 (bs, 1H); 11.90 (bs, 1H); 8.85-8.76 (dd, 1H, J=7.14 Hz); 7.95-7.91 (q, 2H); 7.64-7.58 (m, 2H); 7.28-7.24 (t, 2H); 6.84 (bs, 1H); 4.79-4.75 (q, 1H); 4.22-4.18 (q, 2H); 3.74-3.73 (dd, 1H, J=1.80 Hz); 3.63-3.62 (dd, 1H; J=1.80 Hz); 3.17-3.08 (m, 2H); 1.25-1.21 (t, 3H). ¹³C NMR (DMSO-d₆, 100 MHz): 169.53, 168.87, 168.81, 165.98, 165.83, 162.89, 160.47, 157.65, 147.82, 134.58, 132.10, 127.64, 127.56, 116.40, 115.60, 115.40, 108.04, 52.98, 52.75, 51.90, 28.55, 28.42.

(2R,3R)-ethyl-3-(1-(4-(4-fluorophenyl)thiazol-2-ylamino)-3-(1H-imidazol-4-yl)-1-oxopropan-2-ylcarbamoyl)oxirane-2-carboxylate (18d)

General procedure using: the racemic Boc-protected peptidomimetic (400 mg, 1.0 mmol); (2S,3S)-epoxysuccinic acid monoester (149 mg, 0.93 mmol), DIPEA (0.16 mL, 0.93 mmol) and HOBT (151 mg, 1.1 mmol) in DMF (5 ml); EDCI (196 mg, 1.0 mmol) in DMF (0.5 mL) gave the title compound (240 mg, 50.8%) as a racemic mixture in the form of a white solid. $^1$H NMR (DMSO-d$_6$, 400 MHz): δ 12.52 (bs, 1H); 11.86 (bs, 1H); 8.85-8.77 (dd, J=7.21 Hz; J=7.48 Hz); 7.95-7.91 (q, 2H); 7.62 (s, 1H); 7.57 (s, 1H); 7.28-7.24 (t, 2H); 6.84 (s, 1H); 4.81-4.76 (m, 1H); 4.23-4.15 (m, 1H); 3.76-3.74 (dd, 1H, J=1.8 Hz; J=1.8 Hz); 3.64-3.61 (dd, 1H, J=1.8 Hz; J=1.8 Hz); 3.08-2.99 (m, 2H); 1.25-1.17 (t, 3H). $^{13}$C NMR (DMSO-d$_6$, 100 MHz): 170.28 & 170.24, 167.48 & 167.46, 165.78 & 165.58, 163.43, 161.01, 158.53 & 158.20, 135.37, 131.32 & 131.29, 128.17 & 128.09, 116.13 & 115.92, 108.52, 62.01, 53.72 & 53.52, 53.41 & 53.36, 51.85 & 51.82, 14.33.

(2S,3S)-ethyl-3-(1-(6-fluorobenzo[d]thiazol-2-ylamino)-3-(1H-imidazol-4-yl)-1-oxopropan-2-ylcarbamoyl)oxirane-2-carboxylate (18e)

General procedure using: the racemic Boc-protected peptidomimetic (402 mg, 0.99 mmol); (2S,3S)-epoxysuccinic acid monoester (159 mg, 0.99 mmol), DIPEA (0.18 mL, 0.99 mmol) and HOBT (161 mg, 1.18 mmol) in DMF (5 ml); EDCI (209 mg, 1.09 mmol) in DMF (0.5 mL) gave the title compound (229 mg, 51.5%) as a racemic mixture in the form of a white solid. $^1$H NMR (CDCl$_3$, 400 MHz): δ 7.96 (bs, 1H); 7.76-7.73 (m, 2H); 7.52-7.50 (d, 1H); 7.18-7.14 (m, 1H); 6.94 (s, 1H); 4.93 (bs, 1H); 4.32-4.27 (m, 2H); 3.78 (s, 1H); 3.63 (s, 1H); 3.26-3.22 (dd, 1H); 3.10-3.06 (dd, 1H); 1.36-1.32 (t, 3H). $^{13}$C NMR (CDCl$_3$, 100 MHz): 172.15, 168.52 & 168.50, 166.88 & 166.70, 161.31, 159.19 & 158.91, 146.53, 136.25, 134.04 & 133.93, 122.94 & 122.84, 115.55 & 115.30, 109.41 & 109.14, 62.40, 55.67, 54.20 & 53.98, 53.72 & 53.66, 52.17 & 52.12, 14.42.

(2R,3R)-ethyl-3-(1-(6-fluorobenzo[d]thiazol-2-ylamino)-3-(1H-imidazol-4-yl)-1-oxopropan-2-ylcarbamoyl)oxirane-2-carboxylate (18f)

General procedure using: Boc-protected peptidomimetic (420 mg, 1.0 mmol); (2S,3S)-epoxysuccinic acid monoester (162 mg, 1.01 mmol), DIPEA (0.18 mL, 1.01 mmol) and HOBT (164 mg, 1.21 mmol) in DMF (5 ml); EDCI (213 mg, 1.11 mmol) in DMF (0.5 mL) gave the title compound (226 mg, 50.5%) as a racemic mixture in the form of a white solid. $^1$H NMR (DMSO-d$_6$, 400 MHz): δ 11.85 (bs, 1H); 8.89-8.81 (dd, 1H, J=7.21 Hz; J=7.42 Hz); 7.91-7.88 (dd, 1H, J=2.5 Hz; J=2.5 Hz); 7.77-7.74 (q, 1H); 7.57 (s, 1H); 7.32-7.27 (td, 1H, J=2.5 Hz; J=2.5 Hz; J=2.5 Hz); 6.85 (s, 1H); 4.82-4.76 (m, 1H); 4.23-4.16 (m, 2H); 3.76-3.74 (dd, 1H, J=1.8 Hz; J=1.8 Hz); 3.65-3.61 (, 1H, J=1.8 Hz; J=1.8 Hz); 3.17-2.98 (m, 2H); 1.25-1.17 (t, 3H). $^{13}$C NMR (DMSO-d$_6$, 100 MHz): 171.13 & 171.09, 167.47 & 167.45, 165.83 & 165.65, 160.32, 158.21 & 157.93, 145.64, 135.40, 133.23 & 133.12, 122.17 & 122.08, 114.83 & 114.59, 108.74 & 108.47, 62.01, 53.86 & 53.65, 53.40 & 53.33, 51.86 & 51.81, 14.34.

(2S,3S)-ethyl-3-((S)-1-oxo-1-(phenylamino)-3-(thiazol-4-yl)propan-2-ylcarbamoyl)oxirane-2-carboxylate (19a)

General procedure using: Boc-protected peptidomimetic (230 mg, 0.66 mmol); (2S,3S)-epoxysuccinic acid monoester (106 mg, 0.66 mmol), DIPEA (0.12 mL, 0.66 mmol) and HOBT (110 mg, 0.79 mmol) in CH$_2$Cl$_2$ (5 ml); EDCI (130 mg, 0.66 mmol) in DMF (0.5 mL) gave the title compound (84 mg, 32.5%) as white solid. $^1$H NMR (MeOD-d$^4$, 400 MHz): δ 8.94 (s, 1H); 7.52-7.50 (d, 2H); 7.33 (s, 1H); 7.30-7.26 (t, 3H); 7.11-7.07 (t, 1H); 4.98-4.95 (t, 1H); 4.24-4.20 (q, 2H); 3.69 (s, 1H); 3.54 (s, 1H); 3.43-3.28 (m, 2H); 1.28-1.24 (t, 3H). $^{13}$C NMR (MeOD-d$^4$, 100 MHz): 169.43, 167.21, 166.84, 153.89, 152.24, 137.82, 128.45, 124.23, 120.24, 116.10, 61.82, 53.60, 53.11, 51.92, 32.94, 12.99.

(2S,3S)-ethyl-3-((S)-1-(4-(4-fluorophenyl)thiazol-2-ylamino)-1-oxo-3-(thiazol-4-yl)propan-2-ylcarbamoyl)oxirane-2-carboxylate (19b)

Synthesized following the optimized coupling procedure using: (2S,3S)-epoxysuccinic acid monoester (622 mg, 3.88 mmol), DIPEA (0.75 mL, 4.2 mmol) in DMF (5 ml); EDCI (890 mg, 4.7 mmol); HOBt (730 mg, 5.4 mmol); deprotected free amine (1.35 g, 3.9 mmol) in DMF (5 ml); after column chromatography afforded the title compound (isolated yield=1.38 g, 72.4%) as white solid. $^1$H NMR (400 MHz, MeOD-d$^4$): δ 8.98-8.98 (d, 1H, J=1.75 Hz); 7.92-7.90 (q, 2H); 7.37 (s, 1H); 7.36 (s, 1H); 7.15-7.10 (t, 2H); 5.06-5.02 (q, 1H); 4.27-4.24 (q, 2H); 3.69-3.68 (d, 1H, J=1.66 Hz); 3.55-3.54 (d, 1H, J=1.66 Hz); 3.56-3.29 (m, 2H); 1.33-1.29. $^{13}$C NMR (DMSO-d$_6$, 100 MHz): 169.17, 167.17, 157.69, 154.00, 151.90, 148.90, 130.95, 127.55, 116.15, 114.99, 114.77, 107.20, 61.76, 52.97, 52.91, 51.82, 32.35, 12.89. ESI-HRMS (m/z): [M−H]$^+$ calcd. for C$_{21}$H$_{19}$FN$_4$O$_5$S$_2$: 489.0781, observed: 489.0731.

(2S,3S)-ethyl 3-((S)-1-(4-(4-ethynylphenyl)thiazol-2-ylamino)-1-oxo-3-(thiazol-4-yl)propan-2-ylcarbamoyl)oxirane-2-carboxylate (19c)

$^1$H NMR (DMSO-d$^6$, 400 MHz) δ=12.56 (s, 1H); 9.04-9.03 (d, 1H, J=1.8 Hz); 8.84-8.82 (d, 1H, J=7.7 Hz); 7.93-7.91 (d, 2H, J=8.3 Hz); 7.76 (s, 1H); 7.55-7.53 (d, 2H, J=8.3 Hz); 7.45-7.44 (d, 1H, J=1.6 Hz); 4.99-4.93 (q, 1H); 4.26 (s, 1H); 4.22-4.16 (m, 2H); 3.72-3.71 (d, 1H, J=1.7 Hz); 3.56-3.55 (d, 1H, J=1.7 Hz); 3.67-3.22 (m, 2H); 1.25-1.19 (t, 3H). $^{13}$C NMR (DMSO-d$^6$, 100 MHz): 170.04, 167.47, 165.62, 158.24, 154.25, 152.62, 148.47, 134.95, 132.61, 126.26, 121.33, 116.67, 110.21, 83.87, 81.99, 62.02, 53.36, 53.11, 51.81, 33.11, 14.33. ESI-HRMS (m/z): [M+H]$^+$ calcd. for C$_{23}$H$_{20}$N$_4$O$_5$S$_2$: 497.0948; observed, 497.0949; HPLC method 2: Purity=96.7%, R$_t$=14.5 min (Ion-Trap HPLC).

(2S,3S)-ethyl-3-((S)-1-(4-(4-fluorophenyl)thiazol-2-ylamino)-3-(1-methyl-1H-imidazol-5-yl)-1-oxopropan-2-ylcarbamoyl)oxirane-2-carboxylate (20)

General procedure using: Boc-protected peptidomimetic (200 mg, 0.45 mmol); (2S,3S)-epoxysuccinic acid monoester (72 mg, 0.44 mmol), DIPEA (0.078 mL, 0.44 mmol) and HOBT (73 mg, 0.53 mmol) in DMF (4 ml); EDCI (95 mg, 0.49 mmol) in DMF (0.5 mL) gave the title compound (152 mg, 69.3%) as white solid. $^1$H NMR (DMSO-d$^6$, 400 MHz): δ 12.59 (bs, 1H); 8.97-8.95 (d, 1H, J=7.82 Hz); 7.95-7.92 (q, 2H); 7.64 (s, 1H); 7.50 (s, 1H); 7.28-7.24 (t, 2H); 6.67 (s, 1H); 4.87-4.81 (q, 1H); 4.21-4.15 (m, 2H); 3.74-3.73 (d, 1H, J=1.79 Hz); 3.59 (s, 3H), 3.55-3.54 (d, 1H, J=1.79 Hz); 3.16-2.97 (m, 2H); 1.24-1.17 (t, 3H). $^{13}$C NMR (DMSO-d$^6$, 100 MHz): 169.95, 167.48, 165.56, 163.45, 161.02, 148.41, 138.56, 131.27, 128.18, 128.09, 127.82, 127.00, 116.16, 115.95, 108.70, 62.01, 53.24, 52.36, 51.70, 31.30, 26.40, 14.33. ESI-LRMS (m/z): [M+H]$^+$ calcd. for $C_{22}H_{22}FN_5O_5S$: 487.5, observed: 488.0.

(2S,3S)-ethyl-3-((S)-1-(4-(4-fluorophenyl)thiazol-2-ylamino)-3-(1-methyl-1H-imidazol-4-yl)-1-oxopropan-2-ylcarbamoyl)oxirane-2-carboxylate (21)

General procedure using: Boc-protected peptidomimetic (185.5 mg, 0.41 mmol); (2S,3S)-epoxysuccinic acid monoester (67 mg, 0.41 mmol), DIPEA (0.07 mL, 0.41 mmol) and HOBT (68 mg, 0.49 mmol) in DMF (3 ml); EDCI (88 mg, 0.45 mmol) in DMF (0.5 mL) gave the title compound (104 mg, 50.2%) as white solid. $^1$H NMR (DMSO-d$_6$, 400 MHz): 12.49 (bs, 1H); 8.74-8.72 (d, 1H, J=7.4 Hz); 7.95-7.92 (q, 2H); 7.62 (s, 1H); 7.49 (s, 1H); 7.27-7.24 (t, 2H); 6.89 (s, 1H); 4.77-4.74 (q, 1H); 4.22-4.17 (m, 2H); 3.75-3.74 (d, 1H, J=1.8 Hz); 3.62-3.61 (d, 1H, J=1.8 Hz); 3.58 (s, 3H); 3.02-2.91 (m, 2H); 1.26-1.22 (t, 3H). $^{13}$C NMR (DMSO-d$^6$, 100 MHz): 170.31, 167.48, 165.56, 163.43, 161.00, 148.32, 137.89, 136.98, 131.31, 128.11 (d, J=8.1 Hz); 118.45, 116.14, 115.92, 108.49, 62.01, 53.54, 53.40, 51.87, 33.24, 30.55, 14.34. ESI-LRMS (m/z): [M+H]$^+$ calcd. for $C_{22}H_{22}FN_5O_5S$: 487.5, observed: 488.0.

(2S,3S)-3-((S)-4-methyl-1-oxo-1-(phenylamino)pentan-2-ylcarbamoyl)oxirane-2-carboxylic acid (22)

Followed general procedure using: the corresponding peptidomimetic epoxide ethyl ester 17a (70 mg, 0.2 mmol); LiOH (4.8 mg, 0.2 mmol); after extraction afforded the desired product as a white solid (54 mg, 83.9%). $^1$H NMR (MeOD-d$^4$, 400 MHz): δ 7.57-7.55 (d, 2H); 7.33-7.29 (t, 2H); 7.13-7.09 (t, 1H); 4.64-4.61 (m, 1H); 3.71 (s, 1H); 3.57 (s, 1H); 1.76-1.65 (m, 3H); 1.02-0.98 (t, 6H). $^{13}$C NMR (MeOD-d$^4$, 100 MHz): 171.22, 169.07, 167.14, 137.98, 128.41, 124.12, 120.14, 52.90, 52.58, 51.69, 40.70, 29.49, 24.64, 22.04, 20.59. ESI-HRMS (m/z): [M–H]$^+$ calcd. for $C_{16}H_{20}N_2O_5$: 319.3404, observed: 319.1332. HPLC Method 1: R$_t$=21.0 min, purity=96.1%.

(2S,3S)-3-((S)-1-(2,6-difluorophenylamino)-4-methyl-1-oxopentan-2-ylcarbamoyl)oxirane-2-carboxylic acid (23a)

Followed general procedure using: the corresponding peptidomimetic epoxide ethyl ester 17b (28 mg, 0.72 mmol); LiOH (1.7 mg, 0.072 mmol); after extraction afforded the desired product as a white solid (20 mg, 77.0%). $^1$H NMR (MeOD-d$^4$, 400 MHz): δ 7.91 (s, 1H); 7.36-7.31 (m, 1H); 7.07-7.02 (t, 2H); 4.72 (m, 1H); 3.65 (s, 1H); 3.52 (s, 1H); 1.74-1.68 (m, 3H); 1.01-0.99 (d, 6H). $^{13}$C NMR (DMSO-d$^6$, 100 MHz): 171.26, 169.20, 165.81, 159.49 (d, J=5.2 Hz), 157.00 (d, J=5.2 Hz), 128.98 (t, J=19.7 Hz); 115.34 (t, J=34.0 Hz); 113.10 (d, J=5.2 Hz), 107.43, 106.22, 52.96, 51.51, 51.32, 41.30, 24.71, 23.81. ESI-HRMS (m/z): [M–H]$^+$ calcd. for $C_{16}H_{20}N_2O_5$: 355.3216, observed: 355.3101. HPLC Method 1: R$_t$=19.7 min, purity=95.0%.

(2R,3R)-3-((S)-1-(2,6-difluorophenylamino)-4-methyl-1-oxopentan-2-ylcarbamoyl)oxirane-2-carboxylic acid (23b)

Followed general procedure using: the corresponding peptidomimetic epoxide ethyl ester 17c (85 mg, 0.22 mmol); LiOH (5.2 mg, 0.22 mmol); after extraction afforded the desired product as a white solid (59 mg, 74.8%). $^1$H NMR (DMSO-d$^6$, 400 MHz): δ 9.88 (s, 1H); 8.81-8.79 (d, 1H, J=8.21 Hz); 7.38-7.33 (m, 1H); 7.17-7.13 (t, 2H); 4.61-4.56 (q, 1H); 3.70-3.69 (d, 1H, J=1.79 Hz); 3.52-3.51 (d, 1H, J=1.79 Hz); 1.66-1.58 (m, 3H); 0.93-0.88 (dd, 6H). $^{13}$C NMR (DMSO-d$_6$, 100 MHz): 171.35, 169.20, 165.79, 159.48 (d, J=5.16 Hz); 157.01 (d, J=5.21 Hz); 128.58 (t, 19.7 Hz); 114.63 (t, J=34.0 Hz); 112.39 (d, J=22.6 Hz); 53.05, 51.71, 51.62, 41.32, 24.71, 21.96. ESI-HRMS (m/z): [M–H]$^+$ calcd. for $C_{16}H_{20}N_2O_5$: 355.3216, observed: 355.3201. HPLC Method 1: R$_t$=18.9 min, purity=96.5%.

(2S,3S)-3-((S)-1-(4-(4-fluorophenyl)thiazol-2-ylamino)-4-methyl-1-oxopentan-2-ylcarbamoyl)oxirane-2-carboxylic acid (24a)

Followed general procedure using: the corresponding peptidomimetic epoxide ethyl ester 17d (203 mg, 0.45 mmol); LiOH (10.8 mg, 0.45 mmol); after extraction afforded the desired product as a white solid (150 mg, 78.8%). $^1$H NMR (DMSO-d$^6$, 400 MHz): δ 12.51 (bs, 1H); 8.64-8.61 (d, 1H, J=12.0 Hz); 7.95-7.92 (t, 2H); 7.62 (s, 1H); 7.28-7.24 (t, 2H); 4.63-4.58 (m, 1H); 3.51-3.50 (d, 1H, J=1.60 Hz); 3.34-3.33 (d, 1H, J=1.60 Hz); 165-1.54 (m, 3H); 0.91-0.88 (t, 6H). $^{13}$C NMR (MeOD-d$^4$, 100 MHz): 172.44, 165.32, 162.87, 159.37, 150.45, 132.60, 132.57, 129.14, 129.06, 116.56, 116.34, 108.69, 54.41, 53.55, 53.19, 41.79, 26.21, 23.54, 22.02. ESI-HRMS (m/z): [M+H$^+$] calcd. for $C_{19}H_{20}FN_3O_5S$: 422.1180, observed: 422.1188. HPLC Method 1: R$_t$=24.6 min, purity=95.7%.

(2R,3R)-3-((S)-1-(4-(4-fluorophenyl)thiazol-2-ylamino)-4-methyl-1-oxopentan-2-ylcarbamoyl)oxirane-2-carboxylic acid (24b)

Followed general procedure using: the corresponding peptidomimetic epoxide ethyl ester 17e (76.4 mg, 0.16 mmol); LiOH (8 mg, 0.34 mmol); after extraction afforded the desired product as a white solid (51 mg, 71.5%). $^1$H NMR (DMSO-d$^6$, 400 MHz): δ 12.52 (s, 1H); 8.78-8.76 (d, 1H, J=8.0 Hz); 7.94-7.92 (t, 2H); 7.63 (s, 1H); 7.29-7.24 (t, 2H); 4.58-4.57 (m, 1H); 3.62-3.61 (d, 1H, J=1.80 Hz); 3.41-3.40 (d, 1H, J=1.80 Hz); 1.64-1.51 (m, 3H); 0.91-0.88 (dd, 6H). $^{13}$C NMR (DMSO-d$^6$, 100 MHz): 171.02, 166.26, 162.88, 160.46, 157.72, 147.81, 130.80, 130.77, 127.62, 127.54, 115.59 (d, J=21.6 Hz); 107.97, 52.36, 52.08, 51.37, 28.89, 24.25, 22.82, 21.19. ESI-HRMS (m/z): [M+H$^+$] calcd. for $C_{19}H_{20}FN_3O_5S$: 422.1180, observed: 422.1186. HPLC Method 1: R$_t$=23.8 min, purity=95.1%.

(2S,3S)-3-((S)-1-(4-(4-fluorophenylsulfonamido)butylamino)-4-methyl-1-oxopentan-2-ylcarbamoyl)oxirane-2-carboxylic acid (25)

Followed general procedure using: the corresponding peptidomimetic epoxide ethyl ester 17f (213 mg, 0.42 mmol); LiOH (21 mg, 0.85 mmol); after extraction afforded the desired product as a white solid (110 mg, 54.7%). $^1$H NMR (DMSO-d$^6$, 400 MHz): δ 8.15 (s, 1H); 7.89-7.85 (m, 2H); 7.38 (s, 1H); 7.21-7.17 (t, 2H); 6.14 (s, 1H); 3.68-3.60 (d, 2H); 3.38-3.37 (d, 1H, J=1.60 Hz); 3.10-3.09 (d, 1H, J=1.60 Hz); 2.97 (s, 1H); 2.85 (s, 1H); 1.65-1.56 (m, 7H); 0.91-0.88 (m, 6H). $^{13}$C NMR (DMSO-d$_6$, 100 MHz): 173.41, 170.47, 166.90, 166.52, 163.99, 135.75, 135.72, 130.03, 129.93, 116.71, 116.48, 53.83, 52.32, 43.08, 41.34, 39.65, 26.76, 26.22, 24.95, 22.94, 22.06. ESI-HRMS (m/z):

[M+H⁺] calcd. for $C_{20}H_{28}FN_3O_7S$: 474.1705, observed: 474.1707. HPLC Method 1: $R_t$=20.9 min, purity=99.0%.

(2S,3S)-3-((2S)-1-(4-(5-(1,2-dithiolan-3-yl)pentanamido)butylamino)-4-methyl-1-oxopentan-2-ylcarbamoyl)oxirane-2-carboxylic acid (26)

17g (53 mg, 0.1 mmol) was dissolved in 2 mL of 3:1:1 mixture THF, methanol and water and cooled to 0° C. and LiOH (5 mg, 0.2 mmol) was added. After stirring at the same temperature for 15 min the resulting solution was acidified with 1N HCl and extracted with $CH_2Cl_2$. The organic layer was washed with water, brine, and dried over anhydrous $Na_2SO_4$ and concentrated in vacuo. Column purification of the crude mixture ($SiO_2$, 15% $MeOH/CHCl_3$) gave the title compound as a white solid. ¹H NMR ($CDCl_3$, 400 MHz): δ 8.01-7.99 (d, 1H, J=10.8 Hz); 7.26 (s, 1H); 6.25 (bs, 1H); 4.57-4.53 (q, 1H); 3.69 (s, 1H); 3.59 (s, 1H); 3.21-3.31 (m, 5H); 2.45-2.42 (m, 1H); 2.24-2.20 (t, 2H); 1.94-1.92 (m, 1H); 1.66-1.51 (m, 12H); 1.25-1.21 (m, 2H); 0.94-0.91 (m, 6H). ¹³C NMR ($CDCl_3$, 100 MHz): 174.12, 172.13, 168.92, 166.64, 56.52, 53.57, 52.57, 51.62, 41.19, 40.31, 39.09, 38.93, 38.50, 36.24, 34.63, 28.93, 26.56, 26.42, 25.55, 24.85, 22.80, 21.87. ESI-HRMS (m/z): [M+H⁺] calcd. for $C_{22}H_{37}N_3O_6S_2$: 504.2197, observed: 504.2192. HPLC Method 1: $R_t$=21.7 min, purity=95.4%.

(2S,3S)-3-((S)-4-methyl-1-oxo-1-(4-(5-((3aS,4S,6aR)-2-oxohexahydro-1H-thieno[3,4-d]imidazol-4-yl)pentanamido)butylamino)pentan-2-ylcarbamoyl)oxirane-2-carboxylic acid (27)

Synthesized following general saponification procedure using the following quantities: the corresponding peptidomimetic epoxide ethyl ester 17h (155 mg, 0.3 mmol); LiOH (14 mg, 0.58 mmol); $MeOH/H_2O$ (1.5 mL:0.5 mL:0.5 mL); yielded 27 as a white solid (40 mg, 27.1%). ¹H NMR ($DMSO-d_6$, 400 MHz): 8.56 (d, 1H); 8.06 (t, 1H); 7.76 (t, 1H); 6.41 (s, 1H), 6.35 (s, 1H); 4.57 (m, 2H); 4.31 (m, 1H); 3.66 (d, 1H); 3.31 (d, 1H); 3.08 (m, 1H); 3.01 (m, 3H); 2.80 (dd, 1H); 2.56 (d, 1H); 2.04 (t, 2H); 1.53 (m, 6H); 1.43 (m, 3H); 1.36 (m, 2H); 0.89 (d, 3H); 0.84 (d, 3H). ¹³C NMR ($DMSO-d_6$, 100 MHz): 171.80, 171.06, 168.78, 164.85, 162.68, 61.00, 59.16, 55.36, 52.65, 51.19, 41.14, 35.17, 28.17, 27.98, 26.59, 26.45, 25.28, 24.24, 22.87, 21.61. ESI-HRMS (m/z): no ionization, mass not seen. HPLC Method 1: $R_t$=14.8 min, purity=95.6%.

(2S,3S)-3-((S)-3-(1H-imidazol-4-yl)-1-oxo-1-(phenylamino)propan-2-ylcarbamoyl)oxirane-2-carboxylic acid (28)

Synthesized following general saponification procedure using the following quantities: the corresponding peptidomimetic epoxide ethyl ester 18a (155 mg, 0.3 mmol); LiOH (14 mg, 0.58 mmol); $MeOH/H_2O$ (1.5 mL:0.5 mL:0.5 mL); yielded 28 as a white solid (40 mg, 27.1%). ¹H NMR ($MeOD-d^4$, 400 MHz): δ 8.66 (s, 1H); 7.57-7.55 (d, 2H, J=7.86 Hz); 7.29-7.27 (t, 3H); 7.10-7.07 (t, 1H); 4.97-4.94 (q, 1H); 3.64-3.63 (d, 1H, J=1.66 Hz); 3.529-3.525 (d, 1H, J=1.66 Hz); 3.36-3.15 (m, 2H). ¹³C NMR ($MeOD-d^4$, 100 MHz): 169.79, 167.26, 166.95, 137.90, 134.99, 128.37, 124.10, 120.11, 54.13, 52.94, 51.67. ESI-HRMS (m/z) [M+H⁺] calcd. for $C_{16}H_{16}N_4O_5$: 345.1194, observed: 345.1185. HPLC Method 1: $R_t$=18.2 min, purity=95.2%.

(2S,3S)-3-((S)-3-(1H-imidazol-5-yl)-1-(mesitylamino)-1-oxopropan-2-ylcarbamoyl)oxirane-2-carboxylic acid (29)

Synthesized following general saponification procedure using the following quantities: the corresponding peptidomimetic epoxide ethyl ester 18b (51.6 mg, 0.1 mmol); LiOH (5 mg, 0.2 mmol); $MeOH/H_2O$ (1.5 mL:0.5 mL:0.5 mL); yielded 29 as a white solid (26.2 mg, 54.2%). ¹H NMR ($MeOD-d^4$, 400 MHz): δ 7.62 (s. 1H); 6.93 (s, 1H); 6.87 (s, 2H); 4.84-4.82 (m, 1H); 3.53-3.49 (d, 1H); 3.38-3.35 (d, 1H); 3.25-3.22 (m, 2H); 2.25 (s, 3H); 2.07 (s, 6H). ¹³C NMR ($MeOD-d^4$, 100 MHz): 174.40, 172.62, 170.80, 168.89, 136.54, 135.74, 135.11, 133.43, 131.25, 128.18, 117.26, 54.20, 53.82, 53.69, 52.80, 29.34, 19.55, 16.86. ESI-HRMS (m/z): [M−H⁺] calcd. for $C_{19}H_{22}N_4O_5$: 385.1517, observed: 385.1516. HPLC Method 2: $R_t$=16.4 min, purity=95.4%.

(2S,3S)-3-(1-(4-(4-fluorophenyl)thiazol-2-ylamino)-3-(1H-imidazol-4-yl)-1-oxopropan-2-ylcarbamoyl)oxirane-2-carboxylic acid (30a)

Synthesized following general saponification procedure using the following quantities: the corresponding peptidomimetic epoxide ethyl ester 18c (184 mg, 0.39 mmol); LiOH (14 mg, 0.58 mmol); $MeOH/H_2O$ (1.5 mL:0.5 mL:0.5 mL); yielded 30a as a white solid (40 mg, 27.1%). ¹H NMR ($DMSO-d_6$, 400 MHz): δ 12.50 (bs, 1H); 8.84-8.73 (dd, 1H, J=7.3 Hz, 7.3 Hz); 7.95-7.91 (q, 2H); 7.73 (s, 1H); 7.63 (s, 1H); 7.29-7.24 (t, 2H); 6.90 (s, 1H); 4.81-4.74 (m, 1H); 3.65-3.64 (dd, 2H, J=1.68 Hz, 1.68 Hz); 3.46-3.42 (dd, 2H, J=1.65 Hz, 1.65 Hz); 3.09-3.01 (m, 2H). ¹³C NMR ($DMSO-d^6$, 100 MHz): 169.81, 165.89, 163.95, 157.92, 147.96, 134.99, 132.93, 132.91, 127.89, 127.72, 115.77, 115.56, 108.17, 99.59, 52.69, 51.85, 51.77. ESI-HRMS (m/z): [M+H⁺] calcd. for $C_{19}H_{16}FN_5O_5S$: 446.0929, observed: 446.0922. HPLC method 2: $R_t$=16.2 min (S-isomer) & 12.8 min (R-isomer), purity=98.2%. Isomeric identity was determined by resynthesis with the use of HOBT in the initial peptide coupling. This led to isolation of the enantiomerically pure S-isomer, which elutes at $R_t$=16.2 min, corresponding to the S-isomer in the enantiomeric mixture.

(2R,3R)-3-((S)-1-(4-(4-fluorophenyl)thiazol-2-ylamino)-3-(1H-imidazol-4-yl)-1-oxopropan-2-ylcarbamoyl)oxirane-2-carboxylic acid (30b)

Synthesized following general saponification procedure using the following quantities: the corresponding peptidomimetic epoxide ethyl ester 18d (200 mg, 0.42 mmol); LiOH (12 mg, 0.50 mmol); $THF/MeOH/H_2O$ (2.5 mL:1.5 mL:1.5 mL); yielded 30b as a white solid (85 mg, 45.2%). ¹H NMR ($DMSO-d_6$, 400 MHz): δ 12.52 (bs, 1H); 8.85-8.75 (dd, 2H, J=6.9 Hz; J=43.1 Hz); 7.94-7.91 (t, 2H); 7.80 (s, 1H); 7.62 (s, 1H); 7.28-7.24 (t, 2H); 6.93 (s, 1H); 4.80-4.76 (q, 1H); 3.65-3.64 (d, 1H, J=4.40 Hz); 3.46-3.42 (d, 1H, J=14.0 Hz); 3.09-2.96 (m, 2H). ¹³C NMR ($DMSO-d_6$, 100 MHz): 169.5, 168.8, 165.9, 162.9, 160.5, 157.6, 147.8, 134.6, 132.1, 130.7, 127.6, 116.4, 115.5 (d, J=21.4 Hz), 108.0, 52.9, 52.7, 52.6, 51.9, 28.6. ESI-HRMS (m/z): [M+H⁺] calcd. for $C_{19}H_{16}FN_5O_5S$: 446.0928, observed: 446.0939; HPLC method 2: $R_t$=15.8 min, purity=97.2%.

(2S,3S)-3-((S)-1-(6-fluorobenzo[d]thiazol-2-ylamino)-3-(1H-imidazol-4-yl)-1-oxopropan-2-ylcarbamoyl)oxirane-2-carboxylic acid (31a)

Synthesized following general saponification procedure using the following quantities: the corresponding peptidomimetic epoxide ethyl ester 18e (153 mg, 0.32 mmol); LiOH (7.7 mg, 0.32 mmol); THF/MeOH/H$_2$O (3.5 mL:1.5 mL:1.5 mL); yielded 31a as a white solid (103 mg, 71.5%). $^1$H NMR (DMSO-d$_6$, 400 MHz): δ 14.55 (bs, 1H); 14.36 (bs, 1H); 9.18-9.02 (m, 2H); 7.93-7.91 (m, 1H); 7.79-7.75 (m, 1H); 7.44 (s, 1H); 7.31-7.29 (t, 1H); 4.96-4.91 (q, 1H); 3.72-3.71 (d, 1H, J=1.62 Hz); 3.51-3.50 (d, 1H, J=1.62 Hz); 3.29-3.16 (m, 2H). %). $^{13}$C NMR (DMSO-d$_6$, 100 MHz): 169.50, 168.51, 165.86, 165.84, 159.82, 157.53, 157.44, 145.02, 133.67, 132.68, 132.57, 128.56, 121.63, 117.01, 114.40, 114.16, 108.27, 108.00, 52.67, 52.19, 51.34, 26.20. ESI-HRMS (m/z): [M+H$^+$] calcd. for C$_{17}$H$_{14}$FN$_5$O$_5$S: 420.0773, observed: 420.0777.

(2R,3R)-3-((S)-1-(6-fluorobenzo[d]thiazol-2-ylamino)-3-(1H-imidazol-4-yl)-1-oxopropan-2-ylcarbamoyl)oxirane-2-carboxylic acid (31b)

Synthesized following general saponification procedure using the following quantities: the corresponding peptidomimetic epoxide ethyl ester 18f (125 mg, 0.26 mmol); LiOH (6.2 mg, 0.26 mmol); THF/MeOH/H$_2$O (1.5 mL:1.0 mL:0.5 mL); yielded 31b as a white solid (46 mg, 39.1%). $^1$H NMR (400 MHz, MeOD-d$^4$): δ 11.88 (bs, 1H), 8.89-8.83 (dd, 1H, J=7.4 Hz, J=7.4 Hz); 7.91-7.89 (d, 1H, J=2.5 Hz); 7.78-7.72 (q, 1H); 7.56 (s, 1H); 7.30 (td, 1H, J=2.6 Hz); 6.85 (s, 1H); 4.81-4.76 (m, 1H); 3.76-3.74 (dd, 1H, J=1.68 Hz); 3.45-3.43 (dd, 1H, J=1.65 Hz); 3.11-3.00 (m, 2H). $^{13}$C NMR (DMSO-d$_6$, 100 MHz): 171.13, 167.48, 165.83, 160.32, 158.21, 145.64, 135.40, 133.23, 122.17, 114.83, 108.74, 53.86, 53.40, 51.86. ESI-HRMS (m/z): [M+H$^+$] calcd. for C$_{17}$H$_{14}$FN$_5$O$_5$S: 420.0773, observed: 420.0769.

(2S,3S)-3-((S)-1-oxo-1-(phenylamino)-3-(thiazol-4-yl)propan-2-ylcarbamoyl)oxirane-2-carboxylic acid (32)

Synthesized following general saponification procedure using the following quantities: the corresponding peptidomimetic epoxide ethyl ester 19a (112 mg, 0.28 mmol); LiOH (6.9 mg, 0.29 mmol); THF/MeOH/H$_2$O (2.5 mL:1.0 mL:1.0 mL); yielded 32 as a white solid (45 mg, 43.3%). $^1$H NMR (MeOD-d$^4$, 400 MHz): δ 8.97 (s, 1H); 7.52-7.50 (d, 2H); 7.32 (s, 1H); 7.30-7.26 (t, 3H); 4.94-4.92 (t, 1H); 3.62 (s, 1H); 3.52-3.45 (q, 2H); 3.43 (s, 1H). $^{13}$C NMR (DMSO-d$_6$, 100 MHz): 172.48, 169.65, 168.87, 153.83, 152.41, 138.16, 128.33, 124.04, 120.73, 115.89, 54.49, 53.60, 52.89 32.87. ESI-HRMS (m/z): [M+H$^+$] calcd. for C$_{16}$H$_{15}$N$_3$O$_5$S: 360.0660, observed: 360.0673; HPLC method 2: R$_t$=16.4 min; Purity: 95.2%.

(2S,3S)-3-((S)-1-(4-(4-fluorophenyl)thiazol-2-ylamino)-1-oxo-3-(thiazol-4-yl)propan-2-ylcarbamoyl)oxirane-2-carboxylic acid (33)

Synthesized following general saponification procedure using the following quantities: the corresponding peptidomimetic epoxide ethyl ester 19b (974 mg, 2.0 mmol); LiOH (47.5 mg, 2.0 mmol); THF/MeOH/H$_2$O (25 mL:5 mL:2 mL); yielded 33 as a white solid (685 mg, 74.6%). $^1$H NMR (MeOD-d$^4$, 400 MHz): δ 8.99-8.98 (d, 1H, J=1.67 Hz); 7.94-7.91 (q, 2H); 7.37 (s, 1H); 7.36 (s, 1H); 7.15-7.10 (t, 2H); 5.06-5.02 (q, 1H); 3.64-3.63 (d, 1H, J=1.57 Hz); 3.49-3.45 (m, 3H). $^{13}$C NMR (MeOD-d$^4$, 100 MHz): 170.05, 169.01, 166.19, 163.43, 158.19, 154.25, 152.66, 148.36, 131.30, 128.18, 116.63, 116.15, 115.93, 108.62, 53.12, 53.05, 52.21, 33.09. ESI-HRMS (m/z): [M+H$^+$] calcd. for C$_{19}$H$_{15}$FN$_4$O$_5$S$_2$: 463.0541, observed: 463.0545; HPLC method 2: R$_t$=23.3 min; purity=96.3%.

(2S,3S)-3-((S)-1-(4-(4-ethynylphenyl)thiazol-2-ylamino)-1-oxo-3-(thiazol-4-yl)propan-2-ylcarbamoyl)oxirane-2-carboxylic acid (34)

Synthesized following general saponification procedure using the following quantities: 19c (115 mg, 0.23 mmol); LiOH (6.7 mg, 0.28 mmol); THF/MeOH/H$_2$O (4.5 ml:1.5 ml:1.5 ml); yielded 34 as a white solid (48 mg, 44.2%). $^1$H NMR (DMSO-d$^6$, 400 MHz): δ 12.57 (s, 1H); 9.06-9.05 (d, 1H, J=1.92 Hz); 8.81-8.79 (d, 1H, J=7.8 Hz); 7.93-7.91 (d, 2H, J=8.4 Hz); 7.76 (s, 1H); 7.55-7.53 (d, 2H, J=8.4 Hz); 7.45-7.44 (d, 1H, 1.8 Hz); 4.98-4.93 (q, 1H); 4.25 (s, 1H); 3.66-3.65 (d, 1H, J=1.8 Hz); 3.42-3.41 (d, 1H, J=1.8 Hz); 3.35-3.22 (m, 2H). $^{13}$C NMR (DMSO-d$^6$, 100 MHz): 170.08, 169.03, 165.98, 158.25, 154.33, 152.54, 148.47, 134.95, 132.61, 126.26, 121.32, 116.75, 110.20, 83.87, 81.99, 53.15, 53.08, 51.88, 33.05. ESI-HRMS (m/z): [M+H$^{+1}$] calcd. for C$_{21}$H$_{16}$N$_4$O$_5$S$_2$: 469.0635; observed, 469.0627; HPLC method 1: R$_t$=12.5 min, Purity=95.7%.

(2S,3S)-3-((S)-1-(4-(4-fluorophenyl)thiazol-2-ylamino)-3-(1-methyl-1H-imidazol-5-yl)-1-oxopropan-2-ylcarbamoyl)oxirane-2-carboxylic acid (35)

Synthesized following general saponification procedure using the following quantities: the corresponding peptidomimetic epoxide ethyl ester 20 (129 mg, 0.26 mmol); LiOH (6.3 mg, 0.26 mmol); THF/MeOH/H$_2$O (2.5 mL:1.5 mL:1.5 mL); yielded 35 as a white solid (56 mg, 46.1%). $^1$H NMR (DMSO-d$_6$, 400 MHz): 8.92-8.90 (d, 1H); 7.96-7.91 (m, 2H); 7.68 (s, 1H); 7.35-7.24 (m, 3H); 4.94-4.87 (m, 1H); 4.64-4.56 (m, 2H); 3.82-3.50 (m, 5H). $^{13}$C NMR (400 MHz, DMSO-d$_6$): 171.52, 167.50, 165.57, 162.45, 161.02, 148.42, 138.62, 131.27, 128.18, 128.01, 127.83, 127.05, 116.17, 115.99, 106.70, 53.24, 52.58, 51.90, 31.29, 29.52. ESI-HRMS (m/z): [M+H$^+$] calcd. for C$_{20}$H$_{18}$FN$_5$O$_5$S: 460.1085; observed, 460.1092; R$_t$=17.8 min, purity=93.6%.

(2S,3S)-3-((S)-1-(4-(4-fluorophenyl)thiazol-2-ylamino)-3-(1-methyl-1H-imidazol-4-yl)-1-oxopropan-2-ylcarbamoyl)oxirane-2-carboxylic acid (36)

Synthesized following general saponification procedure using the following quantities: the corresponding peptidomimetic epoxide ethyl ester 21 (93 mg, 0.19 mmol); LiOH (4.5 mg, 0.19 mmol); THF/MeOH/H$_2$O (1.5 mL:0.5 mL:0.5 mL); yielded 36 as a white solid (29 mg, 33.1%). $^1$H NMR (400 MHz, DMSO-d$_6$): 12.50 (bs, 1H), 8.82-8.80 (d, 1H); 7.93-7.91 (m, 2H); 7.76 (s, 1H); 7.63 (s, 1H); 7.46-7.24 (t, 2H); 6.99 (s, 1H); 4.79-4.74 (m, 1H); 3.67-3.66 (d, 1H); 3.62 (s, 3H); 3.49-3.48 (d, 1H); 3.12-2.90 (m, 2H). $^{13}$C NMR (400 MHz, DMSO-d$_6$): 169.72, 168.60, 165.56, 162.97, 160.54, 157.78, 147.88, 137.17, 130.84, 127.71, 127.63, 118.35, 115.68, 115.47, 108.08, 53.07, 52.98, 51.56, 33.11, 29.60. ESI-HRMS (m/z): [M+H$^+$] calcd. for C$_{20}$H$_{18}$FNO$_5$S: 460.1085, observed: 460.1090. R$_t$=18.1 min, purity=95.3%.

Preparation of the Alkynyl Epoxide-Ester for Click Derivatization, 37

(2S,3S)-ethyl-3-((S)-1-oxo-1-(prop-2-ynylamino)-3-(thiazol-4-yl)propan-2-ylcarbamoyl)oxirane-2-carboxylate (37)

37 was generated using the peptide coupling procedure using: Boc-protected peptidomimetic (740 mg, 3.5 mmol);

(2S,3S)-epoxysuccinic acid monoester (564 mg, 3.52 mmol), DIPEA (1.53 mL, 8.8 mmol); EDCI (740 mg, 3.9 mmol); HOBT (520 mg, 3.9 mmol) in DMF (10 ml); afforded the title compound (960 mg, 77.6%) as white solid. $^1$H NMR (CDCl$_3$, 400 MHz): δ 8.78 (s, 1H); 7.65-7.63 (d, 1H, J=1.00 Hz); 7.14 (s, 1H); 7.04 (bs, 1H); 4.80-4.75 (q, 1H); 4.29-4.24 (m, 2H); 3.99-3.97 (q, 2H); 3.72-3.71 (d, 1H, J=1.6 Hz); 3.53-3.52 (d, 1H, J=1.6 Hz); 3.34-3.15 (m, 2H); 2.19 (bs, 1H); 1.33-1.30 (t, 3H). $^{13}$C NMR (CDCl$_3$, 100 MHz): 169.59, 166.49, 166.45, 153.22, 152.42, 116.20, 78.98, 71.59, 62.31, 53.77, 52.81, 52.44, 32.65, 29.20, 14.02. HRMS (ESI) m/z 352.0975 (M+H)+; m/z 350.0836 (M−H)$^+$.

General Procedure for Huisgen Cycloaddition to Give the Intermediate Esters (38-47).

Copper catalyzed Huisgen cycloadditions, a.k.a. "click chemistry", has received much attention in the past decade due to low cross-reactivity with other functional groups, making it the ideal tool for the generation of a library of epoxide incorporating inhibitors. Computational guidance was employed, vide infra, along with a novel click chemistry route to generate a library of triazole incorporating calpain inhibitors (Scheme 6). The key alkynyl intermediate, 37, was functionalized with aryl-azides using a Cu[II] catalyzed Huisgen cycloaddition, with the aid of TBTA to give the corresponding triazole-aryl incorporating epoxyester peptidomimetics (38-47). Ester saponification yielded the desired epoxyacids (49-58) in good yield over 2 steps (85-100%).

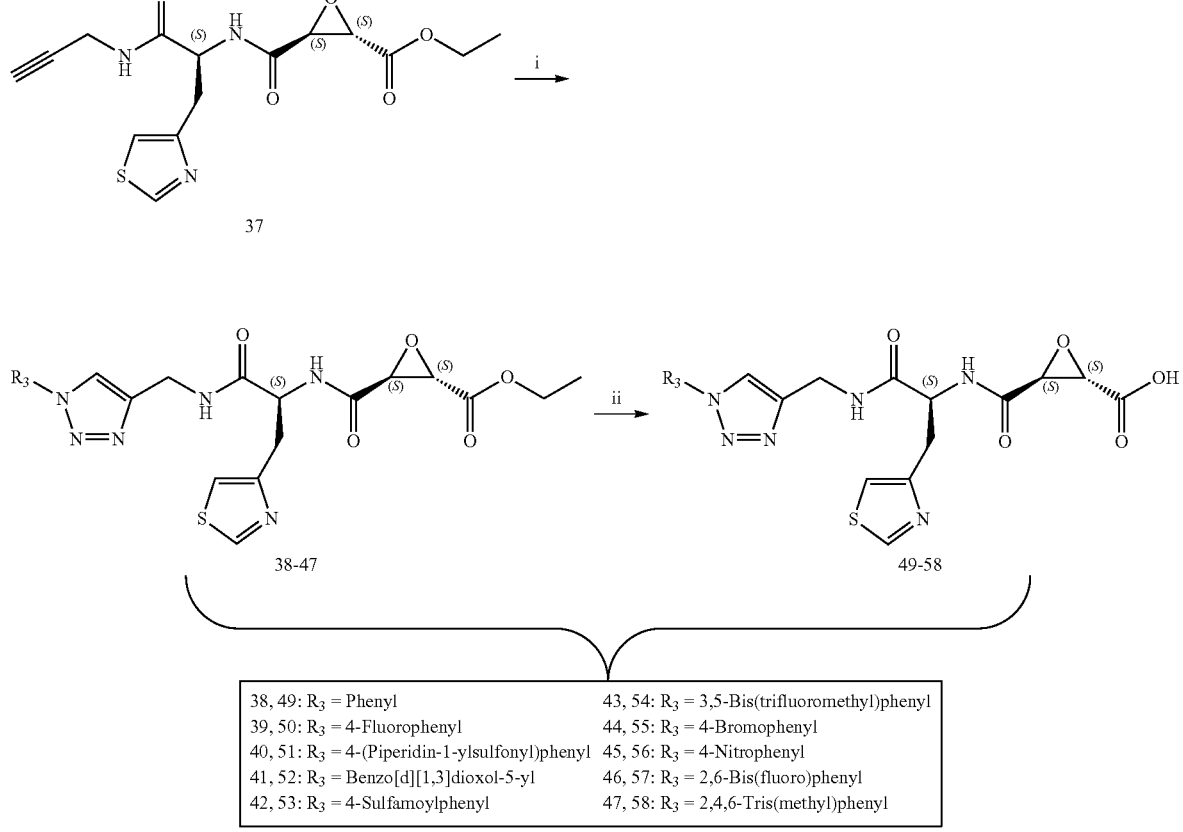

Scheme 6. Click chemistry route to triazole containing calpain inhibitors.

| | |
|---|---|
| 38, 49: R$_3$ = Phenyl | 43, 54: R$_3$ = 3,5-Bis(trifluoromethyl)phenyl |
| 39, 50: R$_3$ = 4-Fluorophenyl | 44, 55: R$_3$ = 4-Bromophenyl |
| 40, 51: R$_3$ = 4-(Piperidin-1-ylsulfonyl)phenyl | 45, 56: R$_3$ = 4-Nitrophenyl |
| 41, 52: R$_3$ = Benzo[d][1,3]dioxol-5-yl | 46, 57: R$_3$ = 2,6-Bis(fluoro)phenyl |
| 42, 53: R$_3$ = 4-Sulfamoylphenyl | 47, 58: R$_3$ = 2,4,6-Tris(methyl)phenyl |

Reagents: i) R$_3$—N$_3$, CuSO$_4$, NaAsc, TBTA, H$_2$O/t-BuOH/EtOH (2:1:1), r.t., 12 h, 90-100%. ii) LiOH, THF/MeOH/H$_2$O, 0° C., 85-100%.

To the appropriate aryl-azide (1.2 eq) and 37 (1.0 eq) were dissolved in t-BuOH/EtOH/H$_2$O (1:1:0.5). CuSO$_4$ (0.2 eq), sodium ascorbate (0.4 eq), and a catalytic amount of TBTA (0.01 eq) were added sequentially and the reaction stirred for 12 h. The resulting precipitate was filtered off, dissolved in CH$_2$Cl$_2$, filtered through celite and concentrated in vacuo to afford the desired product in yields and quantities as follows.

(2S,3S)-ethyl-3-((S)-1-oxo-1-(1-phenyl-1H-1,2,3-triazol-4-yl)methylamino)-3-(thiazol-4-yl)propan-2-ylcarbamoyl)oxirane-2-carboxylate (38)

The general click procedure was used substituting the following quantities: 37 (25.0 mg, 0.08 mmol); phenylazide (9.5 mg, 0.07 mmol); CuSO$_4$ (2.0 mg, 0.01 mmol); NaAsc (6.0 mg, 0.03 mmol); TBTA (5.0 mg, 0.01 mmol); in t-BuOH/EtOH/H$_2$O (2:1:0.5); afforded the 38 as a white solid (32 mg, 92.6%). $^1$H NMR (CDCl$_3$, 400 MHz): δ 8.74-7.73 (d, 1H, J=1.90 Hz), 7.93 (s, 1H); 7.73-7.71 (d, 3H, J=8.68 Hz); 7.55-7.52 (t, 2H); 7.47-7.39 (m, 2H); 7.07-7.06 (d, 1H, J=1.71 Hz); 4.84-4.79 (q, 1H); 4.56-4.54 (d, 2H, J=5.87 Hz); 4.32-4.21 (m, 2H); 3.71-3.70 (d, 1H, J=1.78 Hz); 3.57-3.56 (d, 1H, J=1.78 Hz); 3.39-3.18 (m, 2H); 1.33-1.31 (t, 3H). $^{13}$C NMR (CDCl$_3$, 100 MHz): 170.06, 166.52, 166.39, 153.25, 152.36, 145.11, 136.91, 129.75, 128.81, 120.57, 120.46, 115.97, 62.27, 53.80, 52.79, 52.58, 34.98, 32.76, 14.01.

(2S,3S)-ethyl-3-((S)-1-((1-(4-fluorophenyl)-1H-1,2,3-triazol-4-yl)methylamino)-1-oxo-3-(thiazol-4-yl)propan-2-ylcarbamoyl)oxirane-2-carboxylate (39)

The general click procedure was used substituting the following quantities: 37 (27.3 mg, 0.08 mmol); 1-azido-4-fluorobenzene (10.4 mg, 0.08 mmol); CuSO$_4$ (2.0 mg, 0.01 mmol); NaAsc (6.0 mg, 0.03 mmol); TBTA (5.0 mg, 0.01 mmol); in t-BuOH/EtOH/H$_2$O (2:1:0.5); afforded the 39 as a white solid (35 mg, 92.2%). $^1$H NMR (CDCl$_3$, 400 MHz): δ 8.73-8.72 (d, 1H, J=1.91 Hz); 7.90 (s, 1H); 7.74-7.67 (m, 3H); 7.58-7.55 (t, 1H); 7.24-7.18 (t, 2H); 7.07-7.06 (d, 1H, J=1.71 Hz); 4.84-4.79 (q, 1H); 4.54-4.50 (d, 2H, J=5.90 Hz); 4.29-4.21 (m, 2H); 3.68-3.67 (d, 1H, J=1.78 Hz); 3.53-3.52 (d, 1H, J=1.78 Hz); 3.37-3.18 (m, 2H); 1.30-1.26 (t, 3H). $^{13}$C NMR (CDCl$_3$, 100 MHz): 169.82, 166.17, 166.03, 163.28, 160.81, 152.86, 152.00, 144.94, 132.78, 122.10, 122.01, 120.48, 116.45, 116.22, 115.59, 61.91, 53.43, 52.40, 52.24, 34.55, 32.42, 13.63.

(2S,3S)-ethyl-3-((S)-1-oxo-1-((1-(4-(piperidin-1-ylsulfonyl)phenyl)-1H-1,2,3-triazol-4-yl)methylamino)-3-(thiazol-4-yl)propan-2-ylcarbamoyl)oxirane-2-carboxylate (40)

The general click procedure was used substituting the following quantities: 37 (28.1 mg, 0.08 mmol); 4-piperidinophenylazide (10.7 mg, 0.08 mmol); CuSO$_4$ (3.0 mg, 0.02 mmol); NaAsc (6.0 mg, 0.03 mmol); TBTA (5.0 mg, 0.01 mmol); in t-BuOH/EtOH/H$_2$O (2:1:0.5); afforded the 40 as a white solid (31 mg, 79.8%). $^1$H NMR (CDCl$_3$, 400 MHz):δ 8.76-8.75 (d, 1H, J=1.84 Hz); 8.05 (s, 1H); 7.93 (s, 4H); 7.76-7.74 (d, 1H, J=7.04 Hz); 7.38-7.36 (t, 1H); 7.10-7.09 (d, 1H, J=1.70 Hz); 4.79-4.76 (q, 1H); 4.58-4.55 (q, 2H); 4.30-4.25 (m, 2H); 3.72-3.71 (d, 1H, J=1.78 Hz); 3.55-3.54 (d, 1H, J=1.78 Hz); 3.38-3.17 (abq, 2H); 3.07-304 (t, 3H); 1.75-1.60 (m, 1H); 1.31-1.26 (t, 3H). $^{13}$C NMR (CDCl$_3$, 100 MHz): 170.31, 169.65, 166.52, 166.44, 153.30, 152.40, 152.34, 145.93, 139.64, 136.68, 129.40, 120.61, 120.41, 116.20, 116.02, 79.01, 71.57, 62.31, 53.77, 52.80, 52.45, 46.94, 32.70, 29.19, 25.11, 23.42, 14.02.

(2S,3S)-ethyl-3-((S)-1-(1-(benzo[d][1,3]dioxol-5-yl)-1H-1,2,3-triazol-4-yl)methylamino)-1-oxo-3-(thiazol-4-yl)propan-2-ylcarbamoyl)oxirane-2-carboxylate (41)

The general click procedure was used substituting the following quantities using: 37 (25.0 mg, 0.07 mmol); 5-azidobenzo[d][1,3]dioxole (9.5 mg, 0.07 mmol); CuSO$_4$ (2.0 mg, 0.01 mmol); NaAsc (6.0 mg, 0.03 mmol); TBTA (5.0 mg, 0.01 mmol); in t-BuOH/EtOH/H$_2$O (2:1:0.5); afforded the 41 as a white solid (31 mg, 89.7%). $^1$H NMR (CDCl$_3$, 400 MHz): δ 8.76-8.75 (d, 1H, J=1.86 Hz); 7.79 (s, 1H); 7.73-7.71 (d, 1H, J=7.16 Hz); 7.24-7.21 (dd, 2H); 7.14-7.11 (dd, 1H); 7.08-7.07 (d, 1H, J=1.63 Hz); 6.93-6.91 (d, 1H, J=8.32 Hz); 6.09 (s, 2H); 4.79-4.76 (q, 1H); 4.54-4.53 (d, 2H, J=5.90 Hz); 4.31-4.25 (m, 2H); 3.72-3.71 (d, 1H, J=1.76 Hz); 3.55-3.54 (d, 1H, J=1.76 Hz); 3.38-3.15 (ab, 2H, J=92.8 Hz, 57.57 Hz); 1.35-1.30 (t, 3H). $^{13}$C NMR (CDCl$_3$, 100 MHz): 169.49, 169.05, 164.22, 155.01, 153.30, 148.84, 147.92, 148.27, 130.98, 121.72, 116.26, 114.17, 109.12, 102.60, 102.33, 62.14, 52.95, 52.54, 51.90, 34.78, 33.49, 14.23.

(2S,3S)-ethyl-3-((S)-1-oxo-1-((1-(4-sulfamoylphenyl)-1H-1,2,3-triazol-4-yl)methylamino)-3-(thiazol-4-yl)propan-2-ylcarbamoyl)oxirane-2-carboxylate (42)

The general click procedure was used substituting the following quantities using: 37 (109.0 mg, 0.31 mmol); 4-azidobenzenesulfonamide (61.5 mg, 0.31 mmol); CuSO$_4$ (10.0 mg, 0.06 mmol); NaAsc (20.0 mg, 0.03 mmol); TBTA (10.0 mg, 0.02 mmol); in t-BuOH/EtOH/H$_2$O (4:4:2); afforded the 42 as a white solid (119 mg, 69.8%). $^1$H NMR (CDCl$_3$, 400 MHz): δ 8.93 (s, 1H); 8.45 (s, 1H); 8.19-8.05 (q, 4H); 7.33 (s, 1H); 4.81-4.77 (t, 1H); 4.57-4.48 (q, 2H); 4.28-4.23 (q, 2H); 3.64 (s, 1H); 3.50 (s, 1H); 3.40-3.21 (m, 2H); 1.28-1.23 (t, 3H). $^{13}$C NMR (MeOD-d$^4$, 100 MHz): 170.94, 166.80, 166.72, 153.45, 151.92, 145.70, 143.49, 138.85, 127.31, 120.74, 119.76, 115.56, 61.42, 52.72, 52.67, 51.47, 33.93, 31.91, 12.52.

(2S,3S)-ethyl-3-((S)-1-((1-(3,5-bis(trifluoromethyl)phenyl)-1H-1,2,3-triazol-4-yl)methylamino)-1-oxo-3-(thiazol-4-yl)propan-2-ylcarbamoyl)oxirane-2-carboxylate (43)

The general click procedure was used substituting the following quantities using: 37 (93.7 mg, 0.27 mmol); 1-azido-3,5-bis(trifluoromethyl)benzene (82.5 mg, 0.32 mmol); CuSO$_4$ (0.6 mg, 0.01 mmol); NaAsc (3.5 mg, 0.02 mmol); TBTA (15.0 mg, 0.03 mmol); in t-BuOH/EtOH/H$_2$O (4:4:2) with an additional 3 drops of DMF; afforded the 43 as a white solid (142 mg, 87.8%). $^1$H NMR (CDCl$_3$, 400 MHz): δ 8.77 (s, 1H); 8.25 (s, 2H); 8.09 (s, 1H); 7.96 (s, 1H); 7.77-7.75 (d, 1H, J=7.09 Hz); 7.34-7.32 (t, 1H); 7.11 (s, 1H); 4.81-4.76 (q, 1H); 4.59-4.57 (d, 2H, J=5.90 Hz); 4.31-4.25 (m, 2H); 3.72-3.711 (d, 1H, J=1.64 Hz); 3.55-3.54 (d, 1H, J=1.64 Hz); 3.41-3.17 (m, 2H); 1.01-0.99 (t, 3H). $^{13}$C NMR (DMSO-d$^6$, 100 MHz): 170.62, 167.49, 165.37, 154.06, 153.24, 146.92, 138.31, 124.57, 122.37, 121.85, 121.09, 116.21, 61.97, 53.44, 52.97, 51.74, 34.64, 33.49, 14.29.

(2S,3S)-ethyl-3-((S)-1-((1-(4-bromophenyl)-1H-1,2,3-triazol-4-yl)methylamino)-1-oxo-3-(thiazol-4-yl)propan-2-ylcarbamoyl)oxirane-2-carboxylate (44)

The general click procedure was used substituting the following quantities using: 37 (60 mg, 0.17 mmol); 1-azido-4-bromobenzene (51 mg, 0.26 mmol); CuSO$_4$ (4.4 mg, 0.03 mmol); NaAsc (22 mg, 0.11 mmol); TBTA (20.0 mg, 0.04 mmol); in t-BuOH/EtOH/H$_2$O (2:2:1); afforded the 44 as a white solid (40 mg, 42.6%). $^1$H NMR (DMSO-d$^6$, 400 MHz): δ 9.00-8.99 (d, 1H, J=1.66 Hz); 8.74-8.71 (t, 1H); 8.63-8.61 (d, 1H, J=8.22 Hz); 8.54 (s, 1H); 7.60-7.56 (d, 2H, J=14.85 Hz); 7.345-7.341 (d, 1H, J=1.63 Hz); 7.11-7.07 (d, 2H, J=14.85 Hz); 4.69-4.66 (q, 1H); 4.40-4.38 (d, 2H, J=5.59 Hz); 4.20-4.13 (m, 2H); 3.66-3.66 (d, 1H, J=1.73 Hz); 3.52-3.51 (d, 1H, J=1.73 Hz); 3.33-3.12 (m, 2H); 1.23-1.20 (t, 3H). $^{13}$C NMR (100 MHz, DMSO-d$^6$): 170.57, 167.51, 165.36, 154.07, 153.27, 146.56, 139.39, 136.25, 122.30, 121.54, 117.51, 116.23, 61.97, 53.46, 52.99, 51.76, 34.75, 33.50, 14.32.

(2S,3S)-ethyl-3-((S)-1-((1-(4-nitrophenyl)-1H-1,2,3-triazol-4-yl)methylamino)-1-oxo-3-(thiazol-4-yl)propan-2-ylcarbamoyl)oxirane-2-carboxylate (45)

The general click procedure was used substituting the following quantities using: 37 (60 mg, 0.17 mmol); 1-azido-4-nitrobenzene (42 mg, 0.26 mmol); CuSO$_4$ (4.4 mg, 0.03 mmol); NaAsc (22 mg, 0.11 mmol); TBTA (20.0 mg, 0.04 mmol); in t-BuOH/EtOH/H$_2$O (2:2:1); afforded the 45 as an orange solid (40 mg, 45.6%). $^1$H NMR (DMSO-d, 400 MHz): δ 9.00-8.99 (d, 1H, J=1.8 Hz); 8.77-8.74 (t, 1H); 8.73 (s, 1H); 8.63-8.61 (d, 1H, J=8.17 Hz); 8.47-8.44 (d, 2H, J=9.13 Hz); 8.21-8.19 (d, 2H, J=9.13 Hz); 7.36 (d, 1H, J=1.78 Hz); 4.71-4.65 (q, 1H); 4.42-4.40 (d, 2H, J=5.50 Hz); 4.20-4.09 (m, 2H); 3.66-3.65 (d, 1H, J=1.75 Hz); 3.52-3.51 (d, 1H, J=1.75 Hz); 3.28-3.06 (m, 2H); 1.22-1.17 (t, 3H). $^{13}$C NMR (CDCl$_3$, 100 MHz): 170.25, 167.14, 165.00, 153.70, 152.87, 146.77, 146.68, 140.89, 125.70, 121.59, 120.42, 115.86, 61.60, 53.09, 52.61, 51.40, 34.32, 33.12, 13.94.

(2S,3S)-ethyl-3-((S)-1-((1-(2,6-difluorophenyl)-1H-1,2,3-triazol-4-yl)methylamino)-1-oxo-3-(thiazol-4-yl)propan-2-ylcarbamoyl)oxirane-2-carboxylate (46)

The general click procedure was used substituting the following quantities using: 37 (48 mg, 0.14 mmol); 2-azido-1,3-difluorobenzene (24 mg, 0.15 mmol); CuSO$_4$ (3.5 mg, 0.02 mmol); NaAsc (18 mg, 0.09 mmol); TBTA (12 mg, 0.01 mmol); in t-BuOH/EtOH/H$_2$O (1:1:0.5); afforded 46 as a white solid (20 mg, 31.6%). $^1$H NMR (DMSO-d$^6$, 400 MHz): δ 8.74-8.73 (d, 1H, J=1.79 Hz); 7.74-7.72 (m, 2H); 7.55-7.45 (m, 1H); 7.34-7.32 (m, 1H); 7.17-7.13 (t, 2H); 7.04-7.03 (d, 1H, J=1.72 Hz); 4.82-4.80 (q, 1H); 4.57-4.56 (d, 2H, J=5.97 Hz); 4.29-4.24 (m, 2H); 3.71-3.70 (d, 1H, J=1.78 Hz); 3.55-3.54 (d, 1H, J=1.78 Hz); 3.35-3.18 (m, 2H); 1.33-1.30 (t, 3H). $^{13}$C NMR (CDCl$_3$, 100 MHz): 170.16, 166.65, 166.30, 158.01, 155.46, 153.29, 152.24, 144.36, 131.48, 129.14, 125.10, 116.01, 112.64, 62.24, 53.81, 52.74, 52.62, 34.74, 32.91, 13.99.

(2S,3S)-ethyl-3-((S)-1-((1-mesityl-1H-1,2,3-triazol-4-yl)methylamino)-1-oxo-3-(thiazol-4-yl)propan-2-ylcarbamoyl)oxirane-2-carboxylate (47)

The general click procedure was used substituting the following quantities using: 37 (48 mg, 0.14 mmol); 2-azido-1,3-difluorobenzene (24 mg, 0.15 mmol); CuSO$_4$ (3.5 mg, 0.02 mmol); NaAsc (18 mg, 0.09 mmol); TBTA (12 mg, 0.01 mmol); in t-BuOH/EtOH/H$_2$O (1:1:0.5); afforded 47 as a white solid (30 mg, 42.8%). $^1$H NMR (400 MHz, DMSO-d$^6$): δ 8.79-8.74 (d, 1H, J=1.79 Hz); 7.68-7.64 (m, 2H); 7.50 (s, 1H); 7.36-7.34 (d, 2H); 7.28-7.26 (d, 2H); 7.15-7.10 (m, 2H), 6.98 (s, 1H); 5.50 (s, 1H); 4.83-4.78 (m, 1H); 4.59-4.58 (d, 1H); 4.29-4.25 (m, 2H); 3.99-3.97 (q, 1H); 3.81 (s, 3H); 3.69-3.68 (m, 3H); 3.55-3.54 (d, 1H); 3.37-3.19 (abq, 2H); 2.35 (s, 3H); 1.93 (s, 3H) 1.33-1.29 (t, 3H). $^{13}$C NMR (DMSO-d$^6$, 100 MHz): 169.25, 165.62, 153.65, 152.98, 144.93, 140.11, 134.51, 134.50, 128.12, 124.69, 115.88, 63.51, 52.69, 52.78, 51.98, 48.66, 34.54, 33.10, 20.69, 16.89, 13.52.

(2S,3S)-ethyl-3-((S)-1-((1-(4-aminophenyl)-1H-1,2,3-triazol-4-yl)methylamino)-1-oxo-3-(thiazol-4-yl)propan-2-ylcarbamoyl)oxirane-2-carboxylate (48)

The general click procedure was used substituting the following quantities using: 37 (29.5 mg, 0.084 mmol); 4-azidoaniline (11.3 mg, 0.084 mmol); CuSO$_4$ (3.0 mg, 0.02 mmol); NaAsc (7.0 mg, 0.03 mmol); TBTA (5.0 mg, 0.009 mmol); in t-BuOH/EtOH/H$_2$O (2:1:0.5); afforded 48 as a white solid (35 mg, 85.9%). $^1$H NMR (400 MHz, CDCl$_3$): d=8.73 (s, 1H); 8.18 (bs, 1H); 7.86 (s, 1H); 7.85-7.83 (d, 1H, J=8.17 Hz); 7.46-7.35 (d, 2H, J=8.58 Hz); 7.06 (s, 1H); 6.80-6.78 (d, 2H, J=8.62 Hz), 4.78-4.77 (q, 1H); 4.48-4.47 (d, 2H, J=5.60 Hz); 4.29-4.23 (m, 2H); 3.65-3.64 (d, 1H, J=1.59 Hz); 3.51-3.51 (d, 1H, J=1.59 Hz); 3.41-3.24 (m, 2H): 1.33-1.30 (t, 3H). $^{13}$C NMR (100 MHz, CDCl$_3$): 169.12, 166.74, 166.14, 153.09, 151.8, 147.32, 144.44, 127.90, 121.86, 120.73, 115.77, 115.0, 62.07, 53.39, 52.23, 34.51, 34.39, 32.70, 13.6.

(2S,3S)-3-((S)-1-oxo-1-((1-phenyl-1H-1,2,3-triazol-4-yl)methylamino)-3-(thiazol-4-yl)propan-2-ylcarbamoyl)oxirane-2-carboxylic acid (49)

Followed general procedure using: the corresponding peptidomimetic epoxide ethyl ester 38 (23 mg, 0.47 mmol); LiOH (1.2 mg, 0.05 mmol); after extraction afforded the desired product as a white solid (18 mg, 84.9%). $^1$H NMR (DMSO-d$_6$, 400 MHz): δ9.00-8.99 (d, 1H, J=1.76 Hz); 8.73-8.70 (t, 1H); 8.58-8.56 (d, 1H, J=8.24 Hz); 8.50 (s, 1H); 7.87-7.85 (d, 2H, J=7.76 Hz); 7.61-7.49 (m, 3H); 7.344-7.341 (d, 1H, J=1.21 Hz); 4.69-4.66 (q, 1H); 4.41-4.39 (d, 2H, J=5.49 Hz); 3.59-3.59 (d, 1H, J=1.58 Hz); 3.35-3.10 (m, 3H). $^{13}$C NMR (DMSO-d$^6$, 100 MHz): 170.62, 169.06, 165.75, 154.05, 153.31, 146.36, 137.07, 130.38, 129.06, 131.48, 120.41, 116.19, 53.25, 52.96, 51.90, 34.80, 29.42. HRMS-ESI: m/z [M+H$^+$] calculated for C$_{18}$H$_{16}$N$_6$O$_5$S: 443.1137, observed: m/z 443.1135 (M+H$^+$). HPLC Method 2: R$_t$=16.7 min; purity=97.9%.

(2S,3S)-3-((S)-1-((1-(4-fluorophenyl)-1H-1,2,3-triazol-4-yl)methylamino)-1-oxo-3-(thiazol-4-yl)propan-2-ylcarbamoyl)oxirane-2-carboxylic acid (50)

Followed general procedure using: the corresponding peptidomimetic epoxide ethyl ester 39 (25 mg, 0.51 mmol); LiOH (1.3 mg, 0.06 mmol); after extraction afforded the desired product as a white solid (18 mg, 76.2%). $^1$H NMR (DMSO-d$_6$, 400 MHz): δ 8.98 (s, 1H); 8.72-8.70 (t, 1H); 8.57-8.55 (d, 1H, J=8.06); 8.48 (s, 1H); 7.93-7.90 (m, 2H); 7.48-7.44 (t, 2H); 7.34 (s, 1H); 4.70-4.65 (q, 1H); 4.40-4.38 (d, 2H; J=5.52); 3.66 (s, 1H); 3.54-3.06 (m, 3H). $^{13}$C NMR (DMSO-d⁶, 100 MHz): 170.62, 165.75, 163.24, 160.80, 154.06, 153.32, 146.40, 133.62, 122.81, 122.72, 121.76, 117.33, 117.10, 53.24, 53.01, 52.94, 34.77, 33.50. HRMS-ESI: m/z [M+H⁺] calculated for $C_{19}H_{17}FN_6O_5S$: 461.1043, observed: m/z 461.1049 (M+H⁺); HPLC Method 2: $R_t$=17.9 min; purity=97.2%.

(2S,3S)-3-((S)-1-oxo-1-((1-(4-(piperidin-1-ylsulfonyl)phenyl)-1H-1,2,3-triazol-4-yl)methylamino)-3-(thiazol-4-yl)propan-2-ylcarbamoyl)oxirane-2-carboxylic acid (51)

Followed general procedure using: the corresponding peptidomimetic epoxide ethyl ester 40 (26 mg, 0.42 mmol); LiOH (1.0 mg, 0.04 mmol); after extraction afforded the desired product as a white solid (12 mg, 48.3%). ¹H NMR (Acetone-d⁶, 400 MHz): δ8.98 (bs, 1H); 8.48 (s, 1H); 8.16-8.12 (d, 2H, 8.48); 8.02-8.00 (d, 2H, J=8.48 Hz); 7.37 (bs, 1H); 4.81 (bs, 1H); 4.52 (s, 2H); 3.85-3.79 (m, 4H); 3.61 (s, 1H); 3.55 (s, 1H); 1.82-1.60 (m, 6H). ¹³C NMR (Acetone-d⁶, 100 MHz): 170.07, 169.01, 165.12, 153.52, 139.36, 136.19, 129.47, 120.84, 120.21, 107.39, 107.25, 66.62, 53.44, 52.80, 52.77, 46.83, 32.52, 30.07, 25.02, 23.13. HRMS-ESI: m/z [M+H⁺] calculated for $C_{24}H_{27}N_7O_7S_2$: 590.6440, observed: m/z 590.1050 (M+H⁺); HPLC Method 2: $R_t$=21.7 min; purity=96.3%.

(2S,3S)-3-((S)-1-((1-(benzo[d][1,3]dioxol-5-yl)-1H-1,2,3-triazol-4-yl)methylamino)-1-oxo-3-(thiazol-4-yl)propan-2-ylcarbamoyl)oxirane-2-carboxylic acid (52)

Followed general procedure using: the corresponding peptidomimetic epoxide ethyl ester 41 (10 mg, 0.16 mmol); LiOH (0.35 mg, 0.02 mmol); after extraction afforded the desired product as a white solid (7 mg, 73.1%). ¹H NMR (DMSO-d, 400 MHz): δ 9.00-8.99 (d, 1H, J=1.88 Hz); 8.71-8.68 (t, 1H); 8.57-8.55 (d, 1H, J=8.28 Hz); 8.38 (s, 1H); 7.46-7.45 (d, 1H, J=2.15 Hz); 7.33-7.31 (m, 2H); 7.11 (s, 1H); 7.09 (s, 1H); 6.15 (s, 2H); 4.67-4.65 (m, 1H); 4.38-4.36 (d, 2H); 3.60-3.58 (d, 1H, J=1.72 Hz); 3.50-3.17 (m, 3H). ¹³C NMR (DMSO-d⁶, 100 MHz): 170.59, 169.06, 165.75, 154.05, 153.31, 148.65, 147.81, 146.07, 131.53, 121.69, 116.19, 114.15, 109.11, 102.58, 102.33, 53.24, 52.94, 51.90, 34.78, 33.49. HRMS-ESI: m/z [M+H⁺] calculated for $C_{20}H_{18}N_6O_7S$: 487.4643, observed: m/z 487.1050 (M+H⁺); HPLC Method 2: $R_t$=18.1 min; purity=97.7%.

(2S,3S)-3-((S)-1-oxo-1-((1-(4-sulfamoylphenyl)-1H-1,2,3-triazol-4-yl)methylamino)-3-(thiazol-4-yl)propan-2-ylcarbamoyl)oxirane-2-carboxylic acid (53)

Followed general procedure using: the corresponding peptidomimetic epoxide ethyl ester 42 (30 mg, 0.55 mmol); LiOH (1.3 mg, 0.055 mmol); product goes into aqueous layer during work up. Aqueous layer washed with $CH_2Cl_2$ and lyophilized to give the desired product as a white solid (8 mg, 45.1%). ¹H NMR (DMSO-d⁶, 400 MHz): δ 9.00-8.99 (d, 1H, J=1.92 Hz); 8.79-8.76 (t, 1H); 8.70-8.68 (d, 1H, J=8.0 Hz); 8.66 (s, 1H); 8.12-8.01 (m, 4H); 7.55 (s, 2H); 7.36 (s, 1H); 4.70-4.65 (m, 1H); 4.41-4.40 (d, 2H, J=5.20 Hz); 3.61 (s, 1H); 3.44-3.10 (m, 3H). ¹³C NMR (DMSO-d⁶, 100 MHz): 172.25, 170.66, 169.06, 165.74, 154.10, 152.52, 138.29, 146.80, 144.19, 128.01, 121.75, 120.59, 116.29, 53.25, 52.98, 51.84, 49.01, 33.43. HRMS-ESI: m/z [M+H⁺] calculated for $C_{19}H_{19}N_7O_7S_2$: 522.0865, observed: m/z 522.0858 (M+H⁺); HPLC method 2: $R_t$=14.8 min; purity=95.1%.

(2S,3S)-3-((S)-1-((1-(3,5-bis(trifluoromethyl)phenyl)-1H-1,2,3-triazol-4-yl)methylamino)-1-oxo-3-(thiazol-4-yl)propan-2-ylcarbamoyl)oxirane-2-carboxylic acid (54)

Followed general procedure using: the corresponding peptidomimetic epoxide ethyl ester 43 (94 mg, 0.15 mmol); LiOH (3.7 mg, 0.15 mmol); after extraction afforded the desired product as a white solid (72 mg, 80.3%). ¹H NMR (DMSO-d⁶, 400 MHz): δ 8.99-8.98 (d, 1H, J=1.92 Hz); 8.92 (s, 1H); 8.79-8.77 (t, 1H); 8.63 (s, 2H); 8.57-8.55 (d, 1H, J=8.27 Hz); 8.27 (s, 1H); 7.34-7.33 (d, 1H, J=1.85 Hz); 4.71-4.66 (m, 1H); 4.43-4.42 (d, 2H, J=5.67 Hz); 3.58-3.57 (d, 1H, J=1.73 Hz); 3.36-3.35 (d, 1H, J=1.70 Hz); 3.28-3.10 (m, 2H). ¹³C NMR (DMSO-d⁶, 100 MHz): 170.67, 169.07, 165.80, 154.06, 153.29, 146.93, 138.32, 132.48, 132.14, 122.38, 121.11, 116.18, 53.22, 52.90, 51.96, 34.64, 33.51. HRMS-ESI: m/z [M+H⁺] calculated for $C_{21}H_{16}F_6N_6O_5S$: 579.4443, observed: m/z 579.0890 (M+H⁺); m/z 577.0775 (M−H⁺). HPLC method 2: $R_t$=24.5 min; purity=95.3%.

(2S,3S)-3-((S)-1-((1-(4-bromophenyl)-1H-1,2,3-triazol-4-yl)methylamino)-1-oxo-3-(thiazol-4-yl)propan-2-ylcarbamoyl)oxirane-2-carboxylic acid (55)

Followed general procedure using: the corresponding peptidomimetic epoxide ethyl ester 44 (25 mg, 0.04 mmol); LiOH (1.1 mg, 0.04 mmol); after extraction afforded the desired product as a white solid (18 mg, 75.9%). ¹H NMR (DMSO-d⁶, 400 MHz): δ 8.99-8.98 (d, 1H, J=1.87 Hz); 8.74-8.71 (t, 1H); 8.58-8.56 (d, 1H, J=8.27 Hz); 8.54 (s, 1H); 7.86-7.79 (q, 4H); 7.34-7.33 (d, 1H, J=1.75 Hz); 4.70-4.65 (q, 1H); 4.40-4.38 (d, 2H, J=5.59 Hz); 3.60-3.59 (d, 1H, J=1.77 Hz); 3.38-3.37 (d, 1H, J=1.77 Hz); 3.28-3.10 (m, 2H). ¹³C NMR (DMSO-d₆, 100 MHz):170.62, 169.08, 165.74, 154.06, 153.29, 146.57, 136.25, 133.27, 122.31, 121.67, 121.54, 116.20, 53.25, 52.94, 51.89, 34.76, 33.49. HRMS-ESI: m/z [M+H⁺] calculated for $C_{19}H_{17}BrN_6O_5S$: 521.34, observed: m/z 523.0229 (M+H⁺); m/z 519.0123 (M−H⁺); HPLC Method 2: $R_t$=21.8 min; 97.2%.

(2S,3S)-3-((S)-1-((1-(4-nitrophenyl)-1H-1,2,3-triazol-4-yl)methylamino)-1-oxo-3-(thiazol-4-yl)propan-2-ylcarbamoyl)oxirane-2-carboxylic acid (56)

Followed general procedure using: the corresponding peptidomimetic epoxide ethyl ester 45 (27 mg, 0.05 mmol); LiOH (1.2 mg, 0.05 mmol); after extraction afforded the desired product as a white solid (20 mg, 78.3%). ¹H NMR (DMSO-d₆, 400 MHz): δ 9.00-8.99 (d, 1H, J=1.79 Hz); 8.74-8.71 (t, 1H); 8.59 (s, 1H); 8.48-8.47 (d, 1H, J=8.42 Hz); 8.47-8.45 (d, 2H, J=9.15 Hz); 8.21-8.19 (d, 2H, J=9.15 Hz); 7.34-7.33 (d, 1H, J=1.78 Hz); 4.69-4.66 (q, 1H); 4.42-4.41 (d, 2H, J=5.60 Hz); 3.60-3.59 (d, 1H, J=1.79 Hz); 3.50-3.10 (m, 3H). ¹³C NMR (DMSO-d⁶, 100 MHz):170.68, 169.07, 165.75, 154.10, 153.25, 147.11, 147.05, 141.26, 126.08, 121.95, 120.94, 116.23, 53.24, 52.95, 51.85, 34.69, 33.44. HRMS-ESI: m/z [M+H⁺] calculated for $C_{19}H_{17}N_7O_7S$: 488.4543, observed: m/z 488.0986 (M+H⁺); m/z 486.0864 (M−H⁺). HPLC Method 2: $R_t$=20.4 min; 93.4%.

(2S,3S)-3-((S)-1-((1-(2,6-difluorophenyl)-1H-1,2,3-triazol-4-yl)methylamino)-1-oxo-3-(thiazol-4-yl)propan-2-ylcarbamoyl)oxirane-2-carboxylic acid (57)

Followed general procedure using: the corresponding peptidomimetic epoxide ethyl ester 46 (24 mg, 0.05 mmol); LiOH (1.1 mg, 0.05 mmol); after extraction afforded the desired product as a white solid (13 mg, 57.3%). $^1$H NMR (DMSO-$d_6$, 400 MHz): δ 9.00-8.99 (d, 1H, J=1.90 Hz); 8.78-8.76 (t, 1H); 8.60-8.58 (d, 1H, J=8.29 Hz); 8.27 (s, 1H); 7.77-7.69 (m, 1H); 7.49-7.45 (t, 2H); 7.36-7.27 (m, 2H); 4.71-4.65 (m, 1H); 4.44-4.42 (d, 2H, J=5.63 Hz); 3.598-3.593 (d, 1H, J=1.78); 3.360-3.355 (d, 1H, J=1.78); 3.27-3.22 (m, 2H). $^{13}$C NMR (DMSO-$d_6$, 100 MHz): 170.69, 169.07, 165.69, 158.07, 158.04, 155.56, 155.53, 154.05, 153.31, 145.67, 136.62, 129.17, 128.48, 126.17, 116.17, 53.23, 52.93, 51.83, 34.67, 33.51. HRMS-ESI: m/z [M+H$^+$] calculated for $C_{19}H_{16}F_2N_6O_5S$: 479.4343, observed: m/z 479.0960 (M+H$^+$): HPLC Method 2: $R_t$=17.32 min; 95.9%.

(2S,3S)-3-((S)-1-((1-mesityl-1H-1,2,3-triazol-4-yl)methylamino)-1-oxo-3-(thiazol-4-yl)propan-2-ylcarbamoyl)oxirane-2-carboxylic acid (58)

Followed general procedure using: the corresponding peptidomimetic epoxide ethyl ester 47 (24 mg, 0.05 mmol); LiOH (1.1 mg, 0.05 mmol); after extraction afforded the desired product as a white solid (15 mg, 66.1%). $^1$H NMR (DMSO-$d_6$, 400 MHz): δ 8.98-8.97 (d, 1H, J=1.87 Hz); 8.72-8.70 (t, 1H, J=11.2 Hz); 8.55-8.53 (d, 1H, J=8.23 Hz); 7.93 (s, 1H); 7.34 (s, 1H); 7.08 (s, 1H); 4.68-4.63 (m, 1H); 4.42-4.40 (d, 2H, J=5.50 Hz); 3.61-3.50 (m, 4H); 2.32 (s, 3H); 1.86 (s, 6H). $^{13}$C NMR (DMSO-$d_6$, 100 MHz):170.29, 165.60, 153.65, 152.98, 144.93, 139.46, 134.51, 133.50, 128.90, 124.69, 115.78, 52.79, 52.58, 48.66, 34.54, 33.10, 20.69, 16.89. HRMS-ESI: m/z [M+H$^+$] calculated for $C_{22}H_{24}N_6O_5S$: 485.5343, observed: m/z 485.1622 (M+H$^+$): m/z 483.1600 (M−H$^+$); HPLC Method 2: $R_t$=23.6 min; 97.4%.

Example 3: Calpain Inhibition by 1st Generation Inhibitors: P3/P4 Cap Group Selection Calpain activity was measured using full-length human Cal1 in the presence of a FRET substrate. $IC_{50}$ values were approximated by co-incubation of varying concentrations of the appropriate inhibitor (10, 100, 500, 1000 nM) in the presence of the FRET substrate (DABCYL)TPLK-SPPSPR-(EDANS) (SEQ ID NO: 5) and activation buffer. Fluorescence was measured following a 20 min incubation and % inhibition calculated by normalizing to control experiments containing no inhibitor. A peptide inhibitor, Z-LLY-FMK (SEQ ID NO: 6), was used as a positive control. In the case of potent inhibitors, the concentration-response was extended to include 1, 10, 50, 100, 250, and 500 nM inhibitor.

TABLE 2

Epoxysuccinate structures and inhibition data.

| No | Structure | Cal I $IC_{50}$ | Relative selectivity for Cal I E64 = 1.0$^f$ | $LD_{50}$ ≥ 50 μM primary neurons |
|---|---|---|---|---|
| 59 | 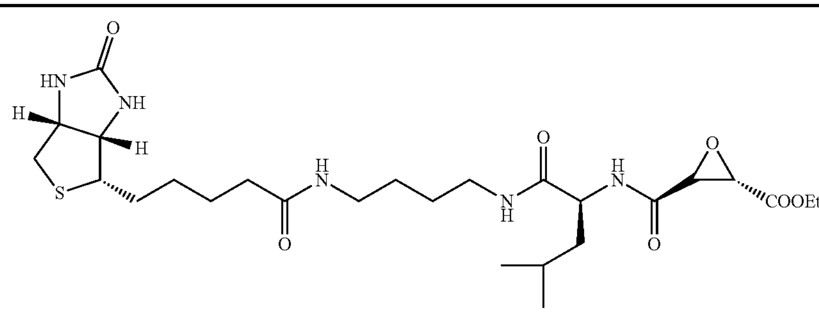 | >1 μM | | |
| 26 | 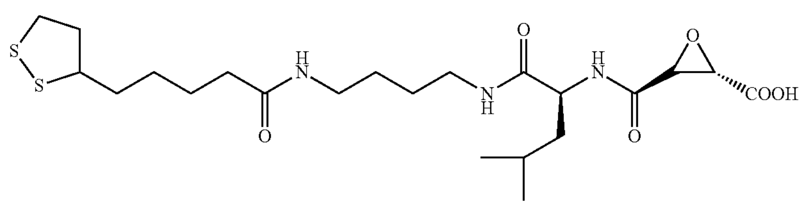 | 150 nM | 1.6 | YES |
| E64 | 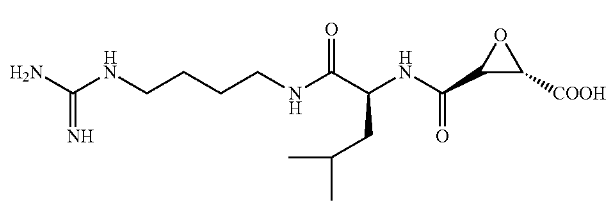 | 100 nM | 1.0 | YES |

TABLE 2-continued

Epoxysuccinate structures and inhibition data.

| No | Structure | Cal I IC$_{50}$ | Relative selectivity for Cal I E64 = 1.0[f] | LD$_{50}$ ≥ 50 μM primary neurons |
|---|---|---|---|---|
| 27 | 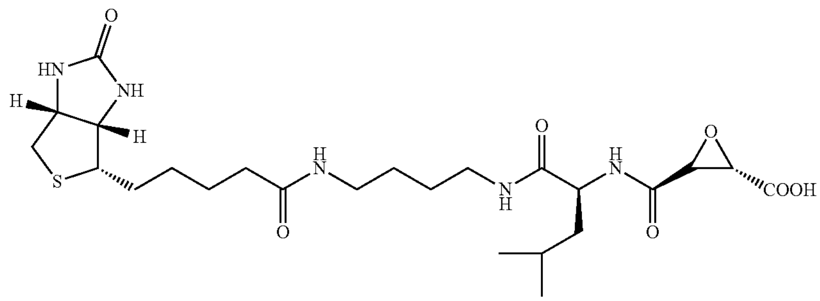 | 150 nM | | |
| 60 | 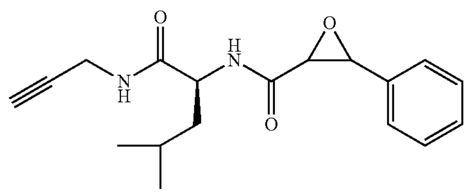 [SMILES: C#CCNC(=O)[C@H](CC(C)C)NC(=O)C1OC1c1ccccc1] | >1 μM | | |
| 61 | 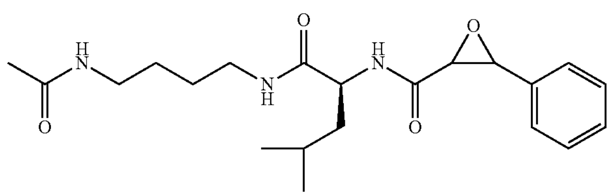 [SMILES: CC(=O)NCCCCNC(=O)[C@H](CC(C)C)NC(=O)C1OC1c1ccccc1] | ~1 μM | 0.3 | YES |
| 62 | 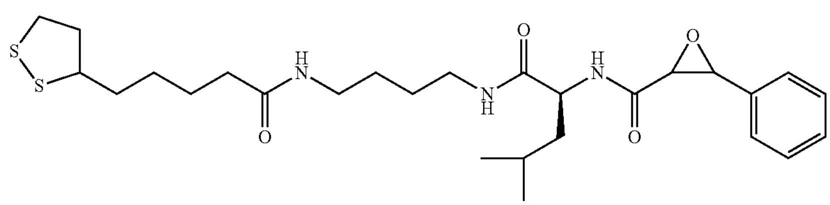 [SMILES: CC(C)C[C@H](NC(=O)C1OC1c1ccccc1)C(=O)NCCCCNC(=O)CCCCC1CCSS1] | >1 μM | | |
| 63 | 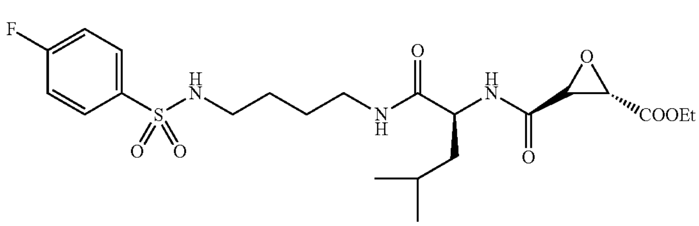 | >1 μM | | |
| 25 | 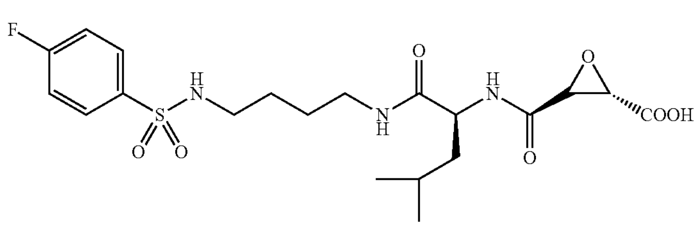 | 100 nM | 0.9 | YES |

TABLE 2-continued
Epoxysuccinate structures and inhibition data.
| No | Structure | Cal I IC$_{50}$ | Relative selectivity for Cal I E64 = 1.0$^r$ | LD$_{50}$ ≥ 50 μM primary neurons |
|---|---|---|---|---|
| 64 | 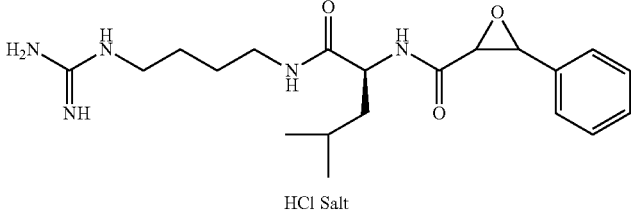 [SMILES: CC(C)C[C@H](NC(=O)C1OC1c1ccccc1)C(=O)NCCCCNC(=N)N] HCl Salt | | | |
| 65 | 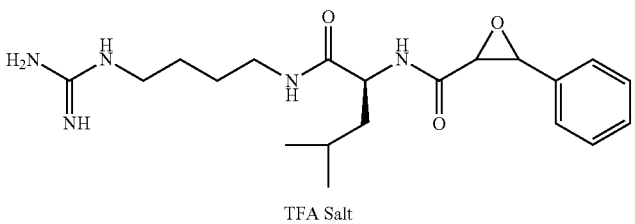 [SMILES: CC(C)C[C@H](NC(=O)C1OC1c1ccccc1)C(=O)NCCCCNC(=N)N] TFA Salt | >1 μM | | |
| 66 | 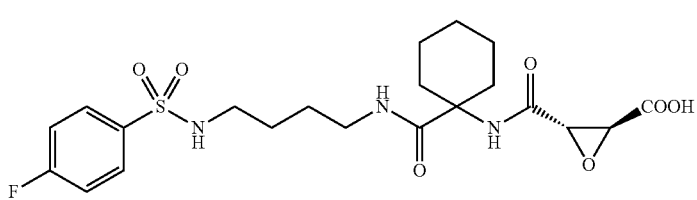 [SMILES: O=C(O)[C@H]1O[C@@H]1C(=O)NC1(C(=O)NCCCCNS(=O)(=O)c2ccc(F)cc2)CCCCC1] | 1 μM | | |
| 67 | 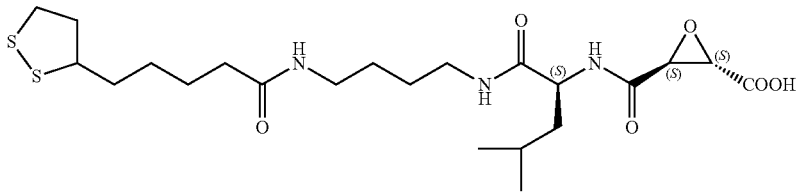 | 150 nM | | |
| 68 | 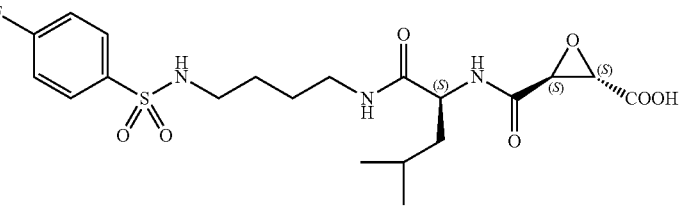 | 100 nM | | |
| 69 | 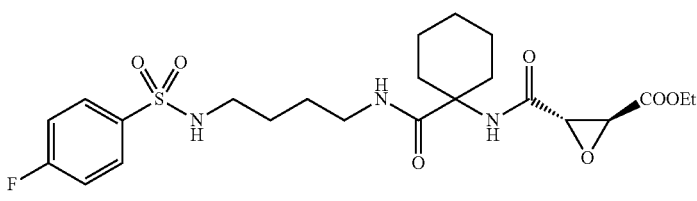 [SMILES: CCOC(=O)[C@H]1O[C@@H]1C(=O)NC1(C(=O)NCCCCNS(=O)(=O)c2ccc(F)cc2)CCCCC1] | >1 μM | | |
| 70 | 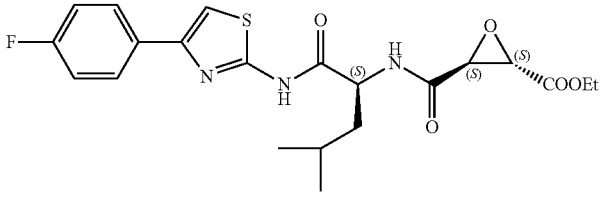 | >1 μM | | |

TABLE 2-continued

Epoxysuccinate structures and inhibition data.

| No | Structure | Cal I IC$_{50}$ | Relative selectivity for Cal I E64 = 1.0[f] | LD$_{50}$ ≥ 50 μM primary neurons |
|---|---|---|---|---|
| 71 | [structure: 4-fluorophenyl-thiazole-N(Me)-(S)-Leu-NH-(S,S)-epoxide-COOEt] | >1 μM | | |
| 72 | [structure: 4-fluorophenyl-thiazole-N(Me)-(S)-Leu-NH-(S,S)-epoxide-COOH] | 200 nM | | |
| 24a | [structure: 4-fluorophenyl-thiazole-NH-(S)-Leu-NH-(S,S)-epoxide-COOH] | 30 nM | | |
| 73 | [structure: isopropyl-NH-(R,R)-epoxide-COOEt] | >1 μM | | |
| 74 | [structure: isopropyl-NH-(R,R)-epoxide-COOH] | >1 μM | | |
| 75 | [structure: 4-fluorophenyl-thiazole-NH-(S)-Leu-NH-(R,R)-epoxide-COOEt] | >1 μM | | |
| 24b | [structure: 4-fluorophenyl-thiazole-NH-(S)-Leu-NH-(R,R)-epoxide-COOH] | 175 nM | | |
| 76 | [structure: H$_2$N-CO-(R,R)-epoxide-COOEt] | >1 μM | | |

TABLE 2-continued

Epoxysuccinate structures and inhibition data.

| No | Structure | Cal I IC$_{50}$ | Relative selectivity for Cal I E64 = 1.0[f] | LD$_{50}$ ≥ 50 μM primary neurons |
|---|---|---|---|---|
| 77 | 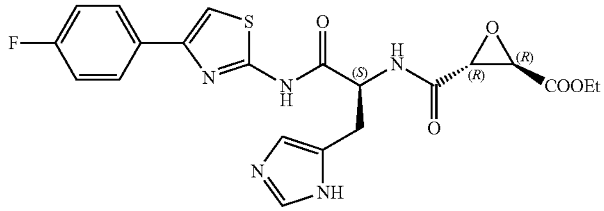 | >1 μM | | |
| 30b | 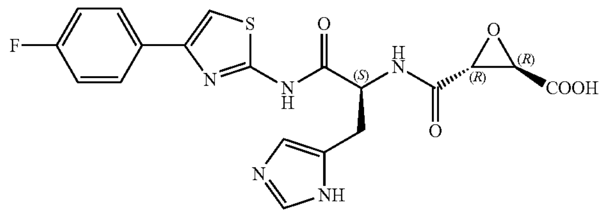 | >1 μM | | |
| 78 | 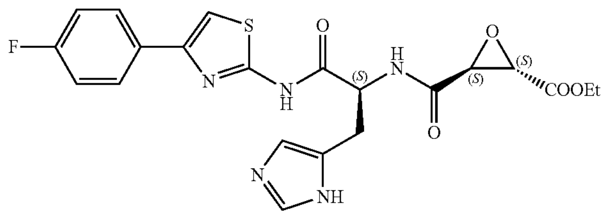 | >1 μM | | |
| 30a | 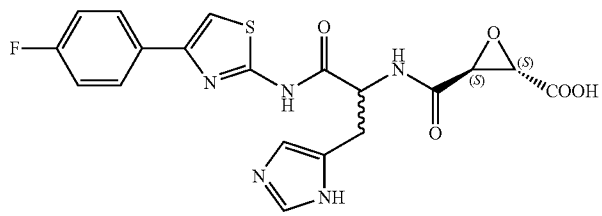 | 100 nM | | |
| 79 | 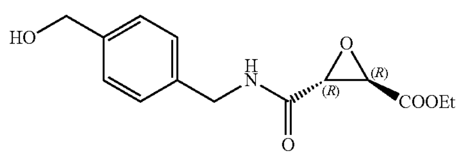 | >1 μM | | |
| 80 | 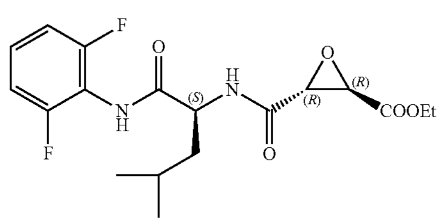 | >1 μM | | |
| 23b | 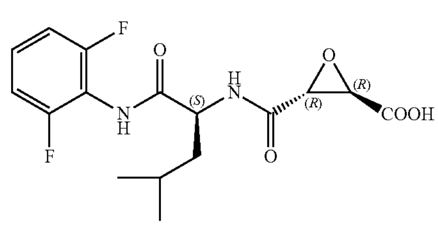 | >1 μM | | |

TABLE 2-continued
Epoxysuccinate structures and inhibition data.
| No | Structure | Cal I IC$_{50}$ | Relative selectivity for Cal I E64 = 1.0[f] | LD$_{50}$ ≥ 50 μM primary neurons |
|---|---|---|---|---|
| 81 | 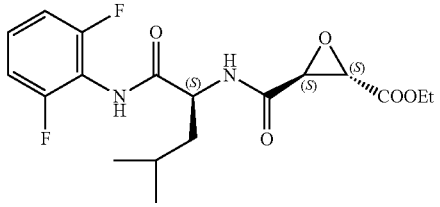 | >1 μM | | |
| 23a | 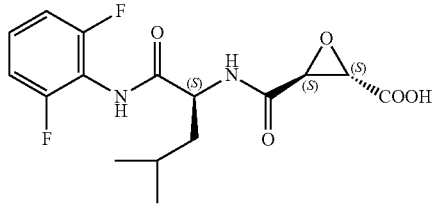 | 50 nM | | |
| 82 | 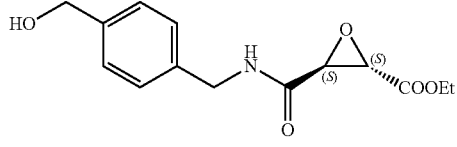 | >1 μM | | |
| 83 | 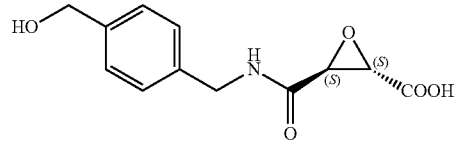 | >1 μM | | |
| 84 | 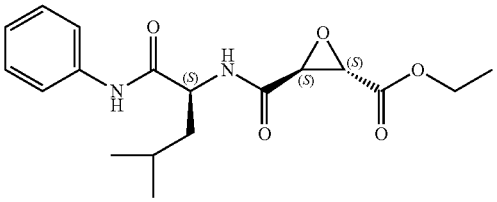 | 2.5 μM | | |
| 22 | 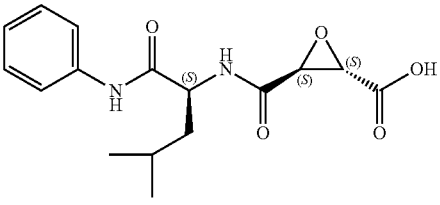 | 100 nM | | |
| 85 | 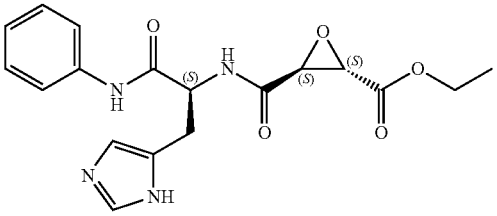 | >10 μM | | |

TABLE 2-continued
Epoxysuccinate structures and inhibition data.
| No | Structure | Cal I IC$_{50}$ | Relative selectivity for Cal I E64 = 1.0[f] | LD$_{50}$ ≥ 50 μM primary neurons |
|---|---|---|---|---|
| 28 | 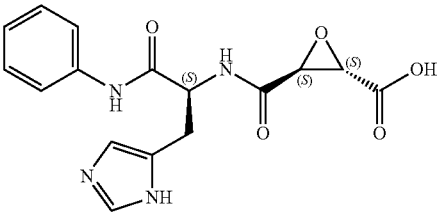 | 5 μM | | |
| 35 | 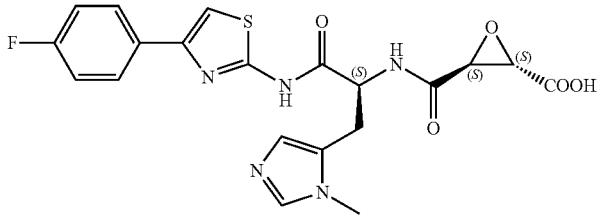 | 5 μM | | |
| 36 | 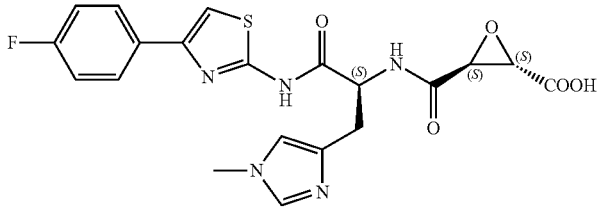 | 225 nM | | |
| 29 | 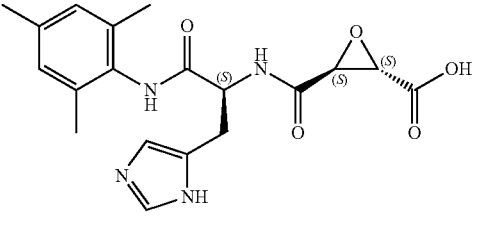 | 5 μM | | |
| 32 | 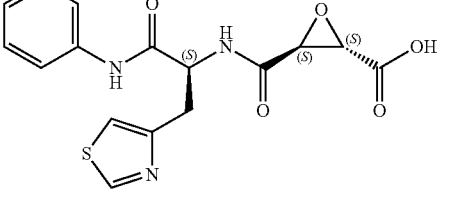 | 2.5 μM | | |
| 33 | 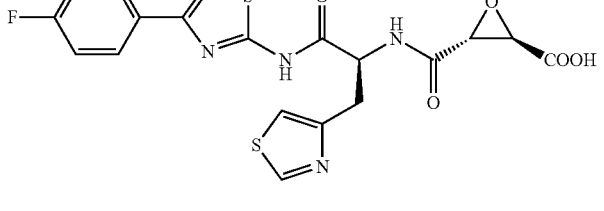 | 100 nM | | |

TABLE 2-continued

Epoxysuccinate structures and inhibition data.

| No | Structure | Cal I IC$_{50}$ | Relative selectivity for Cal I E64 = 1.0[f] | LD$_{50}$ ≥ 50 μM primary neurons |
|---|---|---|---|---|
| 31a | 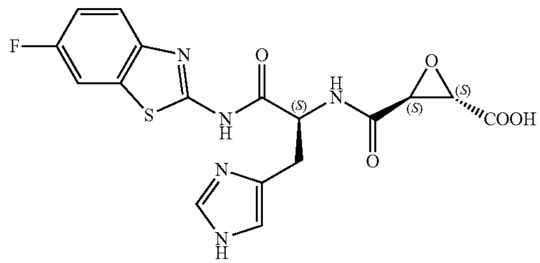 | 535 nM | | |
| 31b | 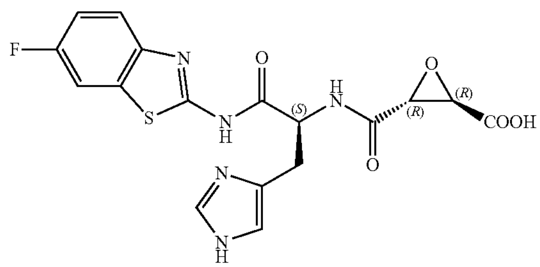 | >1 uM | | |
| 86 | 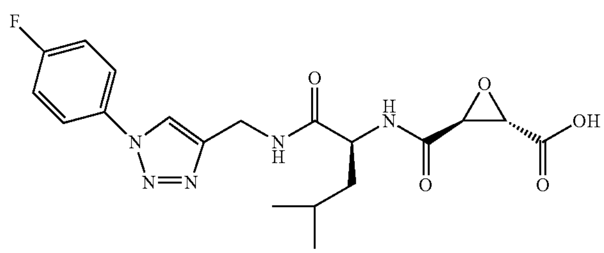 [SMILES: CC(C)C[C@H](NC(=O)[C@H]1O[C@@H]1C(=O)O)C(=O)NCc1cn(-c2ccc(F)cc2)nn1] | 30 nM | | |
| 87 | 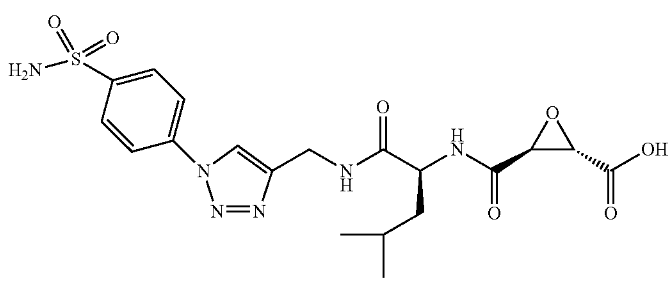 [SMILES: CC(C)C[C@H](NC(=O)[C@H]1O[C@@H]1C(=O)O)C(=O)NCc1cn(-c2ccc(S(N)(=O)=O)cc2)nn1] | 50 nM | | |
| 88 | 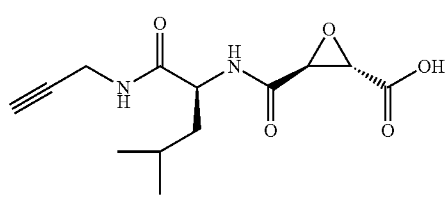 [SMILES: C#CCNC(=O)[C@H](CC(C)C)NC(=O)[C@H]1O[C@@H]1C(=O)O] | 275 nM | | |
| 50 | 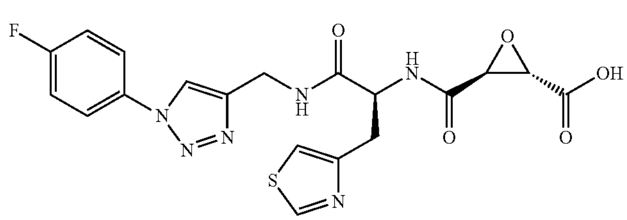 [SMILES: O=C(NCc1cn(-c2ccc(F)cc2)nn1)[C@H](Cc1cscn1)NC(=O)[C@H]1O[C@@H]1C(=O)O] | 125 nM | | |

TABLE 2-continued

Epoxysuccinate structures and inhibition data.

| No | Structure | Cal I IC$_{50}$ | Relative selectivity for Cal I E64 = 1.0[f] | LD$_{50}$ ≥ 50 μM primary neurons |
|---|---|---|---|---|
| 49 | 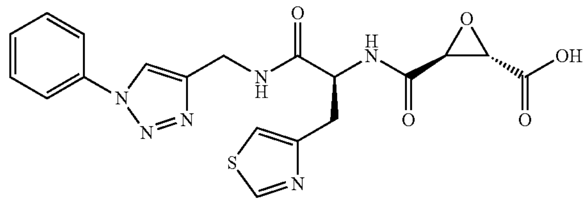 [SMILES: O=C(NCc1cn(-c2ccccc2)nn1)[C@H](Cc1cscn1)NC(=O)[C@H]1O[C@@H]1C(=O)O] | 1 uM | | |
| 51 | 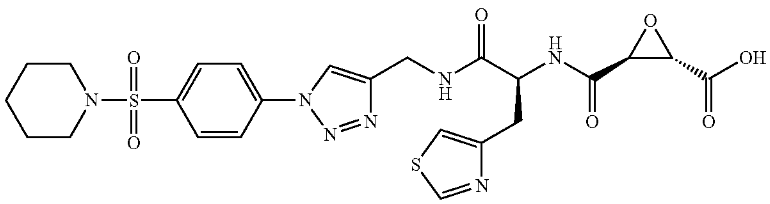 [SMILES: O=C(NCc1cn(-c2ccc(S(=O)(=O)N3CCCCC3)cc2)nn1)[C@H](Cc1cscn1)NC(=O)[C@H]1O[C@@H]1C(=O)O] | 1.5 uM | | |
| 52 | 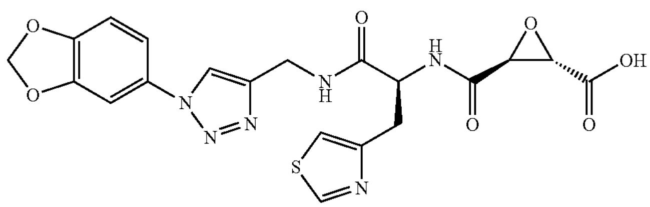 [SMILES: O=C(NCc1cn(-c2ccc3c(c2)OCO3)nn1)[C@H](Cc1cscn1)NC(=O)[C@H]1O[C@@H]1C(=O)O] | 400 nM | | |
| 53 | 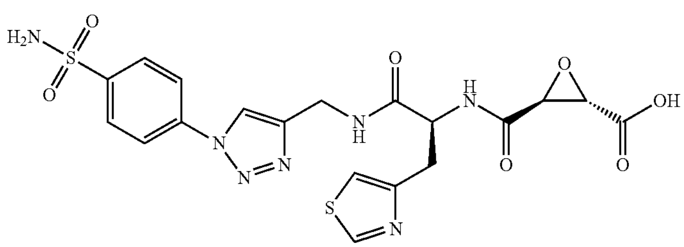 [SMILES: NS(=O)(=O)c1ccc(-n2cc(CNC(=O)[C@H](Cc3cscn3)NC(=O)[C@H]3O[C@@H]3C(=O)O)nn2)cc1] | >1 μM | | |
| 54 | 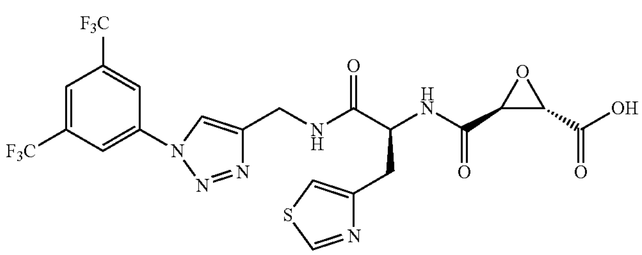 [SMILES: O=C(NCc1cn(-c2cc(C(F)(F)F)cc(C(F)(F)F)c2)nn1)[C@H](Cc1cscn1)NC(=O)[C@H]1O[C@@H]1C(=O)O] | >1 μM | | |
| 55 | 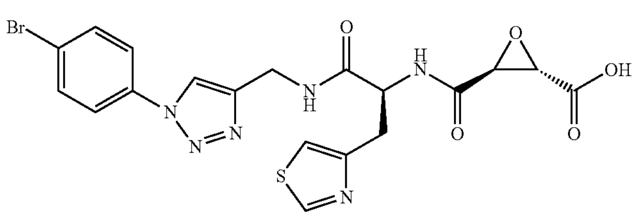 [SMILES: O=C(NCc1cn(-c2ccc(Br)cc2)nn1)[C@H](Cc1cscn1)NC(=O)[C@H]1O[C@@H]1C(=O)O] | 40 nM | | |

TABLE 2-continued

Epoxysuccinate structures and inhibition data.

| No | Structure | Cal I IC$_{50}$ | Relative selectivity for Cal I E64 = 1.0$^r$ | LD$_{50}$ ≥ 50 μM primary neurons |
|---|---|---|---|---|
| 56 | 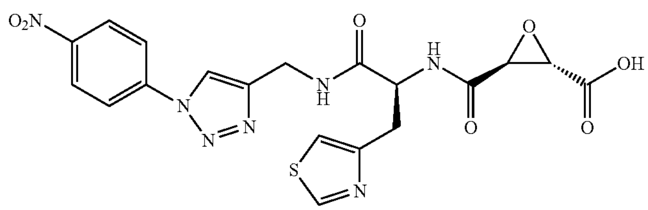 [SMILES: O=C(NCc1cn(-c2ccc([N+](=O)[O-])cc2)nn1)[C@H](Cc1cscn1)NC(=O)[C@H]1O[C@@H]1C(=O)O] | 300 nM | | |
| 57 | 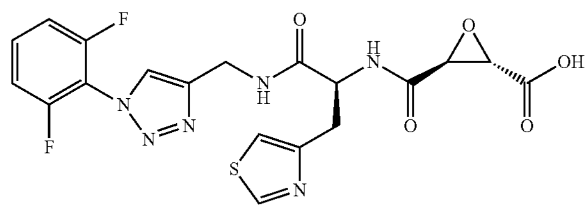 [SMILES: O=C(NCc1cn(-c2c(F)cccc2F)nn1)[C@H](Cc1cscn1)NC(=O)[C@H]1O[C@@H]1C(=O)O] | >1 μM | | |
| 58 | 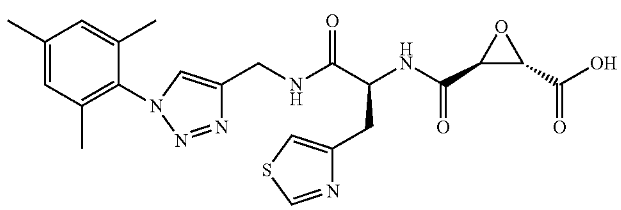 [SMILES: Cc1cc(C)c(-n2cc(CNC(=O)[C@H](Cc3cscn3)NC(=O)[C@H]3O[C@@H]3C(=O)O)nn2)c(C)c1] | >1 μM | | |
| 39 | 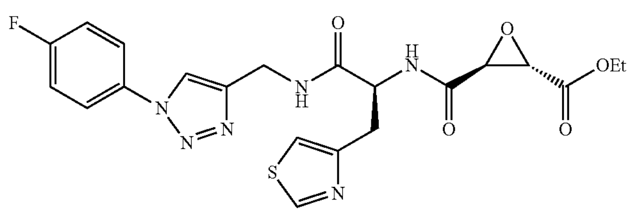 [SMILES: CCOC(=O)[C@H]1O[C@@H]1C(=O)N[C@@H](Cc1cscn1)C(=O)NCc1cn(-c2ccc(F)cc2)nn1] | | | |
| 89 | 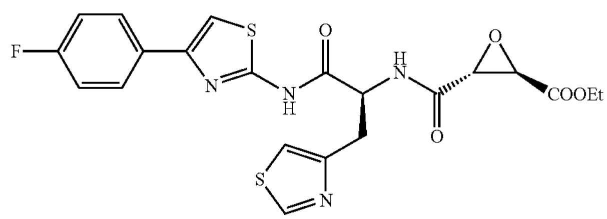 [SMILES: CCOC(=O)[C@@H]1O[C@H]1C(=O)N[C@@H](Cc1cscn1)C(=O)Nc1nc(-c2ccc(F)cc2)cs1] | | | |

TABLE 3

Epoxysuccinate structures and inhibition data for full length Cal 1.

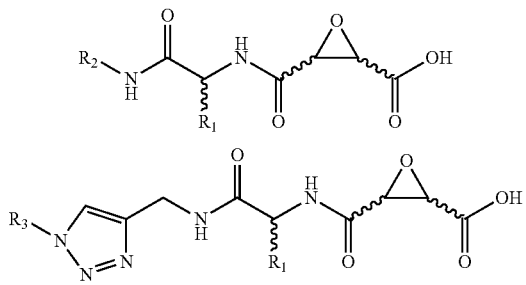

| | $R_1$ | $R_2$ or $R_3$ | epoxide stereochem | Cal 1 $IC_{50}{}^a$ |
|---|---|---|---|---|
| E64 | L-Leucine | $R_2$ = Guanidinyl-1-butyl | S,S | 100 nM |
| 22 | L-Leucine | $R_2$ = Phenyl | S,S | 100 nM |
| 23a | L-Leucine | $R_2$ = 2,6-Difluorophenyl | S,S | 100 nM |
| 23b | L-Leucine | $R_2$ = 2,6-Difluorophenyl | R,R | >1 μM |
| 24a | L-Leucine | $R_2$ = 4-(4-Fluorophenyl)thiazol-2-amine | S,S | 50 nM |
| 24b | L-Leucine | $R_2$ = 4-(4-Fluorophenyl)thiazol-2-amine | R,R | 250 nM |
| 25 | L-Leucine | $R_2$ = 4-F-Phenyl-$SO_2$—NH—$(CH_2)_4$—$NH_2$ | S,S | 150 nM |
| 26 | L-Leucine | $R_2$ = Lipoyl-NH—$(CH_2)_4$—$NH_2$ | S,S | 100 nM |
| 27 | L-Leucine | $R_2$ = D-Biotin-NH—$(CH_2)_4$—$NH_2$ | S,S | 100 nM |
| 28 | L-Histidine | $R_2$ = Phenyl | S,S | 5 μM |
| 29 | L-Histidine | $R_2$ = 1,3,5-Trimethylaniline | S,S | 5 μM |
| 30a | L/D-Histidine | $R_2$ = 4-(4-Fluorophenyl)thiazol-2-amine | S,S | 100 nM |
| 30b | L/D-Histidine | $R_2$ = 4-(4-Fluorophenyl)thiazol-2-amine | R,R | >1 μM$^b$ |
| 31a | L/D-Histidine | $R_2$ = 6-Fluorobenzo[d]thiazol-2-amine | S,S | 530 nM |
| 31b | L/D-Histidine | $R_2$ = 6-Fluorobenzo[d]thiazol-2-amine | R,R | >1 μM$^b$ |
| 32 | L-Ala(4-thiazolyl) | $R_2$ = Phenyl | S,S | 2.5 μM |
| 33 | L-Ala(4-thiazolyl) | $R_2$ = 4-(4-Fluorophenyl)thiazol-2-amine | S,S | 100 nM |
| 34 | L-Ala(4-thiazolyl) | $R_2$ = 4-(4-Ethynylphenyl)thiazol-2-amine | S,S | 100 nM |
| 35 | L-His(2-Me) | $R_2$ = 4-(4-Fluorophenyl)thiazol-2-amine | S,S | 5 μM |
| 36 | L-His(4-Me) | $R_2$ = 4-(4-Fluorophenyl)thiazol-2-amine | S,S | 225 nM |
| 50 | L-Ala(4-thiazolyl) | $R_3$ = 4-Fluorophenyl | S,S | 100 nM |
| 49 | L-Ala(4-thiazolyl) | $R_3$ = Phenyl | S,S | 1 μM |
| 51 | L-Ala(4-thiazolyl) | $R_3$ = 4-(Piperidin-1-ylsulfonyl)phenyl | S,S | 1.5 μM |
| 52 | L-Ala(4-thiazolyl) | $R_3$ = Benzo[d][1,3]dioxol-5-yl | S,S | 400 nM |
| 53 | L-Ala(4-thiazolyl) | $R_3$ = 4-Sulfamoylphenyl | S,S | >1 μM$^b$ |
| 54 | L-Ala(4-thiazolyl) | $R_3$ = 3,5-Bis(trifluoromethyl)phenyl | S,S | >1 μM$^b$ |
| 55 | L-Ala(4-thiazolyl) | $R_3$ = 4-Bromophenyl | S,S | 40 nM |
| 56 | L-Ala(4-thiazolyl) | $R_3$ = 4-Nitrophenyl | S,S | 300 nM |
| 57 | L-Ala(4-thiazolyl) | $R_3$ = 2,6-Bis(fluoro)phenyl | S,S | >1 μM$^b$ |
| 58 | L-Ala(4-thiazolyl) | $R_3$ = 2,4,6-Tris(methyl)phenyl | S,S | >1 μM$^b$ |

$^a$Inhibition was measured by monitoring fluorescence emission at 480 nm after 20 min incubations with varying concentration of inhibitor in the presence of the FRET substrate: % inhibition normalized to control incubations in the absence of inhibitor. Data represents the mean ± S.D. of triplicate experiments.
$^b$Inhibition not quantifiable at 1 μM.

$1^{st}$ generation inhibitors incorporating a L-leucine residue at the P2 position, 22-27 (Table 3), were designed to mimic E-64 at the P2 position while varying the P3 cap group to increase potency and bioavailability compared to the guanidino group of E-64. The majority of $1^{st}$ generation inhibitors were found to be approximately equipotent to E-64, with $IC_{50}$ values ~100 nM (±20-50), and one inhibitor, 24a, displayed improved potency with an $IC_{50}$ value of 50 nM (±25). These results are consistent with the understanding that hydrophobic amino acid residues at the P2 position deliver high affinity for Cal1. In two instances, 23 and 24, the importance of the S,S epoxide stereochemistry was demonstrated. Cal1 inhibition was not observed for the R,R derivative, 23b, whereas the S,S isomer was a potent inhibitor. The S,S epoxide stereochemistry has been proposed to be optimal based on molecular modeling, suggesting that the formation of a conserved interaction network by S,S epoxides enables close contact between the active site cysteine and the electrophilic $C_2$ of the epoxide ring (Mladenovic, M. et al., The Journal of Physical Chemistry B 2008, 112, 11798-11808; Otto, H. H. et al., Chem Rev 1997, 97, 133-172; each herein incorporated by reference in its entirety).

Example 4: Active Site Modification by Novel Calpain Inhibitors

The recombinant Cal1 catalytic domain ($Cal1_{cat}$) is composed of the proteolytic domain of the full-length enzyme and has been used as a surrogate to study calpain activity (Moldoveanu, T. et al., Cell 2002, 108, 649-660; Moldoveanu, T. et al., Journal of Molecular Biology 2004, 343, 1313-1326; Cuerrier, D. et al., Biochemistry 2006, 45, 7446-52; Cuerrier, D. et al., Journal of Biological Chemistry 2005, 280, 40632-40641; each herein incorporated by reference in its entirety). $Cal1_{cat}$ provides an advantage, because upon $Ca^{2+}$-induced activation, full length Cal1 engages in autocatalytic, self-proteolysis complicating analysis of activity and inhibition. $Cal1_{cat}$ is devoid of the autocatalytic activity observed for full length Cal1. Recombinant rat Cal1$_{cat}$ was expressed and purified from *E. coli*, to examine aspects of inhibition in more detail.

Figure 3A:
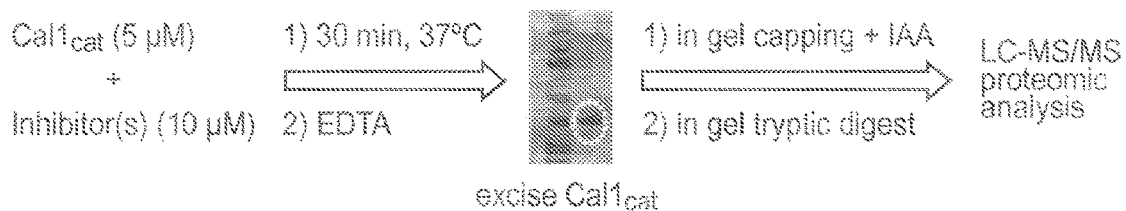
FIG. 3A-3D shows confirmation of covalent modification of Cal1 active site Cys by epoxysuccinate inhibitors.
Figure 3B:
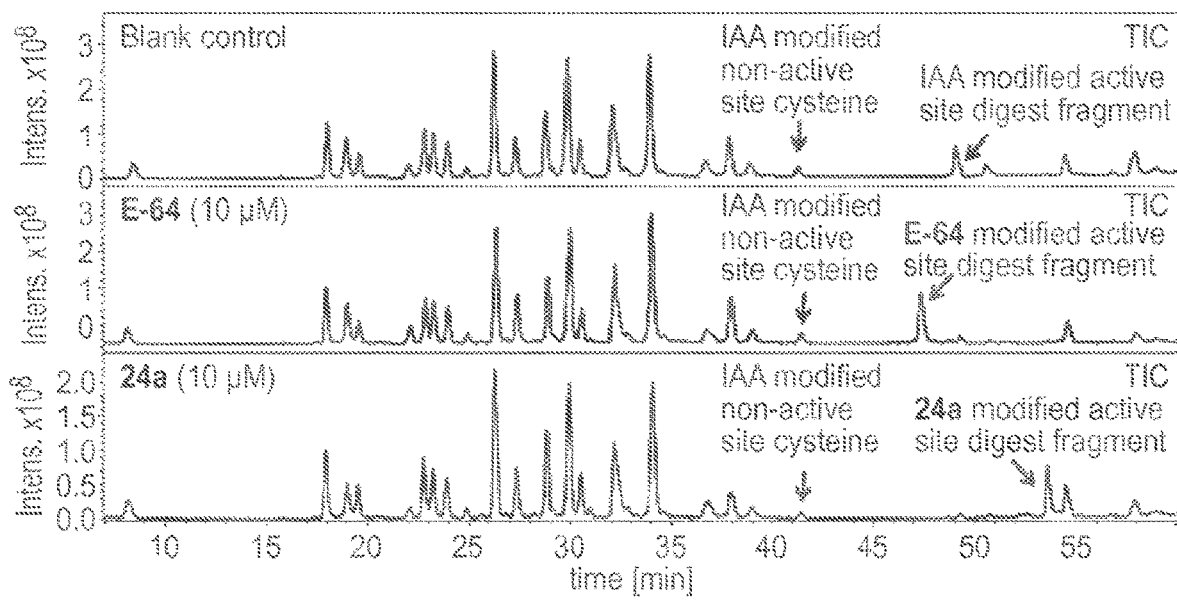

Inhibition kinetics and x-ray crystallography support a mechanism of calpain inhibition by E-64, resulting from covalent modification of the active site Cys (Suzuki, K. et al., *FEBS Letters* 1983, 152, 67-70; herein incorporated by reference in its entirety). LC-MS/MS was used to support a similar mechanism for 24a. The experimental methodology is outlined in FIG. 3A. Cal1$_{cat}$ (5 µM) was incubated with the appropriate inhibitor (10 µM) for 30 min. The mixture was quenched with EDTA (10 µM), and run on a SDS PAGE gel. Band excision, in-gel capping of free cysteines with iodoacetamide (IAA, 10 µM), tryptic digest, and subsequent LC-MS/MS analysis afforded the chromatograms shown in FIG. 3B. The peptide fragment containing the active site Cys (TDICQGALGDC*WLLAAIASLTNETILHR) (SEQ ID NO: 7) was identified by mapping of tryptic digests and matching of m/z values for IAA modification (in the absence of inhibitors), and covalent modification by 24a or E-64. A peptide fragment containing an IAA labeled non-active site cysteine was used as an internal standard for semi-quantitative EIC analysis of the degree of active site modification observed (FIG. 3B). It is noteworthy that although Cal1$_{cat}$ was employed in these studies, analysis of full length Cal1 gave an identical active site peptide fragment (TIC of control digest from Cal1$_{cat}$ and full length Cal1 are compared in Example 10).

Figure 3C:
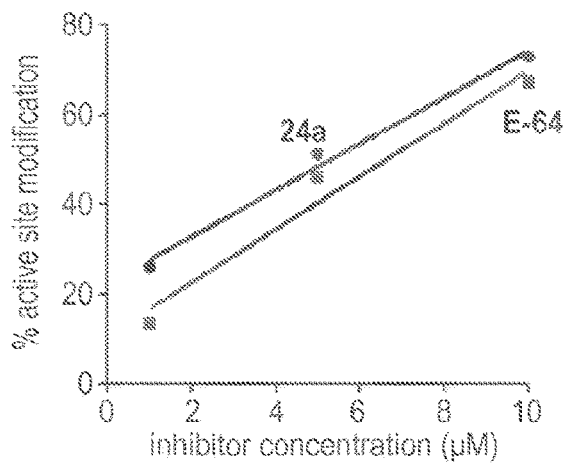
Figure 3D:
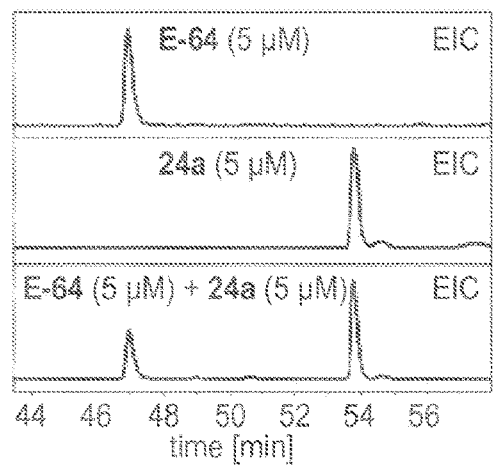

Similar incubations of Cal1$_{cat}$ (1 µM) with either E-64 or 24a showed a concentration dependent modification of the active site cysteine (FIG. 3C). Co-incubation of Cal1$_{cat}$ with E-64 and 24a (both 1 µM) demonstrated greater modification by 24a on the basis of observed EIC peak areas (FIG. 3D). This outcome, combined with the potency of inhibition by 24a, supported retention of the 4-F-phenylthiazole P3/P4 cap group for subsequent ligand development.

Example 5: Development of Second Generation Calpain Inhibitors

CA clan cysteine proteases have similar "unprimed" substrate binding pockets, with a common preference for hydrophobic residues at the S2 binding site (i.e. Leu, Ile, Val, Phe) (Greenbaum, D. et al., *Chem Biol* 2000, 7, 569-81; Greenbaum, D. C. et al., *Chemistry & Biology* 2002, 9, 1085-1094; Otto, H. H. et al., *Chem Rev* 1997, 97, 133-172; each herein incorporated by reference in its entirety). Previous work on peptides appended with an epoxysuccinate ester warhead has indicated that a P2 histidine might confer Cal1 selectivity. The rationale given being the presence of a stabilizing hydrogen bond occurring within the S2 pocket with a highly conserved water molecule chelated by Glu-349 and Thr-210 (Cuerrier, D. et al., *J Biol Chem* 2007, 282, 9600-11; herein incorporated by reference in its entirety). A focused series of L-histidine incorporating analogs was synthesized and evaluated (28-31). In addition, two N-methyl L-histidine derivatives, 35 and 36, were created to probe the S2 pocket.

Facile protonation of the histidine can cause problems in synthesis and hinder druggability, therefore, thiazole analogues were also developed (32-34). Screening of the 2$^{nd}$ generation compounds revealed a general loss of activity on replacement of L-leucine (Table 3), although the P2 analogues, 30a and 33, were approximately equipotent to E-64 (IC$_{50}$~100 nM). The crystal structures used to rationalize the selectivity and active site interactions of L-histidine at P2 contained ethyl epoxysuccinate esters, yet simple ethyl esters of 1$^{st}$ and 2$^{nd}$ generation epoxysuccinates did not give measurable inhibition of Cal1.

Figure 4:
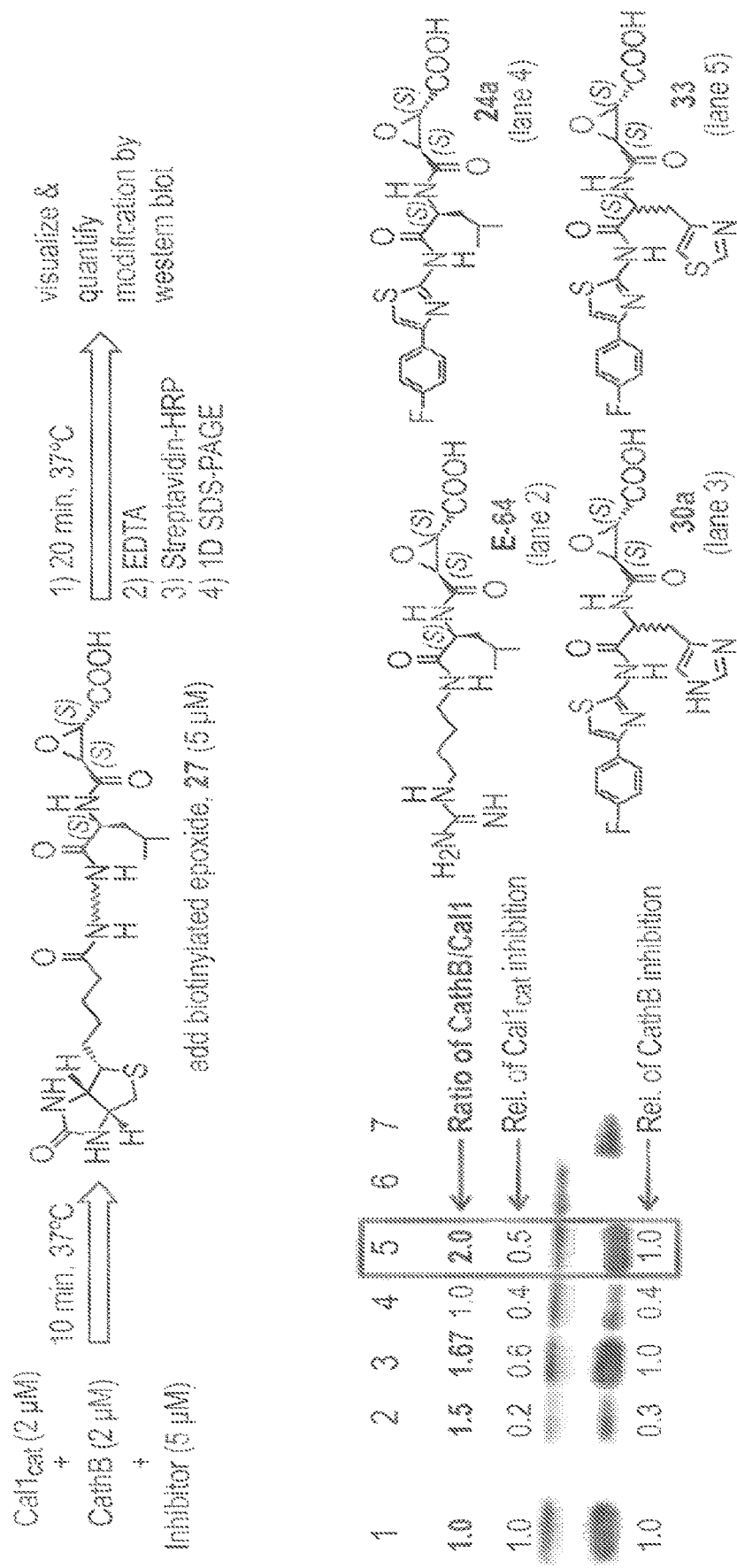
FIG. 4 shows competitive inhibition of Cal1$_{cat}$ vs CathB measured by competitive blocking of active site modification by the biotinylated probe 27. Anti-biotin western blotting of Cal1$_{cat}$ (Lane 6) or CathB (Lane 7) after incubation with 27 show the expected immunoreactivity of the covalently modified proteins. Incubation of a mixture of Cal1$_{cat}$+ CathB with 27 shows modification of both proteins (Lane 1). Preincubation with inhibitors (Lanes 2-5) shows the ability of each inhibitor to block the active site from modification by 27. Densitometric analysis, using means from triplicate immunoblots, was used to estimate the modification of each protein by 27 in the presence of inhibitors relative to control (Lane 1: ratio=1.0). The ratio of the CathB/Cal1$_{cat}$ immunoreactivity is an estimate of selectivity towards Cal1, with 30a (Lane 3) and 33 (Lane 5) showing highest selectivity.

To examine the ability of the P2 histidine substitution and the thiazolyl analogues to confer selectivity, a simple competition experiment was performed, comparing E-64, 24a, 30a, and 33. The biotinylated leucine-based epoxysuccinate 27 was shown to be a Cal1 inhibitor, and was also shown to covalently modify both Cal1 and CathB, individually and in combination, using anti-biotin immunoblotting of reaction mixtures after 1D SDS-PAGE (FIG. 4). CathB is a related CA clan cysteine protease which shows similar unprimed subsite binding preference to Cal1. Cal1$_{cat}$ was used in place of the full length enzyme to avoid autocatalysis. Cal1$_{cat}$ has been reported to possess decreased activity compared to the full length enzyme, but to retain similar substrate specificity (Moldoveanu, T. et al., *Cell* 2002, 108, 649-660; Moldoveanu, T. et al., *Journal of Molecular Biology* 2004, 343, 1313-1326; Cuerrier, D. et al., *Biochemistry* 2006, 45, 7446-52; Cuerrier, D. et al., *Journal of Biological Chemistry* 2005, 280, 40632-40641; each herein incorporated by reference in its entirety).

Cal1$_{cat}$ and CathB were pre-treated with inhibitors for 10 min, followed by a 20 min incubation with the biotinylated epoxide, 27, as illustrated in FIG. 4. E-64 caused substantial loss of signal (lane 2), indicating effective blocking of the active sites of both enzymes from modification by 27. The potent 1$^{st}$ generation Cal1 inhibitor 24a also substantially reduced signals from both enzymes (lane 4), whereas simple visual inspection of western blots showed that 30a (lane 3) and 33 (lane 5) elicited little change in the CathB signal. Qualitatively, the desired selectivity of imidazolyl and thiazolyl substitutions at the P2 position was demonstrated. A more quantitative estimate of selectivity was achieved by comparison of band intensities. Setting the ratio of Cal1$_{cat}$ versus CathB band intensities from modification by the probe, 27, as 1.0, E-64 was assessed to have selectivity for Cal1$_{cat}$ (1.5), whereas 24a was observed to be non-selective (FIG. 4). Both 2$^{nd}$ generation inhibitors were observed to be selective for Cal1$_{cat}$.

Figure 5B:
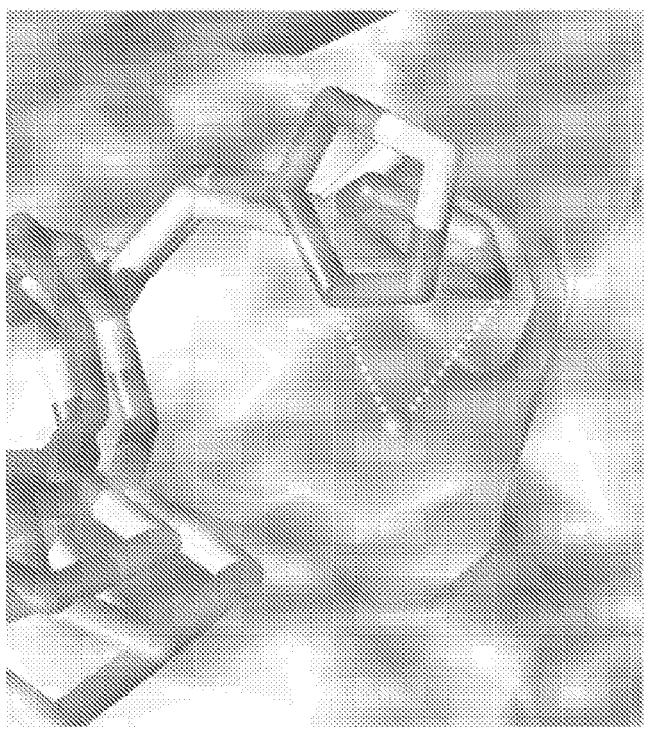
FIG. 5A-5B shows selected inhibitors (compounds 24a, 30a, and 33) docked within the x-ray structure of Cal1$_{cat}$ [PDB: 2NQG].
Figure 5A:

Structural overlay of docking results for 24a, 30a, and 33 predicts a common binding motif, with the P3 cap group extended into the solvent exposed S4-S3 region and the P2 peptidomimetic moiety situated within the S2 pocket (FIG. 5). Docking poses are compatible with the potential of 30a and 33 to interact with the conserved H$_2$O molecule at the S2 site. It should be noted that incorporation of imidazolyl or thiazolyl groups did not increase affinity for the Cal1 binding site relative to the leucine-based inhibitors, however, this modification did provide selectivity.

Example 6: In Silico Guidance Towards P3/P4 Refinement

Figure 6:
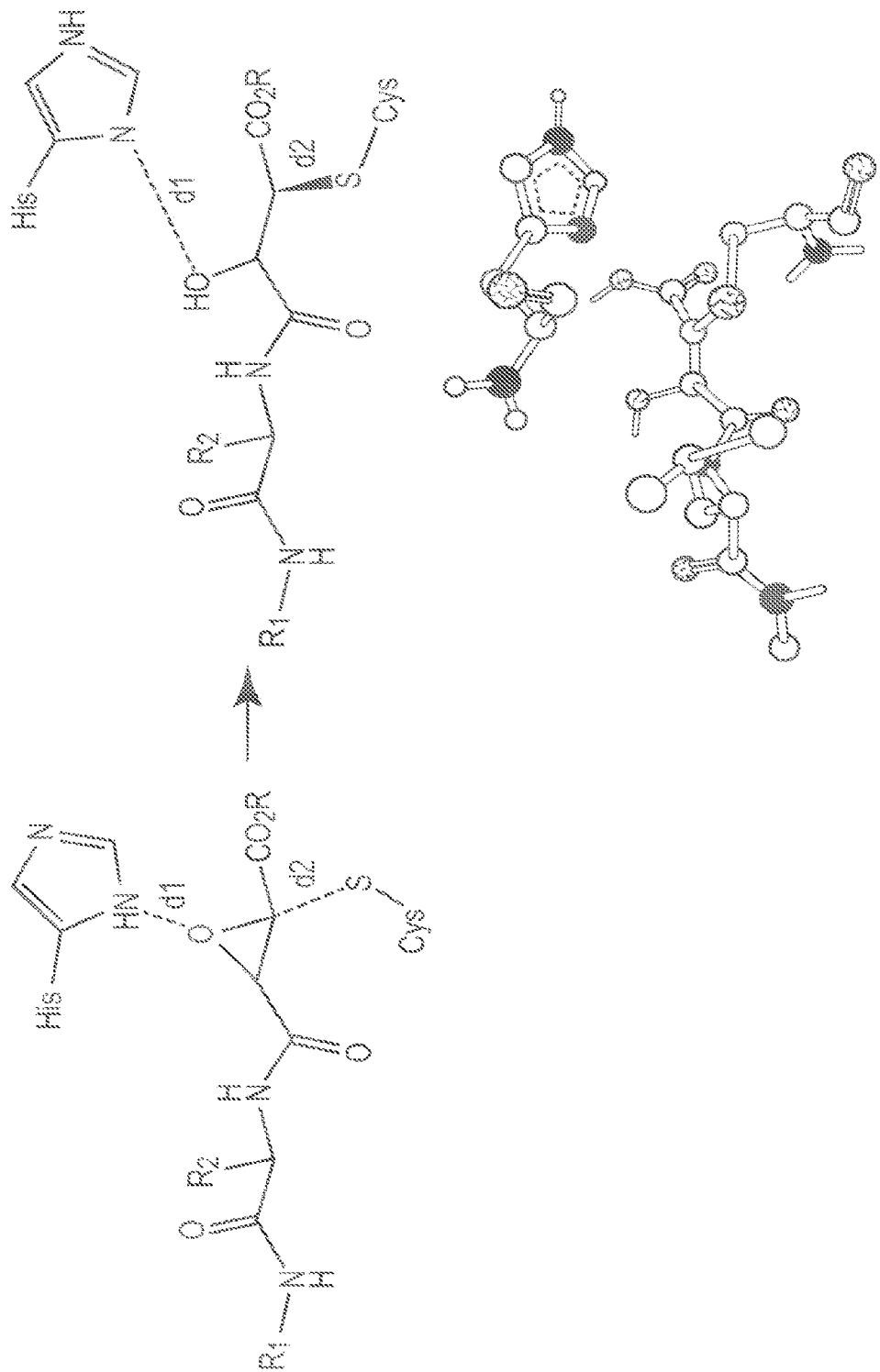
FIG. 6 shows crystal structures of epoxide inhibitors bound at the active site of Cal1 show a relaxed, ring-opened structure, whereas the transition state for epoxide ring-opening requires the Cys nucleophile and His general acid to be aligned for $S_N2$ substitution. Triazole-based inhibitors were designed based upon docking scores biased towards distances approaching 2 Å. For comparison, in the crystal structures: 2NQG d1=4.606 and d2=1.810; and 1TLO (shown with E64, His, and Cys nucleophile) d1=4.775, d2=1.833.

Computationally guided drug design based upon crystal structures of cysteine proteases modified by epoxide inhibitors is recognized as problematic. Nucleophilic attack by the active site Cys leads to ring-opening and relaxation by free rotation about the C(OH)—C(S-Cys) single bond (FIG. 6). Such crystal structures are not expected to reflect the significant stereoelectronic requirement for stabilization of the cyclic transition state. Therefore, as an alternative approach, docking of inhibitors was scored (NSig) by emphasizing two parameters: d1) the distance between the His general base and the epoxide 0; and d2) the distance between the nucleophilic S and C$_2$ of the epoxide. To test this approach and to explore P3/P4 modifications further, a click chemistry approach was used to generate a library of analogs of compound 33, using a divergent synthetic approach. Thirty two synthetically accessible analogs of compound 33 were screened in silico to select ten for synthesis and assay. Compounds predicted to be poor inhibitors (53, 54, 57, and 58) yielded relatively high $IC_{50}$ values, while molecules predicted to be effective inhibitors displayed potent activity for calpain (50, 52, 55, and 56), with 54 representing a notable outlier by demonstrating weak activity despite being predicted to be potent. A correlation of docking score (Nsig) with $IC_{50}$ gave a good correlation ($R^2$=0.968) for 49-52, 55-56.

Example 7: Enzyme Kinetic Studies for Selectivity for Cal1

Figure 7A:
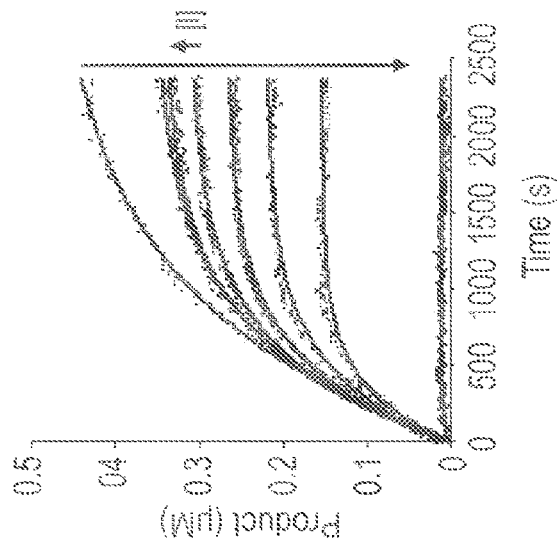
FIG. 7A-7C shows plots of secondary and primary kinetic data for inhibition of papain (FIG. 7A) and Cal1 (FIG. 7B) used to derive detailed kinetic parameters reported in Table 4: E-64 (diamonds—solid line); 24a (closed circles—dashed line); 33 (squares—solid line); 50 (open circles—dotted line). The observed rate constants ($k_{obs}$) shown in the double reciprocal plots were measured from non-linear fitting of "progress curves" curves for product formation from substrate. Exemplary progress curves are shown for Cal1 inhibition by E64 (FIG. 7C).
Figure 7B:
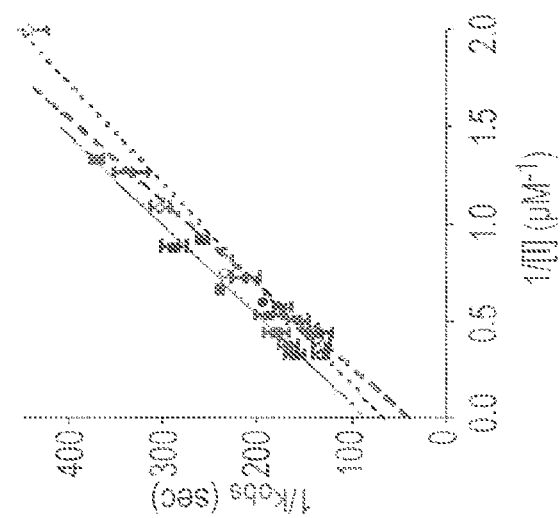
Figure 7C:
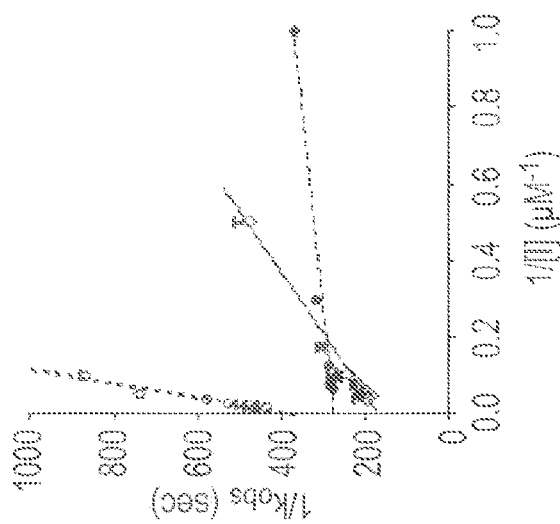

Papain is representative of a family of typically lysosomal or secreted cysteine proteases, including the human cathepsins (B, C, F, H, K, L1-2, O, S, W, Z). The P1 peptide residue is cationic and P2 is hydrophobic and includes Leu, therefore papain represents a useful counterscreen for Cal1. Several methods have been reported in the literature for detailed kinetic analysis of the irreversible inhibition of cysteine proteases, including Cal1. S/N was too poor for kinetic analysis using the FRET method employed in initial screening, therefore conditions were optimized for use of the aminomethylcoumarin substrate, SLLVYAMC (SEQ ID NO: 8). Using this substrate, kinetic parameters were derived using the method of Davies and co-workers, whereby "progress curves" were initially obtained measuring product formation as a function of time and fitted to $y=P_{\infty}*(1-e^{(-k*x)})$ (FIG. 7) (Cuerrier, D. et al., *J Biol Chem* 2007, 282, 9600-11; herein incorporated by reference in its entirety). Plots of $P_{\infty}$ versus 1/[I] gave excellent linear correlations supporting the validity of the approach. Kinetic parameters ($k_i$, $K_I$, $k_i/K_I$) were obtained from double reciprocal plots (FIG. 7). Using $k_i/K_I$ as a measure of inhibition efficiency to assess relative selectivity for inhibition of Cal1 over papain, the data presented in Table 4 show that 24a is less selective for Cal1 than is the lead compound E-64, whereas 33, 34, 50 all show Cal1 selectivity. Reference to Table 4 and FIG. 7 show that the cause of this selectivity is not differentiated inhibition of Cal1, but inefficient inhibition of papain caused by the P2-thiazole. The P3 cap group of 50 also contributes to the higher selectivity of this derivative by reducing binding affinity to papain, but not Cal1.

substrate, 10 nM of native Cal1, and 20 µM TCEP (reducing agent) were added to the reaction mixture containing assay buffer (Tris [10 mM], NaCl [100 mM], pH 7.4). Cal1 was activated by the addition of 10 µM calcium. Cleavage of the scissile bond amide bond, K-S, releases the fluorophore (EDANS) from the internal quenching molecule (DABCYL), resulting in an increase in fluorescence measured at 320 nm excitation and 480 nm emission wave lengths for 30 min. Each inhibitor was added to the reaction mixture at varying concentrations (10 nM, 100 nM, 1 µM, and 10 µM) to detect inhibition of Cal1 and reduction in fluorescence was measured by 96 well-plate reader. Approximate $IC_{50}$ values of each compound were generated using linear regression within Graphpad Prism Software.

Example 9: Cal1cat Expression and Purification

Expression: *E. coli* strain BL21(DE3) was transformed with a pET24d-based plasmid construct containing active domains I-II of t-calpain, the creation of which is described in Davies, P. L., et al., *Cell*, 2002. 108(5): 649-660, herein incorporated by reference in its entirety. One liter cultures were incubated in LB medium containing 30 µg/mL kanamycin at 37° C. with shaking at 225 rpm, and induced with 0.5 mM IPTG after reaching an OD600 of 0.6. Following an additional three hours of incubation, cell pellets were generated by centrifugation of 0.5 L aliquots (4° C., 13,000 rpm, 30 min) and stored at −80° C. prior to use.

Growth conditions for Cal1cat expression: *E. coli* strain BL21(DE3) was transformed with a pET24d-based plasmid construct containing active domains I-II of ti-calpain, the creation of which is described in Davies, P. L., et al., *Cell*, 2002. 108(5): 649-660, herein incorporated by reference in its entirety. One liter cultures were incubated in LB medium containing 30 µg/mL kanamycin at 37° C. with shaking at 225 rpm, and induced with 0.5 mM IPTG after reaching an OD600 of 0.6. Following an additional three hours of incubation, cell pellets were generated by centrifugation of 0.5 L aliquots (4° C., 13,000 rpm, 30 min) and stored at −80° C. prior to use.

TABLE 4

Inhibition efficiency of epoxysuccinates for Cal1 and papain and relative selectivity.

| | Calpain1 | | | | Papain | | | | Relative Selectivity[c] |
|---|---|---|---|---|---|---|---|---|---|
| | $K_I$ (uM) | $k_i$ (s$^{-1}$) | $10^{-4} \times k_i/K_i$[a] | rel[b] | $K_I$ (uM) | $k_i$ (s$^{-1}$) | $10^{-5} \times k_i/K_i$[a] | rel[b] | |
| E-64 | 4.0 | 0.12 | 3.02 ± 0.15 | 1 | 5.1 | 28.6 | 56.3 ± 5.2 | 1 | 1 |
| 24a | 6.0 | 0.16 | 2.74 ± 0.19 | 0.91 | 1.6 | 17.1 | 105 ± 4.1 | 1.9 | 0.5 |
| 33 | 2.6 | 0.08 | 2.96 ± 0.14 | 0.98 | 5.3 | 14.8 | 27.9 ± 4.7 | 0.50 | 2.0 |
| 34 | 3.5 | 0.14 | 3.89 ± 0.41 | 1.3 | 9.70 | 21.6 | 22.3 ± 0.24 | 0.40 | 3.3 |
| 50 | 2.9 | 0.10 | 3.31 ± 0.32 | 1.1 | 19.2 | 12.7 | 6.62 ± 0.74 | 0.12 | 9.3 |

[a]Calculated inhibition rate and apparent equilibrium constants versus full length Cal1 and papain.
[b]$k_i/K_i$ calculated relative to E-64.
[c]Selectivity calculated using $k_i/K_i$ relative to E-64 set at 1.0. Inhibition constants were calculated as described in the text, varying both enzyme and inhibitor concentrations.
Data represent the mean ± S.D. of triplicate experiments.

Example 8: Calpain Inhibition FRET Assay

The Calbiochem InnoZyme activity kit was used for measuring the inhibition effect inhibitors on human erythrocyte calpain 1 activity. A calpain FRET substrate, (DAB-CYL)-TPLKSPPPSPR-(EDANS) (SEQ ID NO: 9), was used to detect the activity of Cal1. 20 µM of the FRET Purification of Cal1$_{cat}$:

Frozen cell pellets were resuspended in 25 mL Lysis Buffer (500 mM NaCl, 50 mM HEPES, pH 7.6, 20 mM imidazole, 1 mM PMSF, 100 ug/mL lysozyme) and incubated on ice for 30 min. Cells were lysed by sonication and clarified by centrifugation (4° C., 13,000 rpm, 20 min). Lysate was applied to Ni$^{2+}$-affinity columns (HisTrap FF crude, 5 mL, GE Healthcare) for purification. Proteins were eluted with a linear gradient of 100:0 A:B to 0:100 A:B (Buffer A=500 mM NaCl, 50 mM HEPES, pH 7.6, 20 mM imidazole. Buffer B=500 mM NaCl, 250 mM imidazole, 50 mM HEPES, pH 7.6) at 5 mL/min and collected in 5 mL fractions containing 200 μL Receiving Buffer (50 mM HEPES, pH 7.6, 4 mM EDTA, 1 mM TCEP; final concentration). Eluted protein was concentrated by 10K molecular weight filter (Millipore), and exchanged into Storage Buffer (150 mM NaCl, 50 mM HEPES, pH 7.6, 5% glycerol (v/v), 1 mM TCEP, 100 μM EDTA) via gel filtration (HiTrap Desalting, 5 mL, GE Healthcare). Concentrated enzyme was stored in 20 μL aliquots at −80° C. Final purified enzyme protein concentration was determined by bicinchoninic acid assay (Thermo Scientific) following the manufacturer's protocol against BSA standards, diluted with Storage Buffer. Proteins were analyzed by 4-12% polyacrylamide gel (Nu-PAGE) loaded with 7 uL marker (Precision Plus Protein Kaleidoscope Standard, BioRad Inc), Gels were stained with Bio SafeCoomassie (BioRad, Inc).

```
μ I-II Sequence (SEQ ID NO: 10):
MGRHENAIKYLGQDYENLRARCLQNGVLFQDDAFPPVSHSLGFKELGPNS

SKTYGIKWKRPTELLSNPQFIVDGATRTDICQGALGDCWLLAAIASLTLN

ETILHRVVPYGQSFQEGYAGIFHFQLWQFGEWVDVVVDDLLPTKDGKLVF

VHSAQGNEFWSALLEKAYAKVNGSYEALSGGCTSEAFEDFTGGVTEWYDL

QKAPSDLYQIILKALERGSLLGCSINISDIRDLEAITFKNLVRGHAYSVT

DAKQVTYQGQRVNLIRMRNPWGEVEWKGPWSDNSYEWNKVDPYEREQLRV

KMEDGEFWMSFRDFIREFTKLEICNLTPDLEHHHHHH.
```

Figure 8:
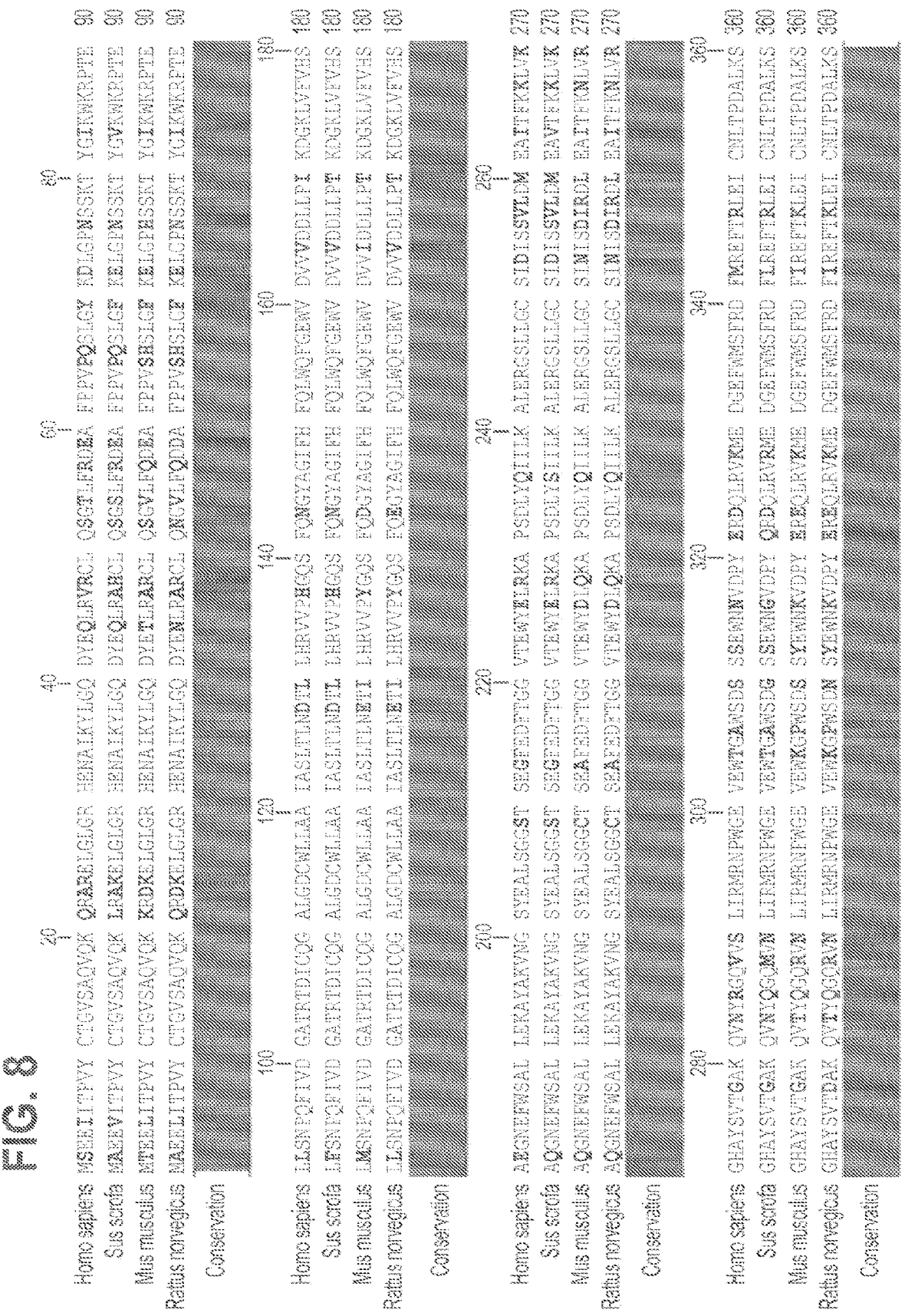
FIG. 8 shows the Cal1cat amino acid sequence alignments (*Homo sapiens* (top sequence; SEQ ID NO: 1); *Sus scrofa* (second sequence from top; SEQ ID NO: 2); *Mus musculus* (third sequence from top; SEQ ID NO: 3); and *Rattus norvegicus* (bottom sequence; SEQ ID NO: 4)). Active site cystein is 115 in the "mini calpains alignment" and 132 in "whole calpains alignment." Alignment was performed with CLC Sequence viewer (free version) using sequences downloaded from Pubmed.

Cal1$_{cat}$ sequence alignment is shown in FIG. 8. Active site cysteine is 115 in the "mini calpains alignment" and 132 in "whole calpains alignment". Alignment was performed with CLC Sequence viewer (free version) using sequences downloaded from Pubmed.

Example 10: LC-MS/MS Examination of Inhibitor Modified Cal1$_{cat}$ Active Site The recombinant Cal1$_{cat}$ (5 μM) was activated via addition of CaCl$_2$ (10 mM) and incubated with E-64 and/or 22a (5 μM) for 20 min. The reaction was quenched with EDTA (10 μM) and reaction mixture ran on a SDS PAGE gel. The Cal1$_{cat}$ containing band was cut from the gel and submitted to in-gel alkylation with IAA (100 mM) for 60 min, followed by trypsin digestion. LC-MS/MS was carried out on an Agilent 6300 Ion-Trap LC/MS. HPLC separation employed a phenomenex Jupiter reverse phase HPLC column (5 micron, 150 mm, 2.00 mm); mobile phase ACN [0.1% formic acid])/water ([0.1% formic acid]). The resulting TIC and EIC were analyzed for anticipated m/z modified peptide fragments.

Calculated m/z for the active site peptide: TDICQGAL-GDCWLLAAIASLTLNETILHR (SEQ ID NO: 11). Theoretical m/z=3113.6 (+3) MW:1038.8, (+4) MW 779.2.

Calculated m/z for IAA modified active site peptide sequence: TDIC(Carbamidomethyl)QGALGDC(Carbamidomethyl)WLLAAIASLTLNETILHR (SEQ ID NO: 12). Theoretical m/z=3227.8 (+3); 1076.8, (+4); MW 807.6. Observed m/z=(+3) 1076.5; (+4) 807.7.

Calculated m/z for E-64 and IAA modified active site peptide sequence: Sequence—TDIC(Carbamidomethyl) QGALGDC (E64)WLLAAIASLTLNETILHR (SEQ ID NO: 13).

Theoretical m/z=3528.1 (+3); 1176.1, (+4); MW 882.1. Observed m/z=(+3); 1176.4, (+4) MW 882.8

Example 11: Competition Assay for Cal1 vs CathB Using the Biotinylated Epoxide Probe The appropriate inhibitor (5 μM) was pre-incubated in a mixture containing Cal1$_{cat}$ (2 μM), CathB (2 μM), TCEP (1 mM), and Ca$^{2+}$ (30 μM) for 10 min at 37° C. 23 (5 μM) was then added and the mixture incubated an additional 20 min. The reaction was quenched with EDTA (10 μM) and samples were ran using 4-16% SDS PAGE gel, subsequently transferred to PVDF membrane and visualized by Pierce ECL (Enhanced chemiluminescent) western blotting substrate. Intensity of each blot was calculated using densitometry software. Relative inhibition of each enzyme was calculated with respect to enzyme activity in the absence of inhibitor. Inhibitor preference to Cal1$_{cat}$ with respect to CathB, was calculated by dividing relative Cal1$_{cat}$ inhibition with relative CathB inhibition of that particular inhibitor.

Example 12: Calpain and Papain Inhibition Kinetics Studies

Full length porcine calpain (156 nM), or papain (236 μM) was added to a solution of 100 mM NaCl, 50 mM HEPES, pH 7.6, 1 mM TCEP, 30 μM Suc-LLVY-AMC substrate, and inhibitor (0.5 to 50 μM). Calpain reactions also contained CaCl$_2$ (1 mM and 100 mM for porcine and rat respectively). Both substrate and inhibitors were dissolved in acetonitrile/DMSO (1:1) with the exception of E-64, dissolved in water. Organic solvent remained <2% in all reactions, and most often <1%. Reactions were carried out in microtiter 96-well plates, with 150 μL per well, 30° C., and product formation was monitored over time by fluorescence (Ex/Em 346/444 nm, with 420 nm cutoff filter). Kinetic values of k$_{obs}$ were determined via non-linear regression using one-phase association analysis and linear plots of 1/k$_{obs}$ vs. 1/[I] provided kinetic constants k$_i$ and K$_I$.

Example 13: Tests of Synaptic Dysfunction

Figure 9:
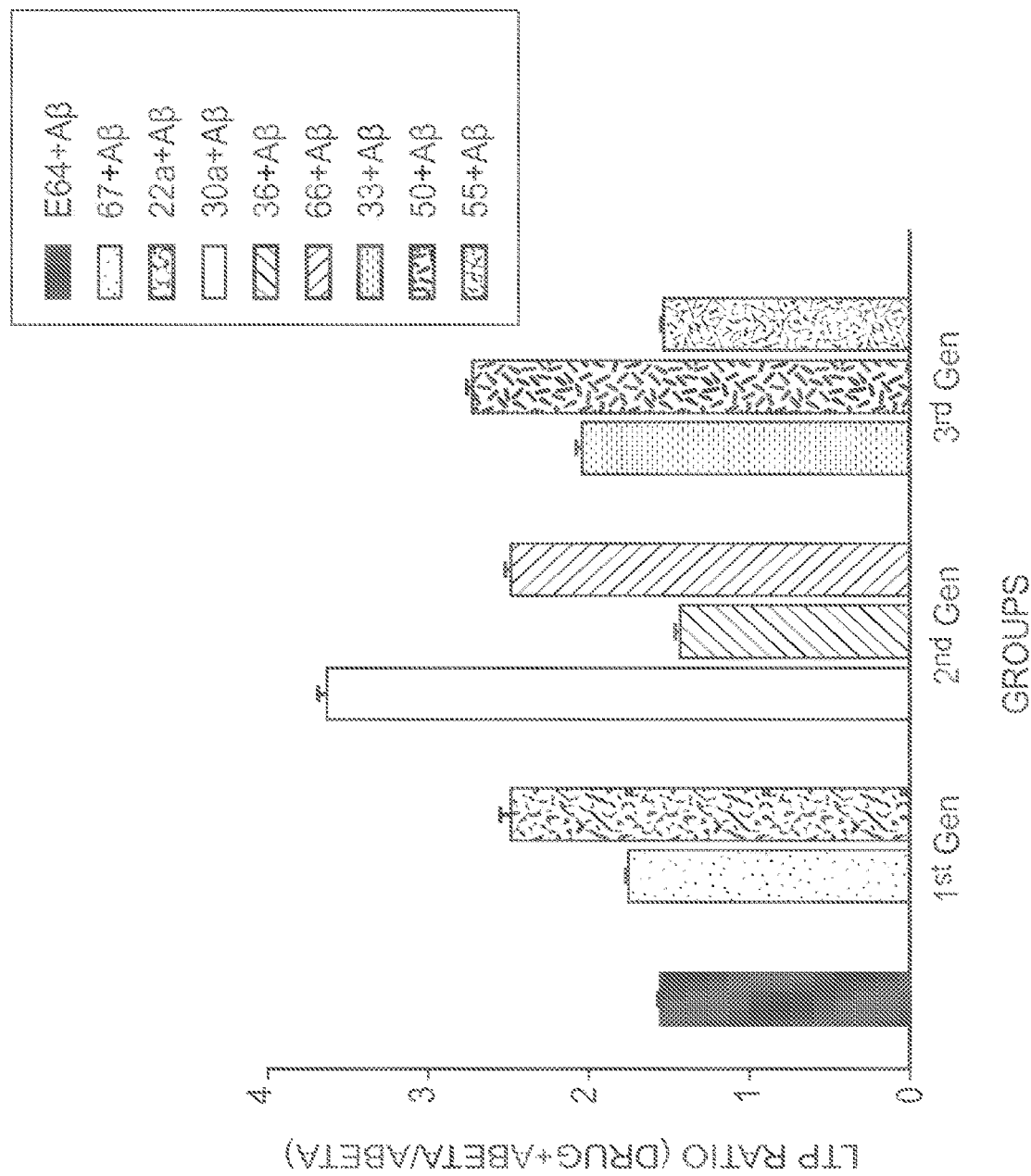
FIG. 9 shows residual potentiation during the last 5 min following administration of epoxides. Residual levels of potentiation were averaged during the last 5 min of LTP. The compounds were tested for ability to rescue the Aβ-induced LTP impairment ($P<0.05$).

With respect to screening our optimized compounds against synaptic dysfunction, we have used the LTP rescue test. Compounds 67, 22a, 30a, 36, 66, 33, 50 and 55 were assessed at values of amyloid-beta equal to 650 nM, corresponding to the ED$_{50}$ for E64 (as a benchmark). Compounds 67, 22a, 66, 33, and 50 surpassed E64 in potency for LTP rescue (FIG. 9). By contrast, 36 and 55 did not surpass it.

Example 14: Preliminary Toxicity Profile of Selected Compounds

For evaluation of acute and chronic toxicity we measured the maximum tolerated dose (MTD) in mice for 30a, 33 and 50. MTD was computed as the maximum administered dose that does not produce any toxicity effect in terms of malaise or death. MTD was set at the dose of 100 mg/kg for 30a, 150 mg/kg for 33, and 200 mg/kg for 50. All these doses were >10 times the dose used in the efficacy study. Evaluation of acute toxicity revealed no clinical signs of toxicity for the three compounds. With regard to the evaluation of the chronic toxicity, the histopathological evidences did not denounce a generalized toxicity induced by the chronic treatment at MTD for the three compounds. However, nephrotoxicity was noticed in the 30a-treated group as evidenced by the isometrical vacuolization, probably associated to osmolarity adjustment.

Example 15: Preliminary Pharmacokinetic Profile of Selected Compounds

Figure 10:
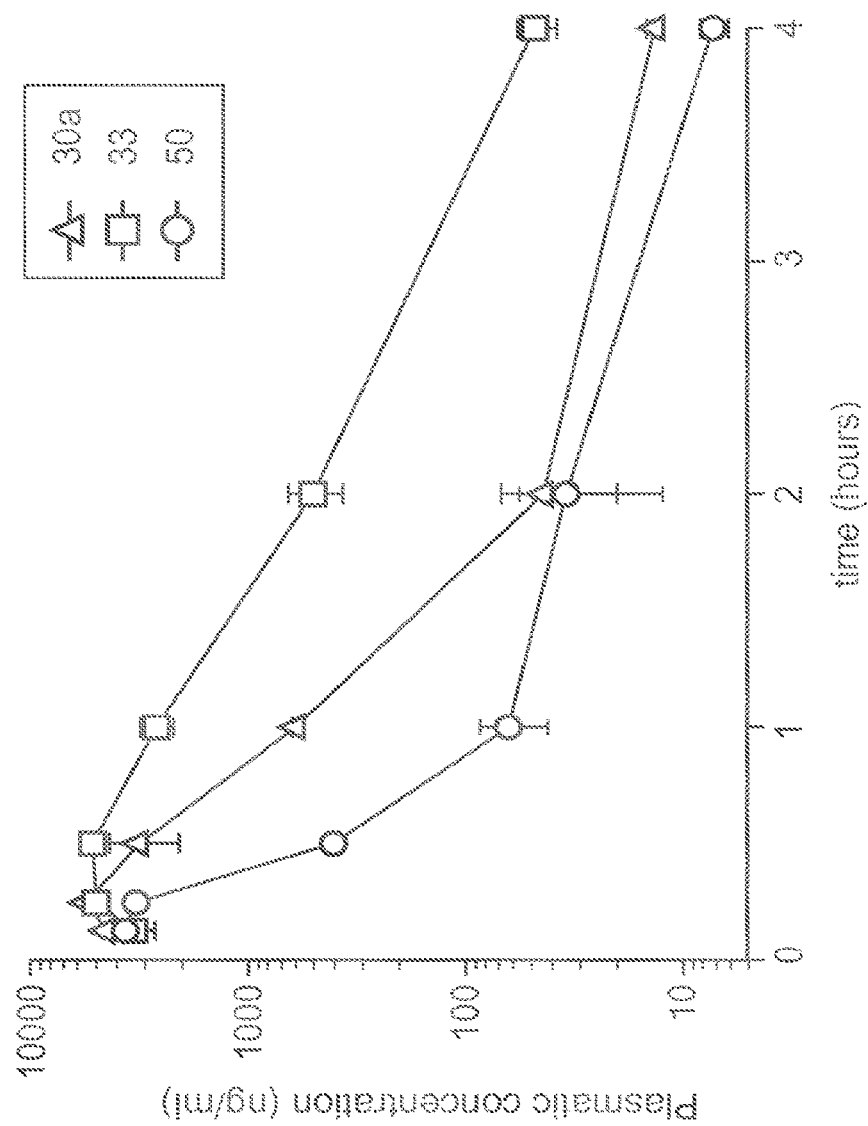
FIG. 10 shows plasma concentration versus time curves for selected compounds in mice (n=3 mice per group).

Plasma concentrations of 30a, 33 and 50 were determined by LC-MS/MS after i.p. administration to ICR mice. The plasma concentrations at each sampling time are shown on FIG. 10. The analysis of kinetics indicates that all three candidate compounds are rapidly absorbed upon i.p. injection. Indeed, following i.p. administration of 30a (7.57 mg/kg), 33 (7.86 mg/kg) and 50 (7.83 mg/kg), the peak plasma concentration occurred at 0.25, 0.5 and 0.125 h after dosing, respectively. The absolute bioavailability of 30a, 33 and 50 after i.p. administration was 80.4%, 87.3% and 41.3%, respectively. The respective half-lives were ~0.6 hrs, ~1.1 hrs and ~0.6 hrs.

Example 16: Evaluation of Brain Drug Activity of Selected Compounds

Figure 11:
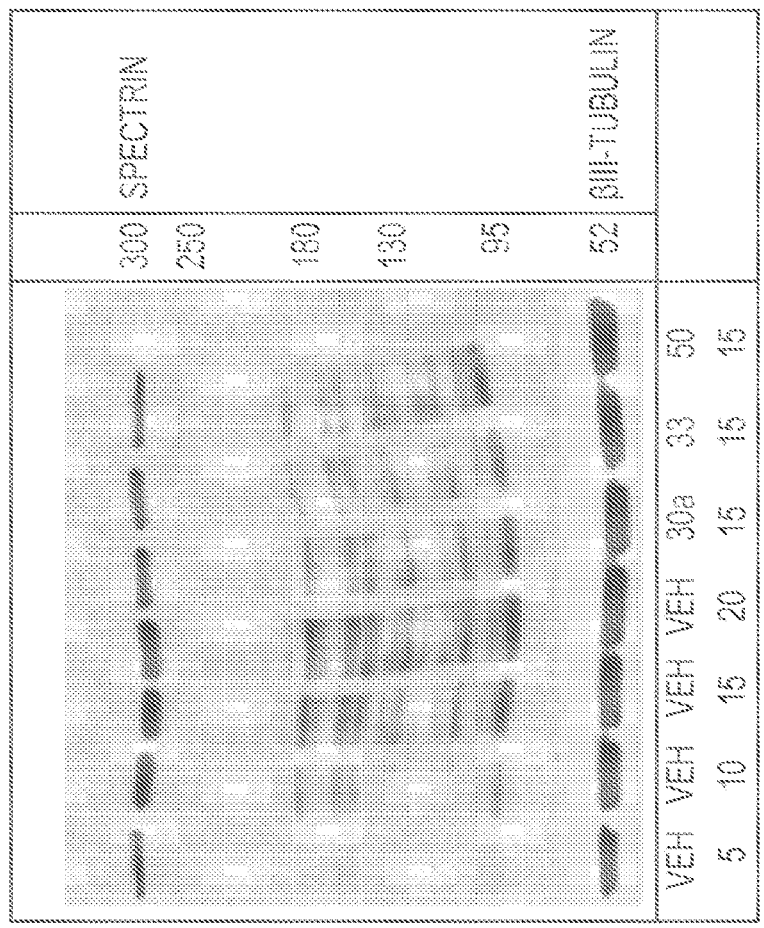
FIG. 11 shows Western blotting from hippocampi homogenates obtained from animals treated with vehicle, 30a, 33 and 50.

Studies were performed to determine capability of lowering levels of spectrin proteolytic degradation products in hippocampi from adult animals. Using western blot analysis, prevention of calpain-generated spectrin fragments was checked following i.p. treatment for 12 days with 30a, 33 and 50 at the same concentrations used for PK assessment. Western blotting form hippocampi homogenates obtained from animals treated with vehicle, 30a, 33 and 50 are shown in FIG. 11. The array of vehicle samples was obtained by loading samples with 5, 10, 15, and 20 µg total protein/lane. Samples from compound treated animals were loaded at 15 µg/lane. Compound 30a was less efficient at preventing the spectrin cleavage by calpains while the remaining two compounds 33 and 50 dramatically reduced the amount of fragments. Furthermore, 33 and 50 were capable of effectively penetrating the brain.

Example 17: Behavioral Rescue Assays

The ability of compounds to rescue the defects in associative and reference memory in 3 month old APP/PS1 animals was assessed. Capability of ameliorating the defects in contextual fear memory was tested via i.p. administration (FIG. 12). In the 2-day RAWM test, daily injections of the 67, 30a, 33 and 50 from the 2nd month of age were beneficial against the loss of contextual fear memory and reference memory.

Figure 13A:
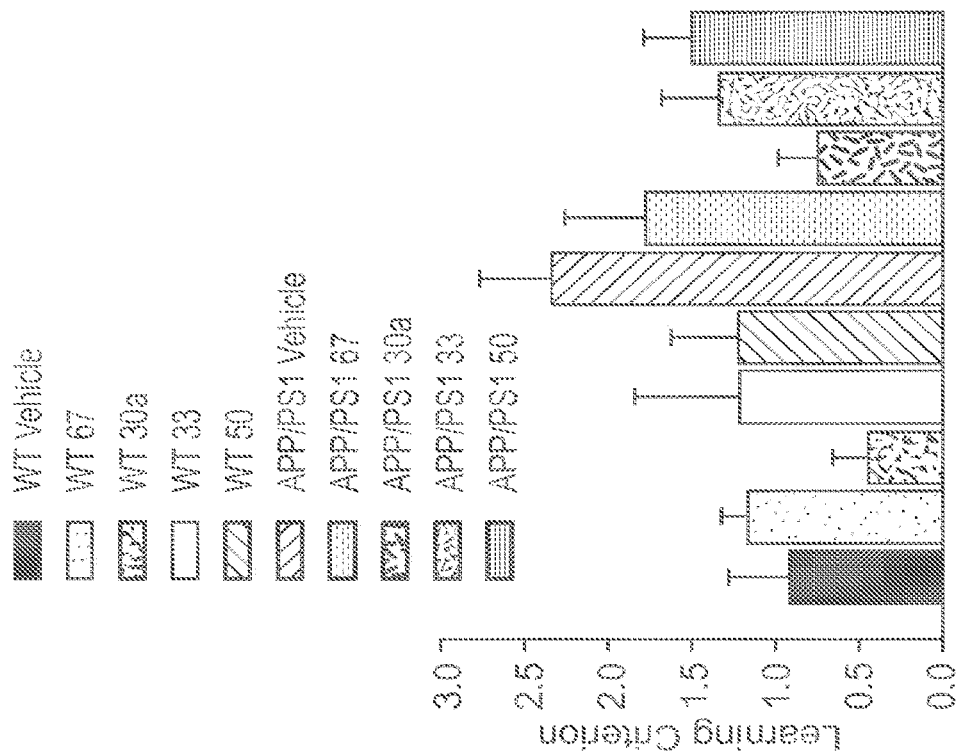
FIG. 13A-13B shows daily treatment with 67, 30a, 33 and 50 from the age of 2 months until 7 months ameliorated the defect in contextual fear memory (A) and reference memory (B) in APP/PS1 mice. APP/PS1-vehicle: n=17; APP/PS1-67: n=9; APP/PS1-30a: n=10; WT-vehicle: n=18; WT-67=9; WT-30a: n=9, APP/PS1-33: n=10; WT-33: n=9, APP/PS1-50: n=1; WT-50: n=9. $P<0.05$ in all transgenic groups treated with compound compared to their respective vehicle-treated transgenics (except for 67 reference memory which was not significant).
Figure 13B:
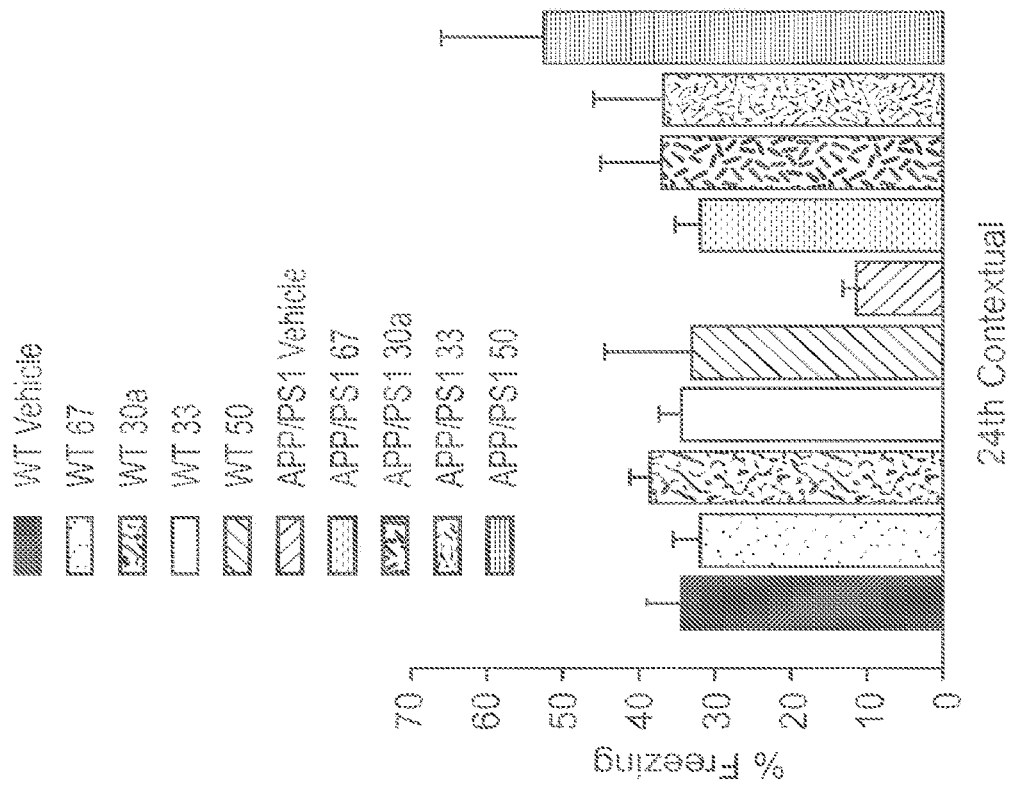

Impact of chronic treatment on against memory loss in older APP/PS1 mice (7 months of age) with a more severe plaque load was also investigated. Compounds 67, 33 and 50 were beneficial against memory impairment following chronic administration (FIG. 13).

Figure 14:
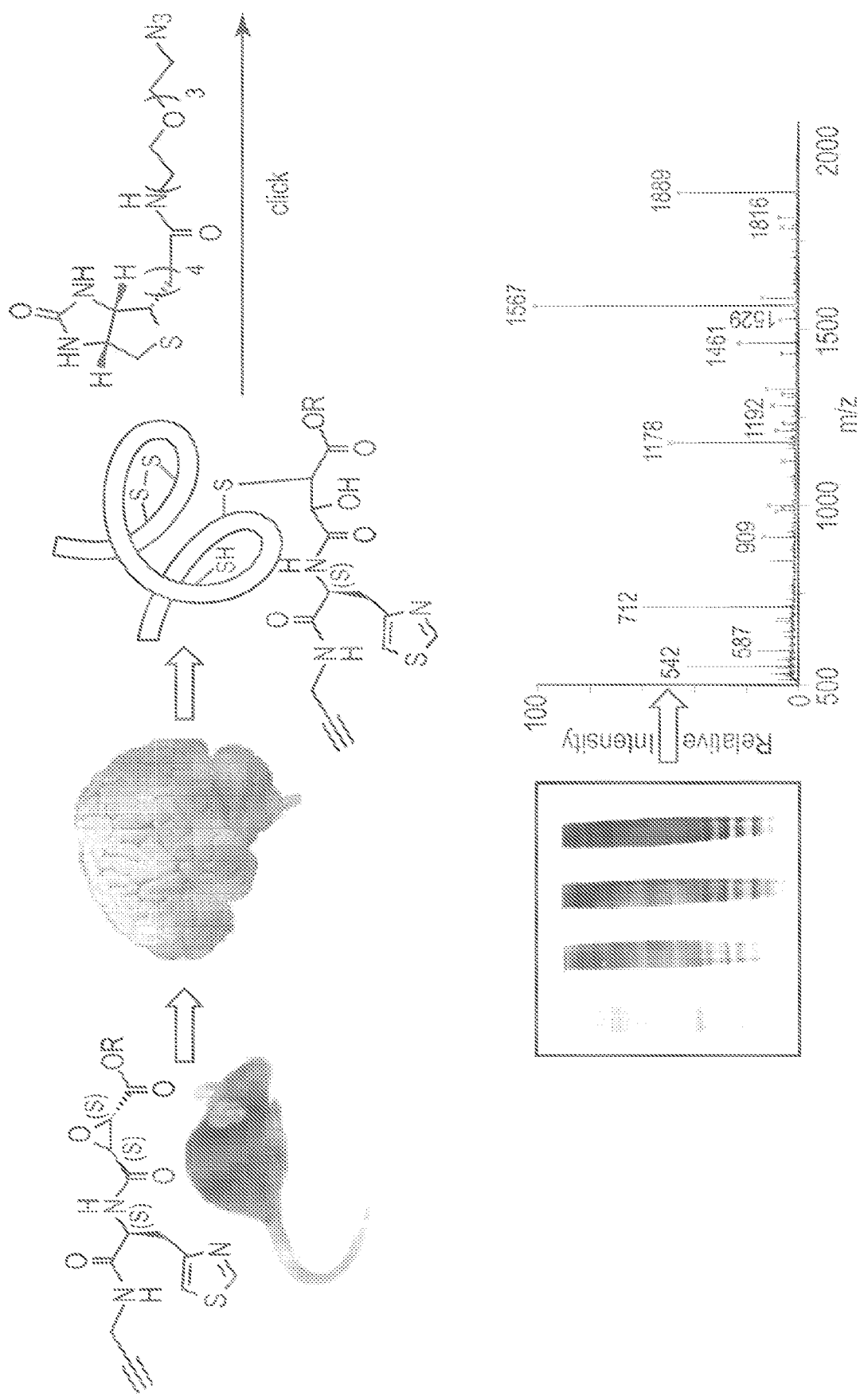
FIG. 14 shows analysis using clicked conjugates. Alkynyl epoxide is administered to mice, which are sacrificed at 10 and 30 min, followed by perfusion and brain excision. Proteins including those modified by alkynyl epoxide are isolated from brain tissue and after filtering through an avidin column are clicked to a biotinyl azide. Western blotting with streptavidin-HRP visualizes drug-modified proteins. In-gel digest and LC-MS/MS proteomic analysis identifies modified protein targets.

Example 18: Confirmation of Drug Action in the Brain Using Clicked Conjugates PK analysis in ICR mice revealed very low brain bioavailability. This presented a conundrum given the precognitive activity in vivo of drugs and the reduced calpain-mediated hippocampal spectrin cleavage. Brain and plasma bioavailability were confirmed by LC-MS/MS at UIC in $C_{57}$/BL6 mice. Possible explanations for this conundrum are: 1) covalent bonds of the compound with proteins; 2) tight, but reversible bonds with proteins; 3) extensive metabolism in vivo. To discriminate between these possibilities further assessment suggested that the compound is bound to albumin, which in turn masks the transportation through the BBB. In an effort to ameliorate the PK of the compounds, the synthesis of prodrugs has also been undertaken. Covalent modification of the active site of calpain 1 is part of the drug MOA. To address this issue, 2 N3-tagged derivatives have been prepared (FIG. 14). Alkynyl epoxide compounds 34 or 88 are administered to mice, which are sacrificed at 10 and 30 min, followed by perfusion and brain excision. Proteins including those modified by the alkynyl epoxide are isolated from brain tissue and after filtering through an avidin column are clicked to a biotinyl azide. Western blotting with streptavidin-HRP visualizes drug-modified proteins. In-gel digest and LC-MS/MS proteomic analysis identifies modified protein targets. Positive western blot will confirm that drugs penetrate the BBB. Proteomic analysis is not absolutely required, however, could be considered as future value-added experiments supporting MOA.

Example 19: Behavioral Rescue Assays for Prodrugs

Figure 15A:
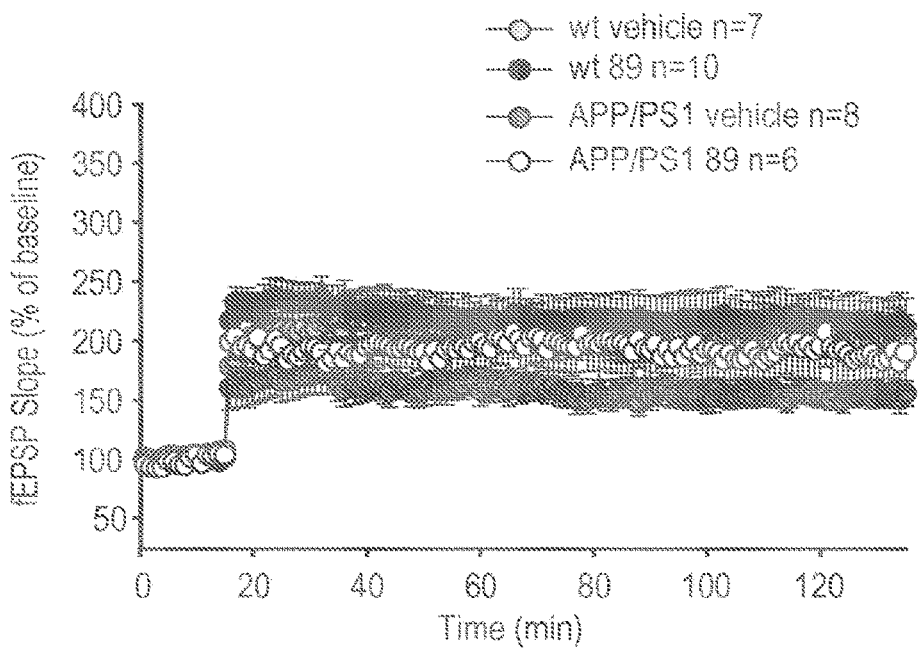
FIG. 15A-15C shows daily treatment with 89 from the age of 2 months until 3 months ameliorated the defect in LTP (A), contextual fear memory (B) and reference memory (C) in APP/PS1 mice. n=10 for all groups unless otherwise indicated. $P<0.05$ in transgenics treated with compound compared to their respective vehicle-treated transgenics.
Figure 15B:
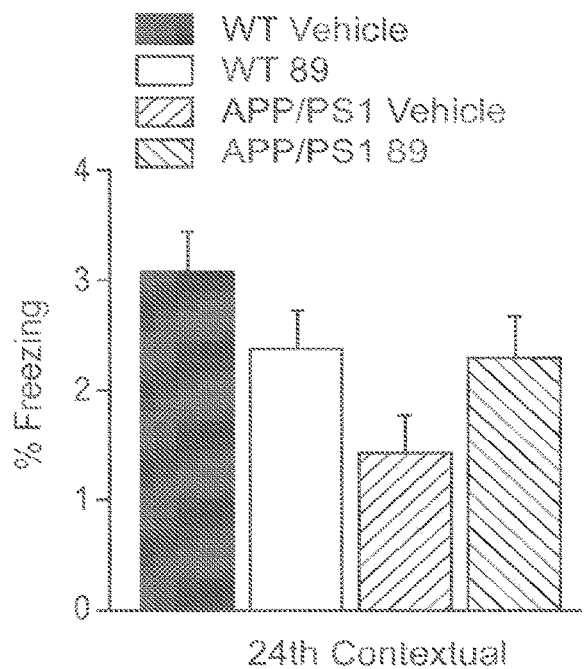
Figure 15C:
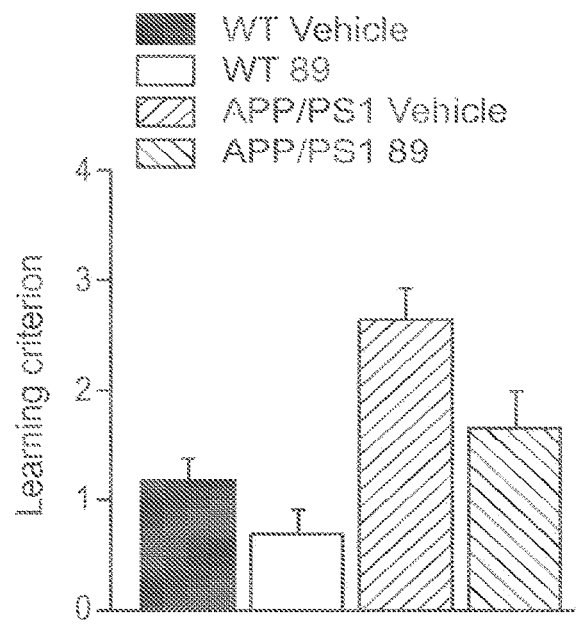

The ability of a prodrug to rescue the defects in associative and reference memory in 3 month old APP/PS1 animals was assessed. Esterified compounds showed increased BBB penetration vs. acid congeners. However, the esterified compounds showed also: a) increased reactivity toward GSH, generating rapid opening of reactive 2 rings; b) generalized reactivity toward other SH-reactive targets, possibly any protein target with reactive cysteines; c) poor prodrug behavior leading to decreased activity of the inhibitors; d) the in vivo effect even in presence of a poor PK/PD suggests multiple mechanisms of action; e) possibly higher selectivity for calpain 1 despite lower inhibitory activity. Thus, the esterification seems to improve PK but it spoils PD parameters. Compound 89 ameliorates both LTP and memory in 3 month old APP/PS1 mice (FIG. 15). Daily treatment with 89 from the age of 2 months until 3 months ameliorated the defect in LTP (A) contextual fear memory (B) and reference memory (C) in APP/PS1 mice. n=10 for all groups. $P<0.05$ in transgenics treated with compound compared to their respective vehicle-treated transgenics.

Example 20: Effect on Aβ Levels in APP/PS1 Mice

Figure 16A:
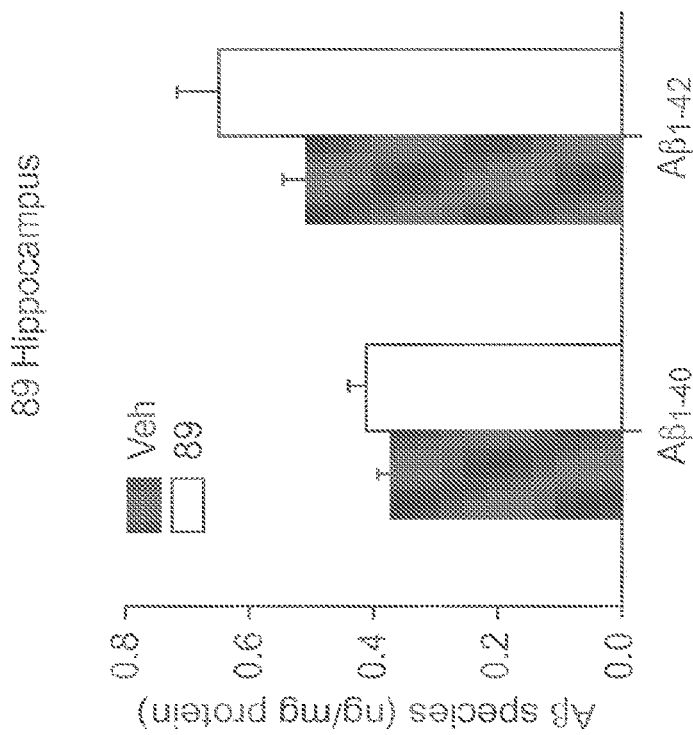
FIGS. 16A-16B shows Aβ40 and Aβ42 levels in hippocampi of 5-month-old APP/PS1 mice following treatment with 33 (A) and 89 (B) (n=5 for various groups).
Figure 16B:
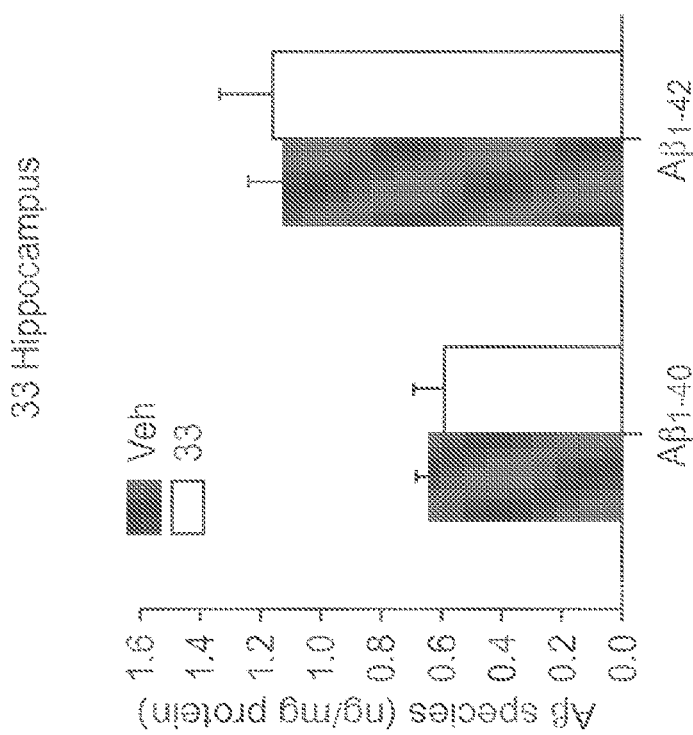

Increase of brain and plasma levels of Aβ and appearance of amyloid plaques is an important feature of AD. Thus, although E64 and BDA-410 do not have any effect on Aβ levels and plaque load, analysis of the effect of the novel calpain inhibitors by measuring Aβ 40 and 42 on brain tissue and blood samples taken from animals treated with 33 and 89 was performed. As observed with E64 and BDA-410 no difference was detected between hippocampi of compound-treated transgenics and vehicle-treated transgenics (FIG. 16). Similar results were obtained in cortex.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and/or rearranged in various ways within the scope and spirit of the invention to produce further embodiments that are also within the scope of the invention. Those skilled in the art will recognize, or be able to ascertain, using no more than routine experimentation, numerous equivalents to the specific embodiments described specifically in this disclosure. Such equivalents are intended to be encompassed in the scope of the following claims.

What is claimed:

1. A method of treating Alzheimer's disease in a subject in need thereof comprising administration of a therapeutically effective amount of a compound having a structure of formula (I-a):

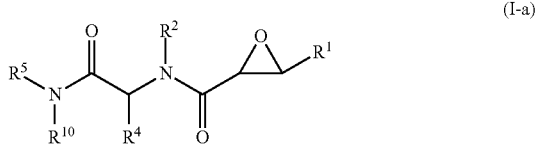
(I-a)

wherein,
$R^1$ is $CO_2H$ or $—CO_2(C_1-C_4)$-alkyl;
$R^2$ is hydrogen or $—(C_1-C_4)$-alkyl;
$R^4$ is $—(CH_2)$-thiazolyl;
$R^5$ is $—(C_1-C_6)$-alkyl-$R^6$, $—(C_2-C_5)$-alkenyl, $—(C_2-C_5)$-alkynyl, $—(CH_2)_n$-aryl, or
$—(CH_2)_n$-heteroaryl, wherein said aryl or heteroaryl are substituted with one or more $R^7$ groups;
$R^6$ is $—N(R^{10})C(O)R^8$ or $—N(R^{10})S(O)_2R^8$;
$R^7$ is independently halogen, $—(C_1-C_3)$-alkyl, aryl, methylenedioxyphenyl, or $—S(O)_2N(R^{10})_2$, wherein said aryl is optionally substituted with one or more $R^9$ groups;
$R^8$ is-$(C_1-C_6)$-alkyl-$R^{11}$ or aryl, wherein aryl is optionally substituted with one or more $R^9$ groups;
$R^9$ is independently hydrogen, halogen, $—(C_1-C_4)$-alkyl, $—(C_1-C_4)$-haloalkyl, $—(C_2-C_4)$-alkynyl, CN, $NO_2$, $—S(O)_2N(R^{10})_2$, or

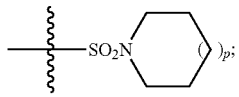

$R^{10}$ is independently hydrogen or $—(C_1-C_4)$-alkyl;
$R^{11}$ is hydrogen of

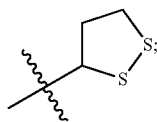

n is an integer from 0-4; and
p is an integer from 0-3.

2. A method of increasing long-term potentiation in a subject comprising administration of a therapeutically effective amount of a compound having a structure of formula (I-a),

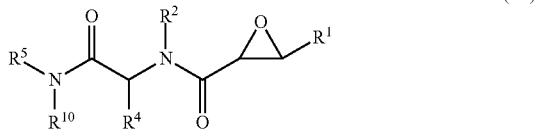
(I-a)

wherein,
$R^1$ is $CO_2H$ or $—CO_2(C_1-C_4)$-alkyl;
$R^2$ is hydrogen or $—(C_1-C_4)$-alkyl;
$R^4$ is $—(CH_2)$-thiazolyl;
$R^5$ is-$(C_1-C_6)$-alkyl-$R^6$, $—(C_2-C_5)$-alkenyl, $—(C_2-C_5)$-alkynyl, $—(CH_2)_n$-aryl, or
$(CH_2)_n$-heteroaryl, wherein said aryl or heteroaryl are substituted with one or more $R^7$ groups;
$R^6$ is $—N(R^{10})C(O)R^8$ or $—N(R^{10})S(O)_1R^8$;
$R^7$ is independently halogen, $—(C_1-C_3)$-alkyl, aryl, methylenedioxyphenyl, or $—S(O)_2N(R^{10})_2$, wherein said aryl is optionally substituted with one or more $R^9$ groups;
$R^8$ is-$(C_1-C_6)$-alkyl-$R^{11}$ or aryl, wherein aryl is optionally substituted with one or more $R^9$ groups;
$R^9$ is independently hydrogen, halogen, $—(C_1-C_4)$-alkyl, $—(C_1-C_4)$-haloalkyl, $—(C_2-C_4)$-alkynyl, CN, $NO_2$, $—S(O)_2N(R^{10})_2$, or

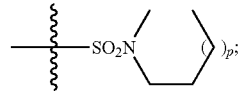

$R^{10}$ is independently hydrogen or $—(C_1-C_4)$-alkyl;
$R^{11}$ is hydrogen or

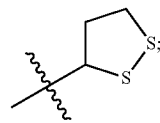 [SMILES: *C1CCSS1]

n is an integer from 0-4; and
p is an integer from 0-3.

3. A method of improving memory in a subject comprising administration of a therapeutically effective amount of a compound having a structure of formula (I-a),

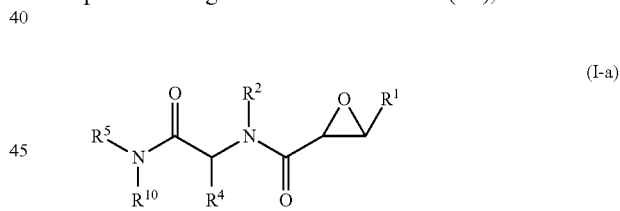
(I-a)

wherein,
$R^1$ is $CO_2H$ or $—CO_2(C_1-C_4)$-alkyl;
$R^2$ is hydrogen or $—(C_1-C_4)$-alkyl;
$R^4$ is $—(CH_2)$-thiazolyl;
$R^5$ is-$(C_1-C_6)$-alkyl-$R^6$, $—(C_2-C_5)$-alkenyl, $—(C_2-C_5)$-alkynyl, $—(CH_2)_n$-aryl, or
$(CH_2)_n$-heteroaryl, wherein said aryl or heteroaryl are substituted with one or more $R^7$ groups;
$R^6$ is $—N(R^{10})C(O)R^8$ or)-$N(R^{10})S(O)_2R^8$;
$R^7$ is independently halogen, $—(C_1-C_3)$-alkyl, aryl, methylenedioxyphenyl, or $—S(O)_2N(R^{10})_2$, wherein said aryl is optionally substituted with one or more $R^9$ groups;
$R^8$ is-$(C_1-C_6)$-alkyl-$R^{11}$ or aryl, wherein aryl is optionally substituted with one or more $R^9$ groups;
$R^9$ is independently hydrogen, halogen, $—(C_1-C_4)$-alkyl, $—(C_1-C_4)$-haloalkyl, $—(C_2-C_4)$-alkynyl, CN, $NO_2$,— $S(O)_2N(R^{10})_2$, or

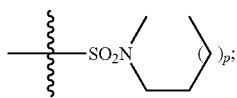

$R^{10}$ is independently hydrogen or —($C_1$-$C_4$)-alkyl;
$R^{11}$ is hydrogen or

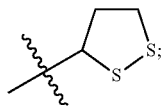

n is an integer from 0-4; and
p is an integer from 0-3.

4. The method of claim 3, wherein the subject has Alzheimer's Disease.

5. The method of claim 1, wherein the compound is formulated as a pharmaceutical composition.

6. The method of claim 5, wherein the pharmaceutical composition is formulated: as a sterile injectable solution or dispersion, for intravenous or oral administration, or for transmucosal or transdermal administration.

7. The method of claim 1, wherein
(a) $R^1$ is —$CO_2H$ or —$CO_1$($C_1$-$C_2$)-alkyl;
$R^2$ is hydrogen or —($C_1$-$C_2$)-alkyl;
$R^5$ is —$(CH_2)_n$-phenyl, or —$(CH_2)_n$-heteroaryl, wherein said phenyl or heteroaryl are substituted with one or more $R^7$ groups;
$R^7$ is independently halogen, —($C_1$-$C_3$)-alkyl, phenyl, methylenedioxyphenyl, or —$S(O)_2N(R^{10})_2$, wherein said phenyl is optionally substituted with one or more $R^9$ groups;
$R^9$ is independently hydrogen, halogen, —($C_1$-$C_2$)-alkyl, —($C_1$-$C_2$)-haloalkyl, —($C_2$-$C_4$)-alkynyl, CN, $NO_2$, —$S(O)_2N(R^{10})_2$, or

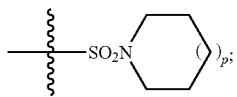

$R^{10}$ is independently hydrogen or —($C_1$-$C_2$)-alkyl;
n is an integer from 0-2; and
p is an integer from 0-1;
(b) $R^1$ is —$CO_2H$ or —$CO_2$($C_1$-$C_2$)-alkyl;
$R^2$ is hydrogen or —($C_1$-$C_2$)-alkyl;
$R^5$ is —$(CH_2)$-triazolyl, wherein said triazolyl is substituted with an $R^7$ group;
$R^7$ is phenyl optionally substituted with one or more $R^9$ groups;
$R^9$ is independently halogen, —($C_1$-$C_2$)-alkyl, —($C_1$-$C_2$)-haloalkyl, —($C_2$-$C_4$)-alkynyl, CN, $NO_2$, —$S(O)_2N(R^{10})_2$, or

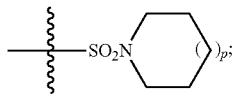

$R^{10}$ is independently hydrogen or —($C_1$-$C_2$)-alkyl; and p is an integer from 0-1;
(c) $R^1$ is —$CO_2H$ or —$CO_2$($C_1$-$C_2$)-alkyl;
$R^2$ is hydrogen or —($C_1$-$C_2$)-alkyl;
$R^5$ is —$(CH_2)$-triazolyl, wherein said triazolyl is substituted with an $R^7$ group;
$R^7$ is phenyl optionally substituted with one or more $R^9$ groups;
$R^9$ is independently halogen, —($C_1$-$C_2$)-alkyl, —($C_1$-$C_2$)-haloalkyl, —($C_2$-$C_4$)-alkynyl, CN, $NO_2$, —$S(O)_2N(R^{10})_2$, or

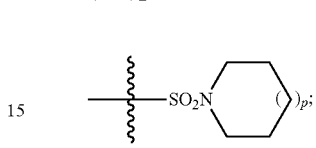

$R^{10}$ is independently hydrogen or methyl; and
p is an integer from 0-1; or
(d) $R^1$ is —$CO_2H$ or —$CO_2$($C_1$-$C_2$)-alkyl;
$R^2$ is hydrogen;
$R^5$ is

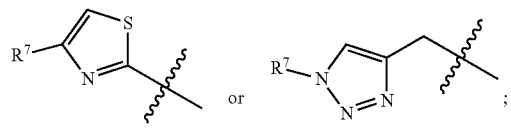

$R^7$ is phenyl optionally substituted with one or more $R^9$ groups;
$R^9$ is independently halogen, —($C_1$-$C_2$)-alkyl, —($C_1$-$C_2$)-haloalkyl, —($C_2$-$C_3$)-alkynyl, $NO_2$, —$S(O)_2NH_2$, or

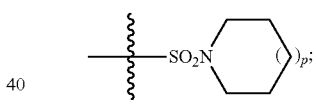

and
p is an integer from 0-1.

8. The method of claim 1, wherein the compound is:
(2S,3S)-3-((S)-1-(4-(4-fluorophenyl)thiazol-2-ylamino)-1-oxo-3-(thiazol-4-yl)propan-2-ylcarbamoyl)oxirane-2-carboxylic acid;
(2S,3S)-3-((S)-1-(4-(4-ethynylphenyl)thiazol-2-ylamino)-1-oxo-3-(thiazol-4-yl)propan-2-ylcarbamoyl)oxirane-2-carboxylic acid;
(2S,3S)-3-((S)-1-((1-(4-fluorophenyl)-1H-1,2,3-triazol-4-yl)methylamino)-1-oxo-3-(thiazol-4-yl)propan-2-ylcarbamoyl)oxirane-2-carboxylic acid; or
(2S,3S)-3-((S)-1-((1-(4-bromophenyl)-1H-1,2,3-triazol-4-yl)methylamino)-1-oxo-3-(thiazol-4-yl)propan-2-ylcarbamoyl)oxirane-2-carboxylic acid.

9. The method of claim 2, wherein the compound is:
(2S,3S)-3-((S)-1-(4-(4-fluorophenyl)thiazol-2-ylamino)-1-oxo-3-(thiazol-4-yl)propan-2-ylcarbamoyl)oxirane-2-carboxylic acid;
(2S,3S)-3-((S)-1-(4-(4-ethynylphenyl)thiazol-2-ylamino)-1-oxo-3-(thiazol-4-yl)propan-2-ylcarbamoyl)oxirane-2-carboxylic acid;
(2S,3S)-3-((S)-1-((1-(4-fluorophenyl)-1H-1,2,3-triazol-4-yl)methylamino)-1-oxo-3-(thiazol-4-yl)propan-2-ylcarbamoyl)oxirane-2-carboxylic acid; or (2S,3S)-3-((S)-1-((1-(4-bromophenyl)-1H-1,2,3-triazol-4-yl)methylamino)-1-oxo-3-(thiazol-4-yl)propan-2-ylcarbamoyl)oxirane-2-carboxylic acid.

10. The method of claim 3, wherein the compound is:
(2S,3S)-3-((S)-1-(4-(4-fluorophenyl)thiazol-2-ylamino)-1-oxo-3-(thiazol-4-yl)propan-2-ylcarbamoyl)oxirane-2-carboxylic acid;
(2S,3S)-3-((S)-1-(4-(4-ethynylphenyl)thiazol-2-ylamino)-1-oxo-3-(thiazol-4-yl)propan-2-ylcarbamoyl)oxirane-2-carboxylic acid;
(2S,3S)-3-((S)-1-((1-(4-fluorophenyl)-1H-1,2,3-triazol-4-yl)methylamino)-1-oxo-3-(thiazol-4-yl)propan-2-ylcarbamoyl)oxirane-2-carboxylic acid; or
(2S,3S)-3-((S)-1-((1-(4-bromophenyl)-1H-1,2,3-triazol-4-yl)methylamino)-1-oxo-3-(thiazol-4-yl)propan-2-ylcarbamoyl)oxirane-2-carboxylic acid.

11. The method of claim 2, wherein the compound is formulated as a pharmaceutical composition.

12. The method of claim 11, wherein the pharmaceutical composition is formulated: as a sterile injectable solution or dispersion, for intravenous or oral administration, or for transmucosal or transdermal administration.

13. The method of claim 3, wherein the compound is formulated as a pharmaceutical composition.

14. The method of claim 13, wherein the pharmaceutical composition is formulated: as a sterile injectable solution or dispersion, for intravenous or oral administration, or for transmucosal or transdermal administration.

15. The method of claim 1, wherein
$R^1$ is —$CO_2H$ or —$CO_2(C_1$-$C_4)$-alkyl;
$R^2$ is hydrogen or —$(C_1$-$C_4)$-alkyl;
$R^4$ is

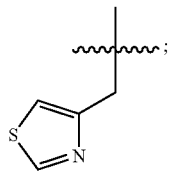 [SMILES: *Cc1cscn1]

$R^5$ is -$(C_1$-$C_4)$-alkyl-$R^6$, —$(CH_2)_n$-aryl, or —$(CH_2)_n$-heteroaryl, wherein said aryl or heteroaryl are substituted with one or more $R^7$ groups;
$R^6$ is —$N(R^{10})C(O)R^8$ or —$N(R^{10})S(O)_2R^8$;
$R^7$ is independently halogen, —$(C_1$-$C_3)$-alkyl, aryl, methylenedioxyphenyl, or —$S(O)_2N(R^{10})_2$, wherein said aryl is optionally substituted with one or more $R^9$ groups;
$R^8$ is -$(C_1$-$C_6)$-alkyl-$R^{11}$ or aryl, wherein aryl is optionally substituted with one or more $R^9$ groups;
$R^9$ is independently hydrogen, halogen, —$(C_1$-$C_2)$-alkyl, —$(C_1$-$C_2)$-haloalkyl, —$(C_2$-$C_4)$-alkynyl, CN, $NO_2$, —$S(O)_2N(R^{10})_2$, or

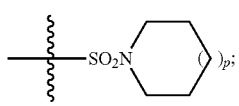

$R^{10}$ is independently hydrogen or —$(C_1$-$C_4)$-alkyl;
$R^{11}$ is hydrogen or

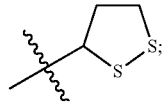 [SMILES: *C1CCSS1]

n is an integer from 0-2; and
p is an integer from 0-1.

16. The method of claim 2, wherein
$R^1$ is —$CO_2H$ or —$CO_2(C_1$-$C_4)$-alkyl;
$R^2$ is hydrogen or —$(C_1$-$C_4)$-alkyl;
$R^4$ is

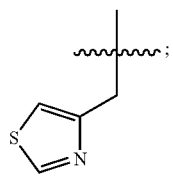 [SMILES: *Cc1cscn1]

$R^5$ is -$(C_1$-$C_4)$-alkyl-$R^6$, —$(CH_2)_n$-aryl, or —$(CH_2)_n$-heteroaryl, wherein said aryl or heteroaryl are substituted with one or more $R^7$ groups;
$R^6$ is —$N(R^{10})C(O)R^8$ or —$N(R^{10})S(O)_2R^8$;
$R^7$ is independently halogen, —$(C_1$-$C_3)$-alkyl, aryl, methylenedioxyphenyl, or —$S(O)_2N(R^{10})_2$, wherein said aryl is optionally substituted with one or more $R^9$ groups;
$R^8$ is -$(C_1$-$C_6)$-alkyl-$R^{11}$ or aryl, wherein aryl is optionally substituted with one or more $R^9$ groups;
$R^9$ is independently hydrogen, halogen, —$(C_1$-$C_2)$-alkyl, —$(C_1$-$C_2)$-haloalkyl, —$(C_2$-$C_4)$-alkynyl, CN, $NO_2$, —$S(O)_2N(R^{10})_2$, or

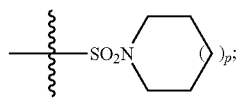

$R^{10}$ is independently hydrogen or —$(C_1$-$C_4)$-alkyl;
$R^{11}$ is hydrogen or

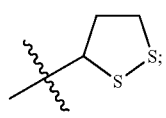 [SMILES: *C1CCSS1]

n is an integer from 0-2; and
p is an integer from 0-1.

17. The method of claim 3, wherein
$R^1$ is —$CO_2H$ or —$CO_2(C_1$-$C_4)$-alkyl;
$R^2$ is hydrogen or —$(C_1$-$C_4)$-alkyl;
$R^4$ is

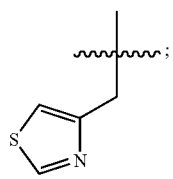 [SMILES: *Cc1cscn1]

$R^5$ is -($C_1$-$C_4$)-alkyl-$R^6$, —($CH_2$)$_n$-aryl, or —($CH_2$)$_n$-heteroaryl, wherein said aryl or heteroaryl are substituted with one or more $R^7$ groups;

$R^6$ is —N($R^{10}$)C(O)$R^8$ or —N($R^{10}$)S(O)$_2R^8$;

$R^7$ is independently halogen, —($C_1$-$C_3$)-alkyl, aryl, methylenedioxyphenyl, or —S(O)$_2$N($R^{10}$)$_2$, wherein said aryl is optionally substituted with one or more $R^9$ groups;

$R^8$ is -($C_1$-$C_6$)-alkyl-$R^{11}$ or aryl, wherein aryl is optionally substituted with one or more $R^9$ groups;

$R^9$ is independently hydrogen, halogen, —($C_1$-$C_2$)-alkyl, —($C_1$-$C_2$)-haloalkyl, —($C_2$-$C_4$)-alkynyl, CN, $NO_2$, —S(O)$_2$N($R^{10}$)$_2$, or

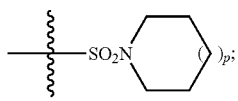

$R^{10}$ is independently hydrogen or —($C_1$-$C_4$)-alkyl;

$R^{11}$ is hydrogen or

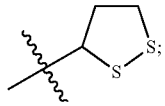

n is an integer from 0-2; and p is an integer from 0-1.

* * * * *

SEQUENCE LISTING

<160> NUMBER OF SEQ ID NOS: 13

<210> SEQ ID NO 1
<211> LENGTH: 360
<212> TYPE: PRT
<213> ORGANISM: Homo sapiens

<400> SEQUENCE: 1

Met Ser Glu Glu Ile Ile Thr Pro Val Tyr Cys Thr Gly Val Ser Ala
1               5                   10                  15

Gln Val Gln Lys Gln Arg Ala Arg Glu Leu Gly Leu Gly Arg His Glu
            20                  25                  30

Asn Ala Ile Lys Tyr Leu Gly Gln Asp Tyr Glu Gln Leu Arg Val Arg
        35                  40                  45

Cys Leu Gln Ser Gly Thr Leu Phe Arg Asp Glu Ala Phe Pro Pro Val
    50                  55                  60

Pro Gln Ser Leu Gly Tyr Lys Asp Leu Gly Pro Asn Ser Ser Lys Thr
65                  70                  75                  80

Tyr Gly Ile Lys Trp Lys Arg Pro Thr Glu Leu Leu Ser Asn Pro Gln
                85                  90                  95

Phe Ile Val Asp Gly Ala Thr Arg Thr Asp Ile Cys Gln Gly Ala Leu
            100                 105                 110

Gly Asp Cys Trp Leu Leu Ala Ala Ile Ala Ser Leu Thr Leu Asn Asp
        115                 120                 125

Thr Leu Leu His Arg Val Val Pro His Gly Gln Ser Phe Gln Asn Gly
    130                 135                 140

Tyr Ala Gly Ile Phe His Phe Gln Leu Trp Gln Phe Gly Glu Trp Val
145                 150                 155                 160

Asp Val Val Val Asp Asp Leu Leu Pro Ile Lys Asp Gly Lys Leu Val
                165                 170                 175

Phe Val His Ser Ala Glu Gly Asn Glu Phe Trp Ser Ala Leu Leu Glu
            180                 185                 190

Lys Ala Tyr Ala Lys Val Asn Gly Ser Tyr Glu Ala Leu Ser Gly Gly
        195                 200                 205

Ser Thr Ser Glu Gly Phe Glu Asp Phe Thr Gly Gly Val Thr Glu Trp
    210                 215                 220

Tyr Glu Leu Arg Lys Ala Pro Ser Asp Leu Tyr Gln Ile Ile Leu Lys
225                 230                 235                 240

Ala Leu Glu Arg Gly Ser Leu Leu Gly Cys Ser Ile Asp Ile Ser Ser
                245                 250                 255

Val Leu Asp Met Glu Ala Ile Thr Phe Lys Lys Leu Val Lys Gly His
            260                 265                 270

Ala Tyr Ser Val Thr Gly Ala Lys Gln Val Asn Tyr Arg Gly Gln Val
        275                 280                 285

Val Ser Leu Ile Arg Met Arg Asn Pro Trp Gly Glu Val Glu Trp Thr
    290                 295                 300

Gly Ala Trp Ser Asp Ser Ser Ser Glu Trp Asn Asn Val Asp Pro Tyr
305                 310                 315                 320

Glu Arg Asp Gln Leu Arg Val Lys Met Glu Asp Gly Glu Phe Trp Met
                325                 330                 335

Ser Phe Arg Asp Phe Met Arg Glu Phe Thr Arg Leu Glu Ile Cys Asn
            340                 345                 350

Leu Thr Pro Asp Ala Leu Lys Ser
        355                 360

<210> SEQ ID NO 2
<211> LENGTH: 360
<212> TYPE: PRT
<213> ORGANISM: Sus scrofa

<400> SEQUENCE: 2

```
Met Ala Glu Glu Val Ile Thr Pro Val Tyr Cys Thr Gly Val Ser Ala
1               5                   10                  15

Gln Val Gln Lys Leu Arg Ala Lys Glu Leu Gly Leu Gly Arg His Glu
            20                  25                  30

Asn Ala Ile Lys Tyr Leu Gly Gln Asp Tyr Glu Gln Leu Arg Ala His
        35                  40                  45

Cys Leu Gln Ser Gly Ser Leu Phe Arg Asp Glu Ala Phe Pro Pro Val
    50                  55                  60

Pro Gln Ser Leu Gly Phe Lys Glu Leu Gly Pro Asn Ser Ser Lys Thr
65                  70                  75                  80

Tyr Gly Val Lys Trp Lys Arg Pro Thr Glu Leu Phe Ser Asn Pro Gln
                85                  90                  95

Phe Ile Val Asp Gly Ala Thr Arg Thr Asp Ile Cys Gln Gly Ala Leu
            100                 105                 110

Gly Asp Cys Trp Leu Leu Ala Ala Ile Ala Ser Leu Thr Leu Asn Asp
        115                 120                 125

Thr Leu Leu His Arg Val Val Pro His Gly Gln Ser Phe Gln Asn Gly
    130                 135                 140

Tyr Ala Gly Ile Phe His Phe Gln Leu Trp Gln Phe Gly Glu Trp Val
145                 150                 155                 160

Asp Val Val Val Asp Asp Leu Leu Pro Thr Lys Asp Gly Lys Leu Val
                165                 170                 175

Phe Val His Ser Ala Gln Gly Asn Glu Phe Trp Ser Ala Leu Leu Glu
            180                 185                 190

Lys Ala Tyr Ala Lys Val Asn Gly Ser Tyr Glu Ala Leu Ser Gly Gly
        195                 200                 205

Ser Thr Ser Glu Gly Phe Glu Asp Phe Thr Gly Gly Val Thr Glu Trp
    210                 215                 220

Tyr Glu Leu Arg Lys Ala Pro Ser Asp Leu Tyr Ser Ile Ile Leu Lys
225                 230                 235                 240

Ala Leu Glu Arg Gly Ser Leu Leu Gly Cys Ser Ile Asp Ile Ser Ser
                245                 250                 255

Val Leu Asp Met Glu Ala Val Thr Phe Lys Lys Leu Val Lys Gly His
            260                 265                 270

Ala Tyr Ser Val Thr Gly Ala Lys Gln Val Asn Tyr Gln Gly Gln Met
        275                 280                 285

Val Asn Leu Ile Arg Met Arg Asn Pro Trp Gly Glu Val Glu Trp Thr
    290                 295                 300

Gly Ala Trp Ser Asp Gly Ser Ser Glu Trp Asn Gly Val Asp Pro Tyr
305                 310                 315                 320

Gln Arg Asp Gln Leu Arg Val Arg Met Glu Asp Gly Glu Phe Trp Met
                325                 330                 335

Ser Phe Arg Asp Phe Leu Arg Glu Phe Thr Arg Leu Glu Ile Cys Asn
            340                 345                 350

Leu Thr Pro Asp Ala Leu Lys Ser
        355                 360
```

<210> SEQ ID NO 3

<211> LENGTH: 360
<212> TYPE: PRT
<213> ORGANISM: Mus musculus

<400> SEQUENCE: 3

```
Met Thr Glu Glu Leu Ile Thr Pro Val Tyr Cys Thr Gly Val Ser Ala
1               5                   10                  15

Gln Val Gln Lys Lys Arg Asp Lys Glu Leu Gly Leu Gly Arg His Glu
            20                  25                  30

Asn Ala Ile Lys Tyr Leu Gly Gln Asp Tyr Glu Thr Leu Arg Ala Arg
        35                  40                  45

Cys Leu Gln Ser Gly Val Leu Phe Gln Asp Glu Ala Phe Pro Pro Val
    50                  55                  60

Ser His Ser Leu Gly Phe Lys Glu Leu Gly Pro His Ser Ser Lys Thr
65                  70                  75                  80

Tyr Gly Ile Lys Trp Lys Arg Pro Thr Glu Leu Met Ser Asn Pro Gln
                85                  90                  95

Phe Ile Val Asp Gly Ala Thr Arg Thr Asp Ile Cys Gln Gly Ala Leu
            100                 105                 110

Gly Asp Cys Trp Leu Leu Ala Ala Ile Ala Ser Leu Thr Leu Asn Glu
        115                 120                 125

Thr Ile Leu His Arg Val Val Pro Tyr Gly Gln Ser Phe Gln Asp Gly
    130                 135                 140

Tyr Ala Gly Ile Phe His Phe Gln Leu Trp Gln Phe Gly Glu Trp Val
145                 150                 155                 160

Asp Val Val Ile Asp Asp Leu Leu Pro Thr Lys Asp Gly Lys Leu Val
                165                 170                 175

Phe Val His Ser Ala Gln Gly Asn Glu Phe Trp Ser Ala Leu Leu Glu
            180                 185                 190

Lys Ala Tyr Ala Lys Val Asn Gly Ser Tyr Glu Ala Leu Ser Gly Gly
        195                 200                 205

Cys Thr Ser Glu Ala Phe Glu Asp Phe Thr Gly Val Thr Glu Trp
    210                 215                 220

Tyr Asp Leu Gln Lys Ala Pro Ser Asp Leu Tyr Gln Ile Ile Leu Lys
225                 230                 235                 240

Ala Leu Glu Arg Gly Ser Leu Leu Gly Cys Ser Ile Asn Ile Ser Asp
                245                 250                 255

Ile Arg Asp Leu Glu Ala Ile Thr Phe Lys Asn Leu Val Arg Gly His
            260                 265                 270

Ala Tyr Ser Val Thr Gly Ala Lys Gln Val Thr Tyr Gln Gly Gln Arg
        275                 280                 285

Val Asn Leu Ile Arg Met Arg Asn Pro Trp Gly Glu Val Glu Trp Lys
    290                 295                 300

Gly Pro Trp Ser Asp Ser Ser Tyr Glu Trp Asn Lys Val Asp Pro Tyr
305                 310                 315                 320

Glu Arg Glu Gln Leu Arg Val Lys Met Glu Asp Gly Glu Phe Trp Met
                325                 330                 335

Ser Phe Arg Asp Phe Ile Arg Glu Phe Thr Lys Leu Glu Ile Cys Asn
            340                 345                 350

Leu Thr Pro Asp Ala Leu Lys Ser
        355                 360
```

<210> SEQ ID NO 4
<211> LENGTH: 360
<212> TYPE: PRT

<213> ORGANISM: Rattus norvegicus

<400> SEQUENCE: 4

Met Ala Glu Glu Leu Ile Thr Pro Val Tyr Cys Thr Gly Val Ser Ala
1               5                   10                  15

Gln Val Gln Lys Gln Arg Asp Lys Glu Leu Gly Leu Gly Arg His Glu
            20                  25                  30

Asn Ala Ile Lys Tyr Leu Gly Gln Asp Tyr Glu Asn Leu Arg Ala Arg
        35                  40                  45

Cys Leu Gln Asn Gly Val Leu Phe Gln Asp Asp Ala Phe Pro Pro Val
    50                  55                  60

Ser His Ser Leu Gly Phe Lys Glu Leu Gly Pro Asn Ser Ser Lys Thr
65                  70                  75                  80

Tyr Gly Ile Lys Trp Lys Arg Pro Thr Glu Leu Leu Ser Asn Pro Gln
                85                  90                  95

Phe Ile Val Asp Gly Ala Thr Arg Thr Asp Ile Cys Gln Gly Ala Leu
            100                 105                 110

Gly Asp Cys Trp Leu Leu Ala Ala Ile Ala Ser Leu Thr Leu Asn Glu
        115                 120                 125

Thr Ile Leu His Arg Val Val Pro Tyr Gly Gln Ser Phe Gln Glu Gly
130                 135                 140

Tyr Ala Gly Ile Phe His Phe Gln Leu Trp Gln Phe Gly Glu Trp Val
145                 150                 155                 160

Asp Val Val Val Asp Asp Leu Leu Pro Thr Lys Asp Gly Lys Leu Val
                165                 170                 175

Phe Val His Ser Ala Gln Gly Asn Glu Phe Trp Ser Ala Leu Leu Glu
            180                 185                 190

Lys Ala Tyr Ala Lys Val Asn Gly Ser Tyr Glu Ala Leu Ser Gly Gly
        195                 200                 205

Cys Thr Ser Glu Ala Phe Glu Asp Phe Thr Gly Gly Val Thr Glu Trp
    210                 215                 220

Tyr Asp Leu Gln Lys Ala Pro Ser Asp Leu Tyr Gln Ile Ile Leu Lys
225                 230                 235                 240

Ala Leu Glu Arg Gly Ser Leu Leu Gly Cys Ser Ile Asn Ile Ser Asp
                245                 250                 255

Ile Arg Asp Leu Glu Ala Ile Thr Phe Lys Asn Leu Val Arg Gly His
            260                 265                 270

Ala Tyr Ser Val Thr Asp Ala Lys Gln Val Thr Tyr Gln Gly Gln Arg
        275                 280                 285

Val Asn Leu Ile Arg Met Arg Asn Pro Trp Gly Glu Val Glu Trp Lys
    290                 295                 300

Gly Pro Trp Ser Asp Asn Ser Tyr Glu Trp Asn Lys Val Asp Pro Tyr
305                 310                 315                 320

Glu Arg Glu Gln Leu Arg Val Lys Met Glu Asp Gly Glu Phe Trp Met
                325                 330                 335

Ser Phe Arg Asp Phe Ile Arg Glu Phe Thr Lys Leu Glu Ile Cys Asn
            340                 345                 350

Leu Thr Pro Asp Ala Leu Lys Ser
        355                 360

<210> SEQ ID NO 5
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<223> OTHER INFORMATION: N-term Dabcyl
<220> FEATURE:
<223> OTHER INFORMATION: C-term Edans

<400> SEQUENCE: 5

Thr Pro Leu Lys Ser Pro Pro Ser Pro Arg
1               5                   10

<210> SEQ ID NO 6
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Carbobenzyloxy
<220> FEATURE:
<223> OTHER INFORMATION: C-term FMK

<400> SEQUENCE: 6

Leu Leu Tyr
1

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Asp Ile Cys Gln Gly Ala Leu Gly Asp Cys Trp Leu Leu Ala Ala
1               5                   10                  15

Ile Ala Ser Leu Thr Asn Glu Thr Ile Leu His Arg
            20                  25

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Suc
<220> FEATURE:
<223> OTHER INFORMATION: C-term AMC

<400> SEQUENCE: 8

Leu Leu Val Tyr
1

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Dabcyl
<220> FEATURE:
<223> OTHER INFORMATION: C-term Edans

<400> SEQUENCE: 9
```

```
Thr Pro Leu Lys Ser Pro Pro Ser Pro Arg
1               5                   10
```

<210> SEQ ID NO 10
<211> LENGTH: 337
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Gly Arg His Glu Asn Ala Ile Lys Tyr Leu Gly Gln Asp Tyr Glu
1               5                   10                  15

Asn Leu Arg Ala Arg Cys Leu Gln Asn Gly Val Leu Phe Gln Asp Asp
                20                  25                  30

Ala Phe Pro Pro Val Ser His Ser Leu Gly Phe Lys Glu Leu Gly Pro
            35                  40                  45

Asn Ser Ser Lys Thr Tyr Gly Ile Lys Trp Lys Arg Pro Thr Glu Leu
50                  55                  60

Leu Ser Asn Pro Gln Phe Ile Val Asp Gly Ala Thr Arg Thr Asp Ile
65                  70                  75                  80

Cys Gln Gly Ala Leu Gly Asp Cys Trp Leu Leu Ala Ala Ile Ala Ser
                85                  90                  95

Leu Thr Leu Asn Glu Thr Ile Leu His Arg Val Val Pro Tyr Gly Gln
                100                 105                 110

Ser Phe Gln Glu Gly Tyr Ala Gly Ile Phe His Phe Gln Leu Trp Gln
            115                 120                 125

Phe Gly Glu Trp Val Asp Val Val Val Asp Asp Leu Leu Pro Thr Lys
130                 135                 140

Asp Gly Lys Leu Val Phe Val His Ser Ala Gln Gly Asn Glu Phe Trp
145                 150                 155                 160

Ser Ala Leu Leu Glu Lys Ala Tyr Ala Lys Val Asn Gly Ser Tyr Glu
                165                 170                 175

Ala Leu Ser Gly Gly Cys Thr Ser Glu Ala Phe Glu Asp Phe Thr Gly
            180                 185                 190

Gly Val Thr Glu Trp Tyr Asp Leu Gln Lys Ala Pro Ser Asp Leu Tyr
        195                 200                 205

Gln Ile Ile Leu Lys Ala Leu Glu Arg Gly Ser Leu Leu Gly Cys Ser
    210                 215                 220

Ile Asn Ile Ser Asp Ile Arg Asp Leu Glu Ala Ile Thr Phe Lys Asn
225                 230                 235                 240

Leu Val Arg Gly His Ala Tyr Ser Val Thr Asp Ala Lys Gln Val Thr
                245                 250                 255

Tyr Gln Gly Gln Arg Val Asn Leu Ile Arg Met Arg Asn Pro Trp Gly
            260                 265                 270

Glu Val Glu Trp Lys Gly Pro Trp Ser Asp Asn Ser Tyr Glu Trp Asn
        275                 280                 285

Lys Val Asp Pro Tyr Glu Arg Glu Gln Leu Arg Val Lys Met Glu Asp
    290                 295                 300

Gly Glu Phe Trp Met Ser Phe Arg Asp Phe Ile Arg Glu Phe Thr Lys
305                 310                 315                 320

Leu Glu Ile Cys Asn Leu Thr Pro Asp Leu Glu His His His His
                325                 330                 335

His
```

<210> SEQ ID NO 11
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Asp Ile Cys Gln Gly Ala Leu Gly Asp Cys Trp Leu Leu Ala Ala
1               5                   10                  15

Ile Ala Ser Leu Thr Leu Asn Glu Thr Ile Leu His Arg
            20                  25

<210> SEQ ID NO 12
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Cys(Carbamidomethyl)
<220> FEATURE:
<221> NAME/KEY: MOD_RES
<222> LOCATION: (11)..(11)
<223> OTHER INFORMATION: Cys(Carbamidomethyl)

<400> SEQUENCE: 12

Thr Asp Ile Cys Gln Gly Ala Leu Gly Asp Cys Trp Leu Leu Ala Ala
1               5                   10                  15

Ile Ala Ser Leu Thr Leu Asn Glu Thr Ile Leu His Arg
            20                  25

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Cys(Carbamidomethyl)
<220> FEATURE:
<221> NAME/KEY: MOD_RES
<222> LOCATION: (11)..(11)
<223> OTHER INFORMATION: Cys(E64)

<400> SEQUENCE: 13

Thr Asp Ile Cys Gln Gly Ala Leu Gly Asp Cys Trp Leu Leu Ala Ala
1               5                   10                  15

Ile Ala Ser Leu Thr Leu Asn Glu Thr Ile Leu His Arg
            20                  25